United States Patent [19]
Ohm et al.

[11] Patent Number: 5,710,870
[45] Date of Patent: Jan. 20, 1998

[54] DECOUPLED SIX DEGREE-OF-FREEDOM ROBOT MANIPULATOR

[75] Inventors: Timothy Ohm, La Crescenta; Curtis Boswell, Pasadena; Hari Das, Altadena, all of Calif.; Eric Paljug, McKees Rock, Pa.; Guillermo Rodriguez, La Canada, Calif.; Paul Schenker, Pasadena, Calif.; Sukhan Lee, La Canada, Calif.; Ed Barlow, San Dimas, Calif.; Steve Charles, Geramtown, Tenn.

[73] Assignee: California Institute of Technology, Pasadena, Calif.

[21] Appl. No.: 525,813

[22] Filed: Sep. 7, 1995

[51] Int. Cl.$^6$ .............................. G05G 11/00; G05B 19/00
[52] U.S. Cl. .................... 395/98; 395/97; 395/80; 395/86; 901/27; 901/30
[58] Field of Search ..................... 395/97, 98, 80, 395/86; 901/27, 30

[56] References Cited

U.S. PATENT DOCUMENTS

| | | | |
|---|---|---|---|
| 4,686,866 | 8/1987 | Rosheim | 74/479 |
| 4,723,460 | 2/1988 | Rosheim | 74/479 |
| 4,729,253 | 3/1988 | Rosheim | 74/479 |
| 4,804,220 | 2/1989 | Rosheim | 74/479 |
| 4,828,453 | 5/1989 | Martin et al. | 901/26 |
| 4,865,376 | 9/1989 | Leaver et al. | 901/15 |
| 4,887,222 | 12/1989 | Miyake et al. | 395/98 |
| 4,894,788 | 1/1990 | Stelzer | 395/98 |
| 4,911,033 | 3/1990 | Rosheim | 74/479 |
| 4,928,047 | 5/1990 | Arai et al. | 901/9 |
| 4,937,759 | 6/1990 | Vold | 395/97 |
| 4,942,538 | 7/1990 | Yuan et al. | 395/98 |
| 5,036,724 | 8/1991 | Rosheim | 74/479 |
| 5,293,461 | 3/1994 | Grudie et al. | 395/98 |
| 5,550,953 | 8/1996 | Seraji | 395/98 |
| 5,581,166 | 12/1996 | Eismann et al. | 901/9 |
| 5,590,034 | 12/1996 | Snell | 395/98 |

*Primary Examiner*—George B. Davis
*Attorney, Agent, or Firm*—Michaelson & Wallace

[57] ABSTRACT

The present invention is a double-jointed, tendon-driven revolute joint, a decoupled tendon-driven wrist, an antibacklash mechanism, a robot control system, and a robot manipulator incorporating the double-jointed, tendon-driven revolute joint, decoupled tendon-driven wrist, and antibacklash mechanism. The robot manipulator is a microsurgical teleoperated robot with actuators located at an actuator base. The overall system architecture includes a slave robot manipulator coupled to an amplifier chassis which is coupled to a control chassis. The control chassis is coupled to a workstation with a graphical user interface. Components of the robot manipulator are categorized into a mechanical sub-system, an electronics sub-system, a servo-control sub-system, and a high-level software control sub-system.

64 Claims, 21 Drawing Sheets

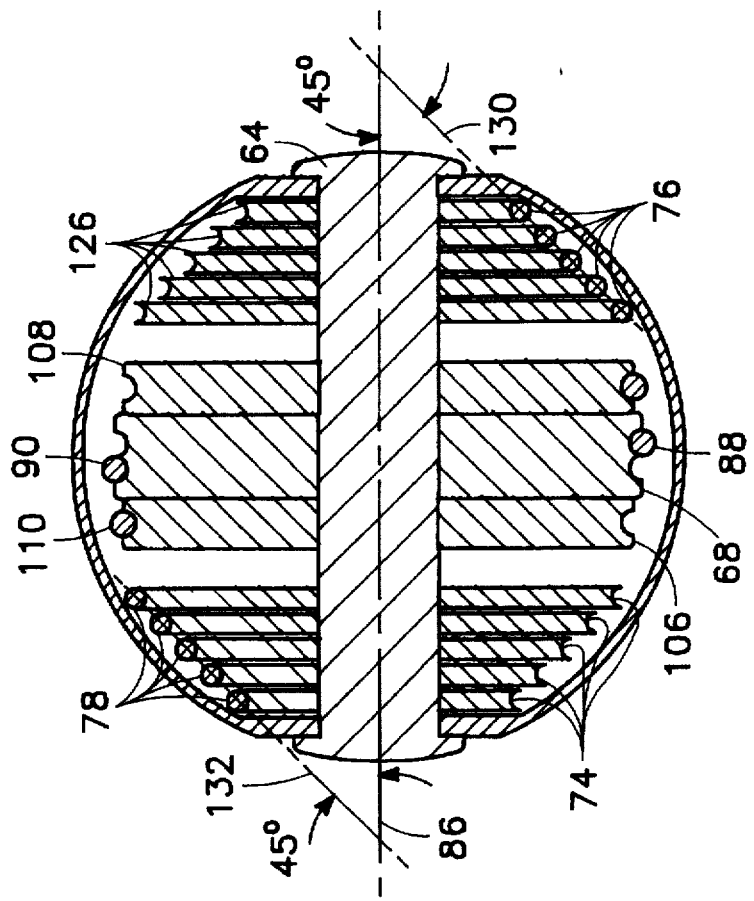
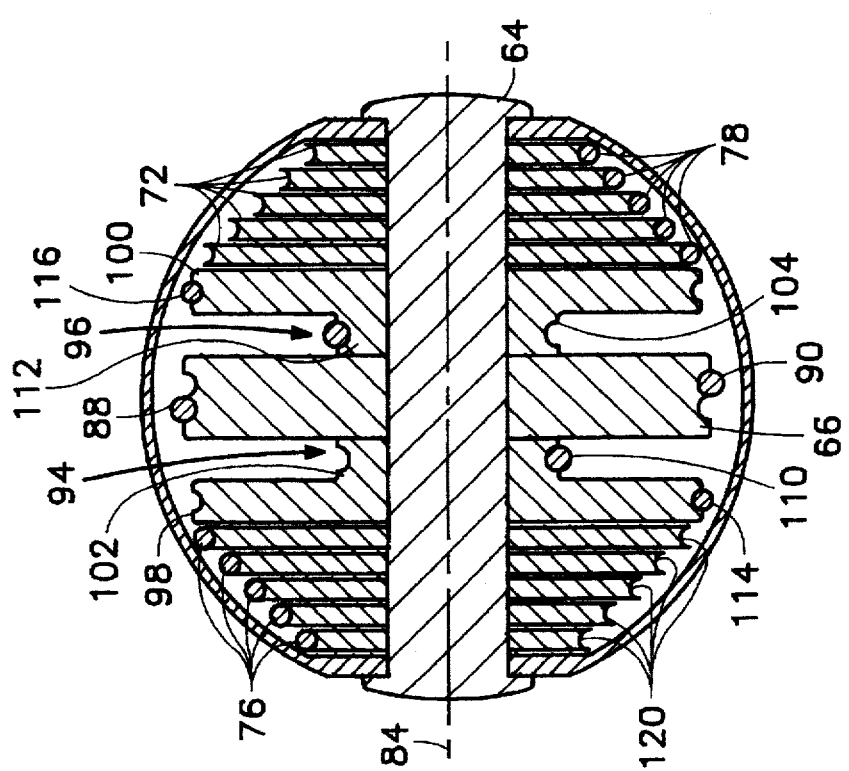
FIG. 8
FIG. 7

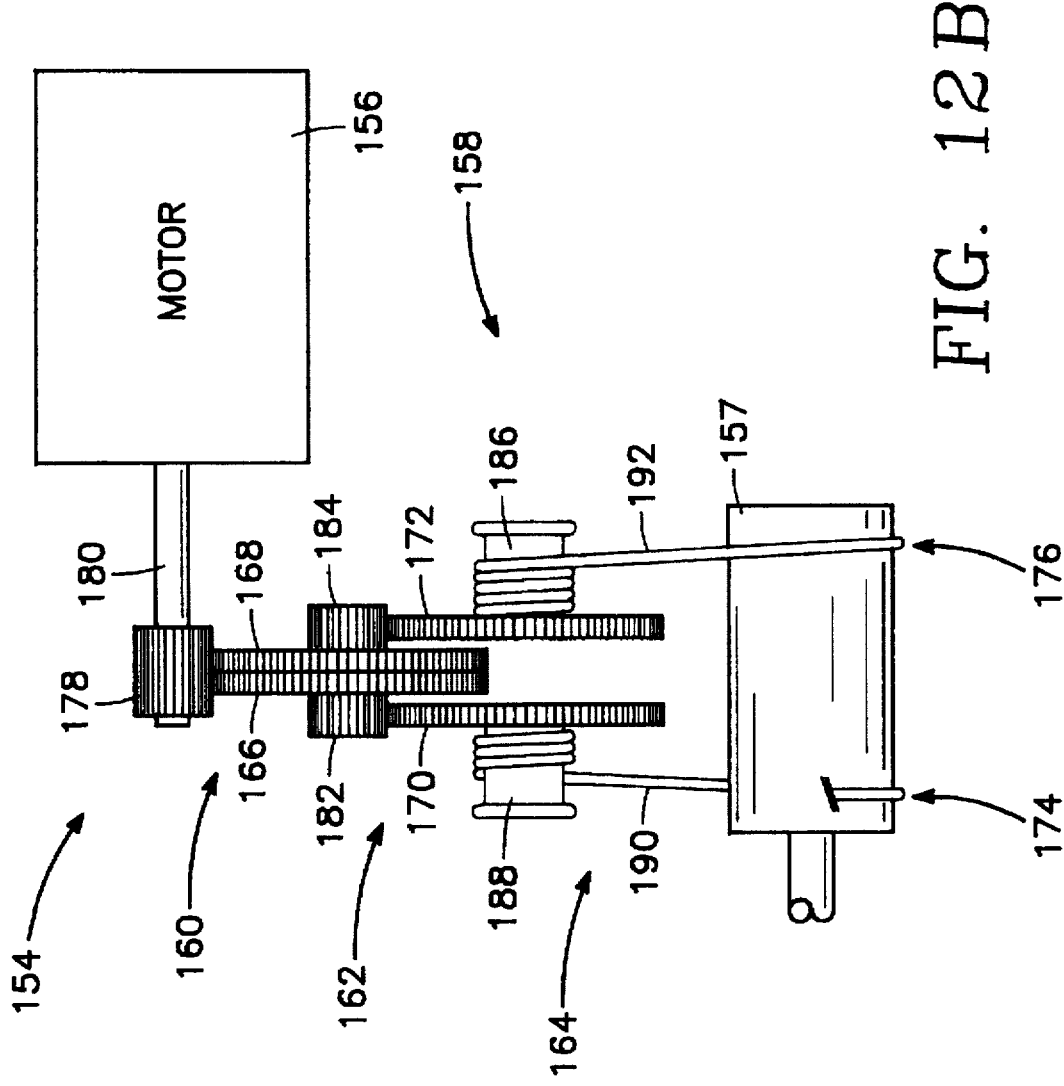
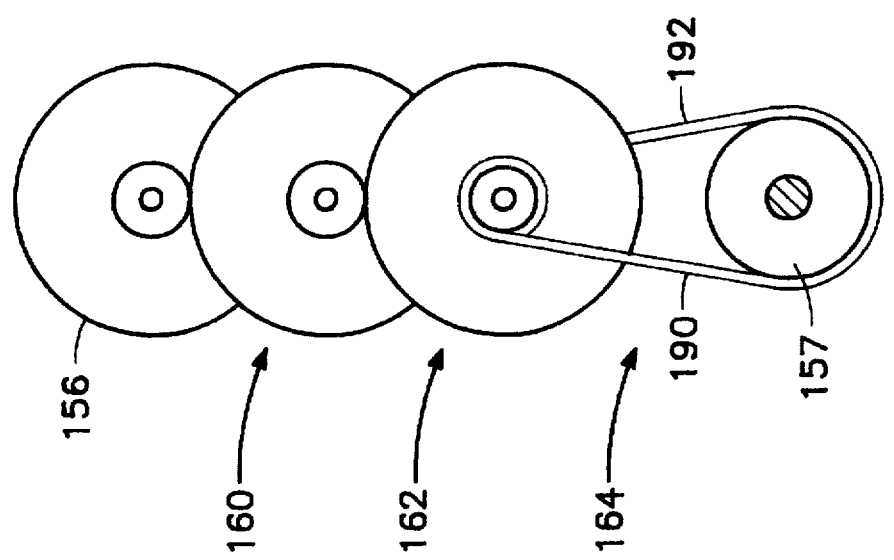
FIG. 12B
FIG. 12A

DECOUPLED SIX DEGREE-OF-FREEDOM ROBOT MANIPULATOR

BACKGROUND OF THE INVENTION

ORIGIN OF THE INVENTION

The invention described herein was made in the performance of work under a NASA contract, and is subject to the provisions of Public Law 96-517 (35 USC 202) in which the contractor has elected to retain title.

COPYRIGHT NOTICE

A portion of the disclosure of this patent document, including, but not limited to the Appendix, contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates in general to robot manipulators and in particular to double-jointed, tendon-driven revolute joints, a decoupled tendon-driven wrist, an antibacklash mechanism, a robot control system, and a microsurgical teleoperated robot having high dexterity and incorporating the double-jointed, tendon-driven revolute joints, decoupled tendon-driven wrist, and antibacklash mechanism.

RELATED ART

Robotic devices are commonly used in factory based environments to complete tasks such as placing parts, welding, spray painting, etc. Examples of robotic systems include U.S. Pat. No. 4,911,033, issued to Rosheim et al., and U.S. Pat. Nos. 4,729,253, 4,723,460, and 4,686,866, issued to Rosheim.

Although these systems are used for a variety of tasks, the Rosheim et al. and Rosheim robotic systems lack important features. For instance, they do not have completely mechanically decoupled axes with passed actuation for transferring actuation through one joint in order to actuate another joint, without affecting the motion of any other joints. In addition, the Rosheim et al. and Rosheim robotic systems are large and bulky and cannot effectively perform small scale tasks, such as microsurgical operations. Also, the Rosheim et al. and Rosheim robotic systems are not tendon-driven systems, and thus, do not have low or zero backlash, which is desirable for microsurgical operations.

Recently, other robotic devices have been used in medical environments to perform surgical operations. Some of these devices include micro-robots having miniaturized end effectors with tendon-driven joints. However, current tendon-driven robot manipulators for small scale microsurgical manipulation suffer from inefficient coupling between joints, inadequate stiffness, packaging problems associated with achieving constant cable path lengths, and activation of multiple joints.

Also, in many robotic geartrain applications, such as high precision microsurgical operations, zero backlash is desired. Conventional approaches use various antibacklash components, such as high precision connectors and antibacklash gears, to eliminate backlash in each stage of the geartrain independently. These antibacklash gears are used in each stage and are stacked until the desired gear ratio is achieved. Nevertheless, these conventional approaches are difficult to implement since each stage of the geartrain ideally requires a unique preload (initial loading of the geartrain to snugly 'set' the gears within each other) value. Moreover, preloading is typically tedious and difficult to readjust, if required.

Therefore, what is needed is a robot with passed actuation capabilities, zero backlash, high dexterity, and at least six degrees of freedom with all six axes being completely mechanically decoupled.

Whatever the merits of the above mentioned systems and methods, they do not achieve the benefits of the present invention.

SUMMARY OF THE INVENTION

To overcome the limitations in the prior art described above, and to overcome other limitations that will become apparent upon reading and understanding the present specification, the present invention is a double-jointed, tendon-driven revolute joint, a decoupled tendon-driven wrist, an antibacklash mechanism, a robot control system, and a robot manipulator incorporating the double-jointed, tendon-driven revolute joint, decoupled tendon-driven wrist, and antibacklash mechanism.

The robot manipulator of the present invention is a microsurgical teleoperated robot with actuators located at an actuator base. The overall system architecture includes a slave robot manipulator coupled to an amplifier chassis which is coupled to a control chassis. The control chassis is coupled to a workstation with a graphical user interface. Components of the robot manipulator are categorized into a mechanical sub-system, an electronics sub-system, a servo-control sub-system, and a high-level software control sub-system.

The robot manipulator has six degrees of freedom and includes a torso connected to the actuator base (which rotates about a housing canister). The torso is also rotatably coupled to an arm. The arm comprises two double-jointed robot joints decoupled from each other and a three-axis wrist joint connected to an end effector. The double-jointed robot joints include an input link having a first keying drive component and an output link coupled to the input link and having a second keying drive component. The first keying drive component is constrained to rotate with respect to the second keying drive component, thereby defining an instantaneous center of rotation.

In addition, each double-jointed decoupled joint has a first passing drive component rotatable on the input link and coupled to the actuator of the actuator base. A second passing drive component rotatable on the output link is coupled to the first passing drive component. The first passing drive component rotates with respect to the second passing drive component about the instantaneous center of rotation. The pair of passing drive components are kinematically linked to the keying drive component through the instantaneous center of rotation so that each passing drive component of each joint is completely mechanically decoupled from the particular joint's motion. Further, any number of pairs of passing drive components can be used with each decoupled joint as long respective pairs of passing drive components rotate with respect to each other about the instantaneous center of rotation. Moreover, each joint can have an actuation drive component for actuating the particular joint.

The three axis wrist is connected to the end effector and has a tendon-driven system with three decoupled axes and zero backlash in two of the three axes. The wrist utilizes a dual universal drive component system to provide a three degree-of-freedom, singularity free, mechanically decoupled joint that operates in a full hemisphere of motion (up to 90 degrees in any direction).

The antibacklash geartrain is incorporated in the robot manipulator between the actuators at the actuator base and the device to be actuated, such as the output link of a particular joint. The antibacklash mechanism is a multiple stage device, not limited to any particular number of stages, utilizing a drivetrain system with drive components such as gears, belts, and/or cables. The antibacklash mechanism has two independent parallel transmission paths for each drivetrain. The drivetrains are mechanically coupled only at an input, such as the motor, and an output, such as an actuation pulley located on a particular joint. This system allows convenient preloading of all the stages simultaneously.

The advantages of the teleoperated microsurgical robot of the present invention is that it is extremely sensitive and small, has high dexterity, has double-jointed robot joints, has at least six degrees of freedom with all six axes completely mechanically decoupled, decoupled passed actuation and has zero backlash with convenient preload adjustment of all stages simultaneously.

The foregoing and still further features and advantages of the present invention as well as a more complete understanding thereof will be made apparent from a study of the following detailed description of the invention in connection with the accompanying drawings and appended claims.

BRIEF DESCRIPTION OF THE DRAWINGS

Referring now to the drawings in which like reference numbers represent corresponding parts throughout:

FIG. 7 illustrates a cross sectional side view of the input link of FIG. 4;

FIG. 8 illustrates a cross sectional side view of the output link of FIG. 4;

FIG. 12A illustrates a side view of the antibacklash mechanism of the present invention;

FIG. 12B illustrates a front view of the antibacklash mechanism of the present invention;

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

ROBOT MANIPULATOR OVERVIEW

Figure 1:
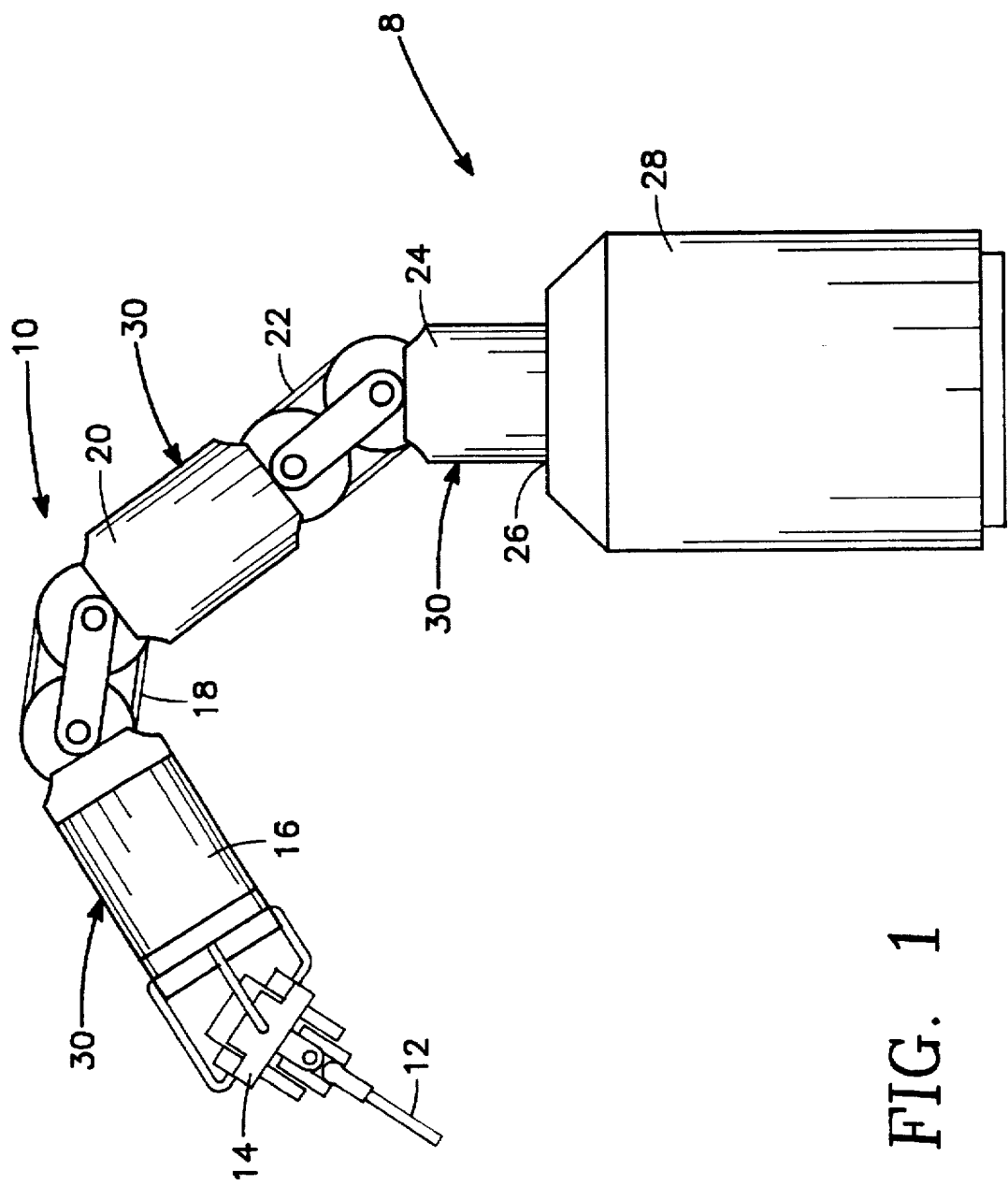
FIG. 1 illustrates an overall view of the robot manipulator of the present invention.

FIG. 1 illustrates an overall view of a robot manipulator 8 of the present invention. In the preferred embodiment, the robot manipulator 8 has six degrees of freedom and includes an arm 10 with an end effector 12 coupled to a three-axis wrist joint 14, which is coupled to a forearm 16. The forearm 16 is coupled to a doubled-jointed elbow joint 18 for connecting an upper arm 20 to the forearm 16. The upper arm 20 is coupled to a double-jointed shoulder joint 22 for connecting a shoulder 24 to the upper arm 20. The shoulder 24 is coupled to a torso joint 26 which is coupled to an actuator base 28. The actuator base 28 contains electrical and mechanical components for controlling the movements of the robot 8. The forearm 16, upper arm 20, and shoulder 24 all preferably have housings in the form of cylindrical casings 30. The torso joint 26 rotates the arm 10 relative to the actuator base 28. The wrist joint 14 has three degrees of freedom and each joint (elbow 18, shoulder 22, and torso 26) has one degree of freedom.

The double-jointed robot joints 18 and 22 and the wrist joint 14 can be used in large automated environments, as well as micro automated environments, including microsurgical environments. The double-jointed robot joints 18 and 22 will be discussed in detail below in FIGS. 2-10 and the wrist joint will be discussed in detail below in FIG. 11. The robot manipulator is described in detail in FIGS. 12-26 below. Although the robot manipulator can be used in numerous environments, the preferred embodiment involves the use of the robot manipulator in a microsurgical environment.

DOUBLE-JOINTED, DECOUPLED JOINTS

Figure 2:
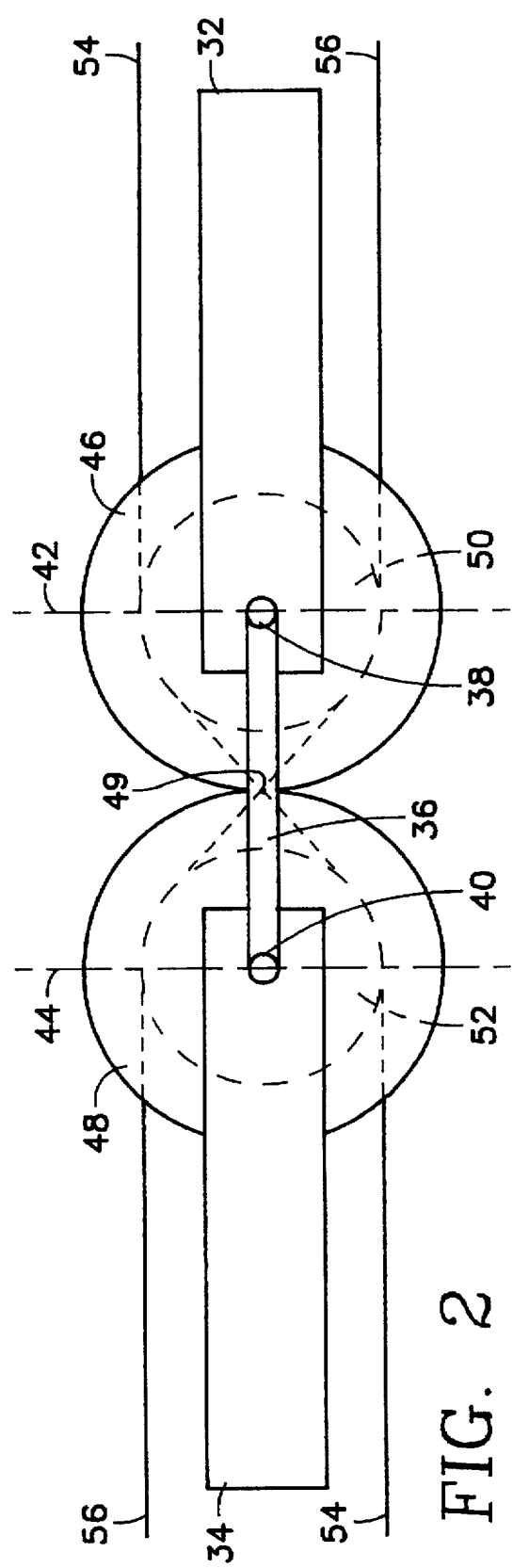
FIG. 2 illustrates a side view of the general decoupled robot joints of the present invention.
Figure 3:
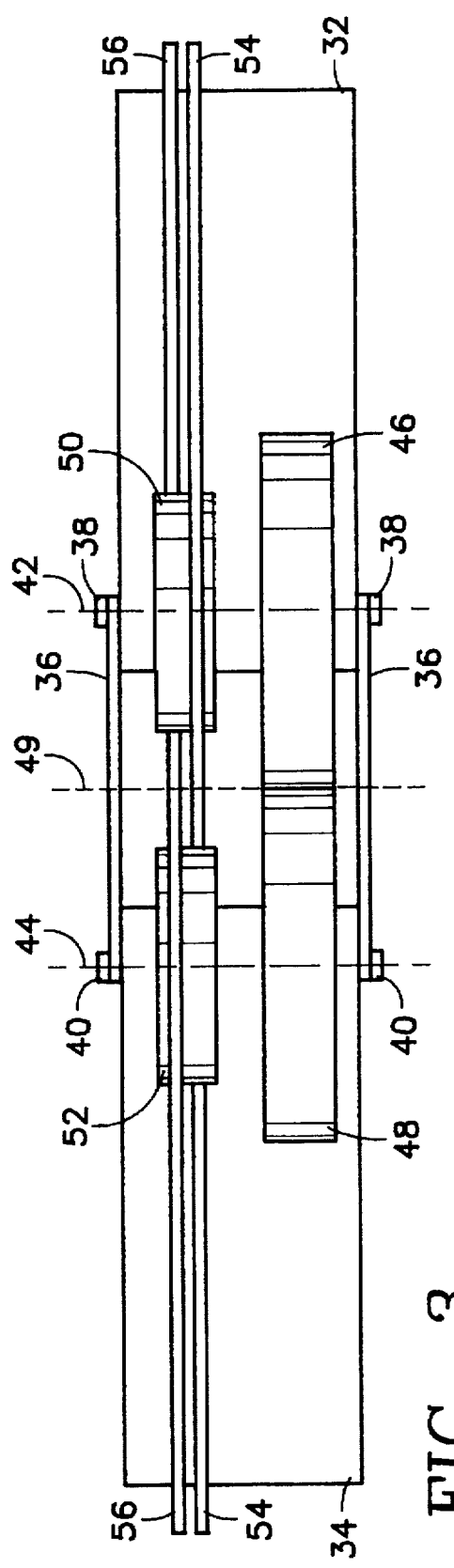
FIG. 3 illustrates a top view of FIG. 2.

FIG. 2 is a side view and general overview of a double-jointed, decoupled robot joint of the present invention. FIG. 3 illustrates a top view of FIG. 2. The double-jointed robot joint couples sections of the robot 8 of FIG. 1 together. Each double-jointed robot joint can have internal actuators, such as an internal actuation pulley/cable system (described in detail in FIGS. 4-8) coupled to external motors located at the actuator base 28 of FIG. 1 or internal motors in each joint (not shown) for actuating the particular joint or other joints of the robot.

The double-jointed robot joint of FIGS. 2 and 3 includes an input link 32 and an output link 34. The input link 32 is on the near side of the actuator base 28 while the output link 34 is on the far side of the actuator base 28 and is moveable relative to the input link 32. The input and output links 32, 34 are attached to each other via a pair of hinged side struts 36. The links 32, 34 pivot about pivot points 38 and 40 at the input link 32 and output link 34, respectively. These pivot points 38 and 40 define an input axis 42 and output axis 44, respectively.

An input keying drive component 46 and an output keying drive component 48 are centered on each respective hinged axis or pivot point 38 and 40 and are attached to each respective link 32 and 34 so that they are constrained to rotate with respect to each other. This constrained rotation between the input keying drive component 46 and the output keying drive component 48 defines an instantaneous center 49 of rotation between the two keying drive components 46 and 48. The keying drive components 46 and 48 can be fixed spur gears which mesh together or they can be fixed pulleys with wound cables as described in detail below.

In addition, each joint has an input passing drive component 50 rotatable about the pivot point 38 of the input link 32. The input passing drive component 50 is coupled to an actuator (not shown) at the actuator base 28 of FIG. 1 and to an output passing drive component 52. The output passing drive component 52 is rotatable about the pivot point 40 of the output link 34. The passing drive components 50 and 52 can be a spur gear system or a pulley system. In a pulley system, respective passing cables passing through each respective passing drive component would be included.

For example, a first passing cable 54, originating from another passing drive component in another joint or from the actuator base 28 of FIG. 1, travels from the input link 32, around the top of the input passing pulley 50, through the instantaneous center 49 of rotation, and then around the bottom of the output passing pulley 52. A second passing cable 56, originating from the same location as the first passing cable 54, travels from the input link 32, around the bottom of the input passing pulley 50, through the instantaneous center 49 of rotation, and then around the top of the output passing pulley 52. The passing cables 54, 56 can be actuated in a forward or reverse direction to actuate a particular joint in a desired direction.

This arrangement allows the input passing drive component 50 to rotate with respect to the output passing drive component 52 about the same instantaneous center 49 of rotation defined by the input and output keying drive components 46 and 48. Since the pair of passing drive components rotate about the same instantaneous center 49 of rotation as the keying drive components 46 and 48, the passing drive components 50 and 52 are kinematically decoupled from the joint's motion. This decoupling configuration allows the passing drive components 50 and 52 to actuate movement in other joints without affecting the motion of the particular joint.

Further, any number of pairs of passing drive components can be used with each joint as long as coupled pairs of passing drive components (input and output) rotate with respect to each other about the same instantaneous center of rotation defined by the keying drive components.

DOUBLE-JOINTED TENDON-DRIVEN DECOUPLED JOINTS

Figure 4:
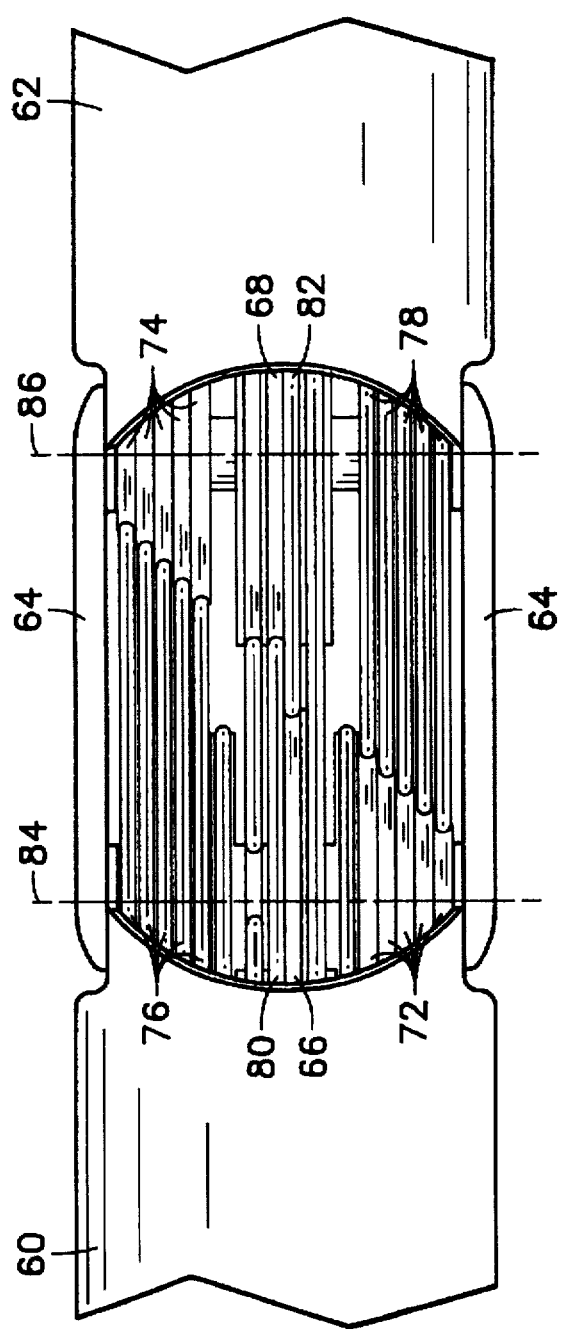
FIG. 4 illustrates a top view of one embodiment of the decoupled joints with cable driven actuation.
Figure 5:
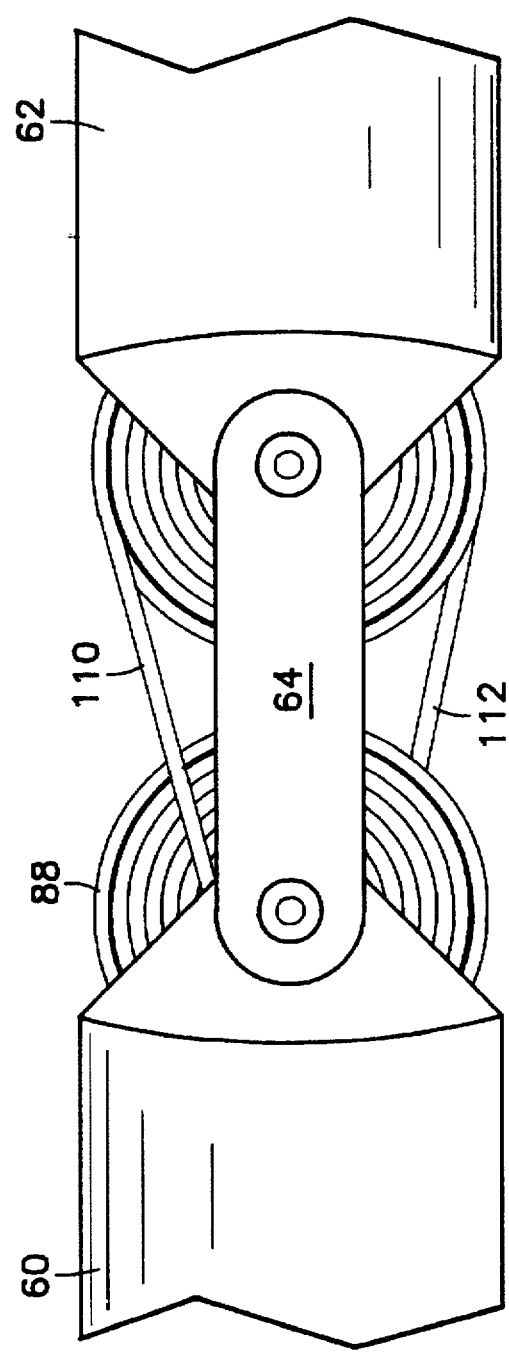
FIG. 5 illustrates a side view of FIG. 4.

FIGS. 4-10 show a tendon-driven system of one embodiment of the double-jointed decoupled robot joints. FIG. 4 is a top view and FIG. 5 is side view of tendon-driven double-jointed decoupled robot joints. The joint of FIG. 4 is structurally similar to the joint of FIGS. 2 and 3 and includes an input link 60, an output link 62, hinged side struts 64, an input keying drive component 66, an output keying drive component 68, an instantaneous center 70 of rotation (shown in FIG. 6), input passing drive components 72, output passing drive components 74, and corresponding passing cables 76 and 78, respectively.

The functions of each element above has the same or similar functions as the related elements of FIGS. 2 and 3. However, the embodiment of FIGS. 4-10 is different in that it is a cable or tendon-driven system and further includes an actuation mechanism. Since the embodiment of FIGS. 4-10 is a cable or tendon-driven robot, the keying drive components 66 and 68 are pulleys with corresponding cables 80 and 82, respectively, which can be stainless steel cables. Also, FIGS. 4-10 further include actuation pulleys and cables within the particular joint for actuating the joint.

The input keying pulley 66 is fixed to the input link 60 and the output keying pulley 68 is fixed to the output link 62 on respective input and output axes 84 and 86. The input axis 84 is defined by a pivot point of the input keying pulley 66 on the input link 60. An output axis 86 is the counterpart to the input axis 84 and is defined by a pivot point of the output keying pulley 68 on the output link 62.

Figure 6:
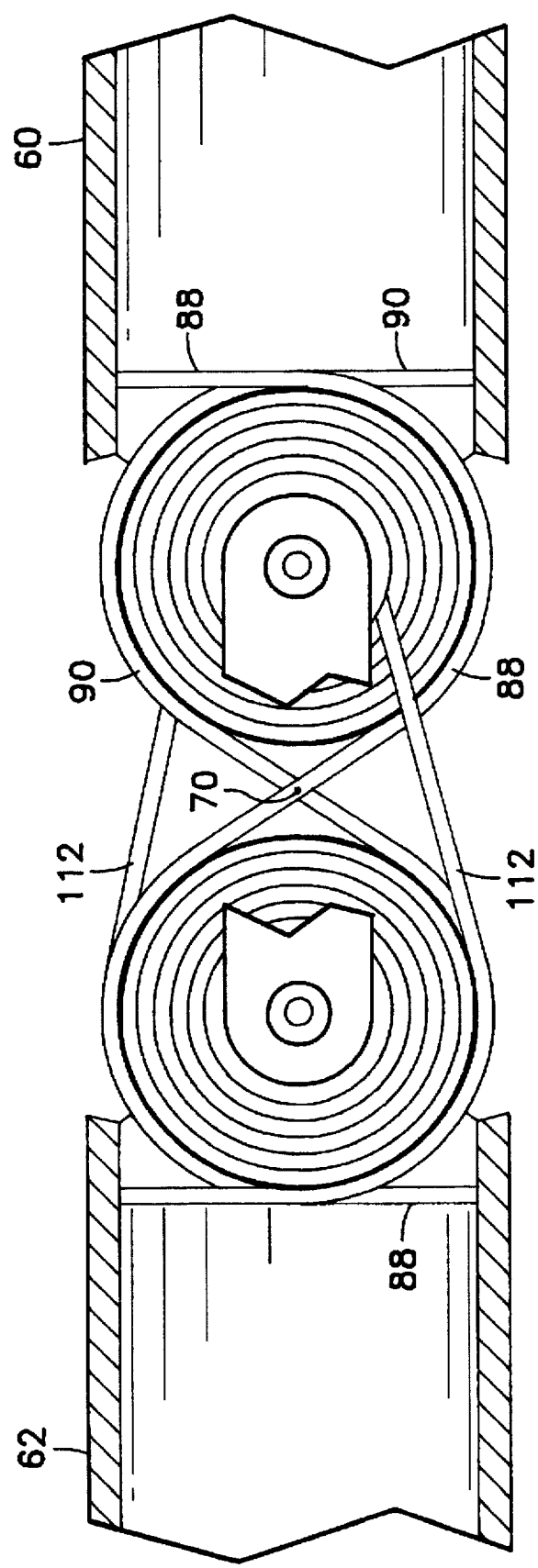
FIG. 6 illustrates a cut-away side view of FIG. 5.

Referring to FIG. 6, two keying cables 88 and 90 are connected to the input link 60 and the output link 62, respectively. The keying cables 88 and 90 can also be connected directly to the keying pulleys 66 and 68, respectively. The first keying cable 88 is attached to a bottom portion of the input link 60 and winds around a top side of the input keying pulley 66, crosses to the output keying pulley 68, winds around a bottom side of the output keying pulley 68, and terminates on a top portion of the output link 62.

The second keying cable 90 is attached to a top portion of the input link 60 and winds around a bottom side of the input keying pulley 66, crosses to the output keying pulley 68, winds around a top side of the output keying pulley 68, and terminates on a bottom portion of the output link 62. The second keying cable 90 traverses a mirrored path of the first keying cable 88. If the cables are stainless steel, the cables 88 and 90 can be terminated with solder joints or crimp terminations. However, soldered terminations are preferred because they are easy to install, take up very little space, and do not inflict an initial stress concentration in the cable, assuming the solder joint is not flexed.

The keying pulleys are constrained to respective links similar to the keying drive component arrangement of FIGS. 2 and 3. Also, the keying pulleys 66 and 68 preferably have the same diameter, but this is not necessary. One feature of the present invention is that the keying cables 88 and 90 cross one another between the keying pulleys 66 and 68 as shown in FIG. 6 to define the instantaneous center 70 of rotation. The identical effect of having an instantaneous center of rotation can be achieved with spur gears which mesh together, in a similar manner as the keying drive components 46 and 48 of FIGS. 2 and 3. Although, keying spur gears would introduce backlash into the robot manipulator, backlash can be prevented in the tendon-driven system in accordance with the antibacklash system described in detail in FIG. 12. Thus, the present invention is preferably a tendon-driven system consisting of keying cables 88 and 90 and keying pulleys 66 and 68 instead of spur gears.

Figure 9:
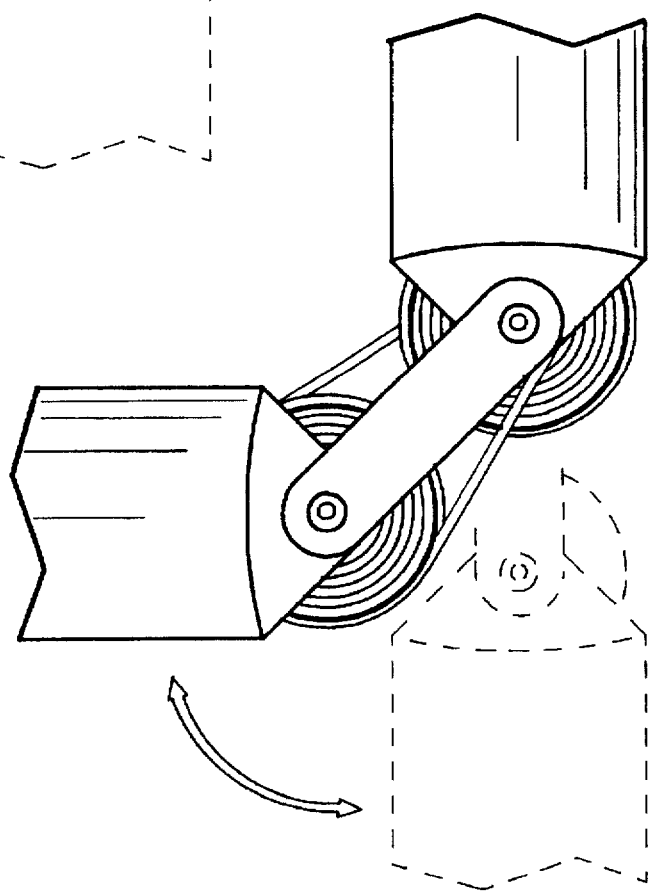
FIG. 9 illustrates a 90 degree deflection of the robot arm connected to the decoupled joint of the present invention.

The passing or actuation cables can be actuated in a forward or reverse direction to actuate a particular joint in a desired direction. Each double-jointed robot joint has one degree of freedom. Each joint's rotation is dependant on the ratio of the keying pulleys' 66 and 68 diameters. For example, if both keying pulleys 66 and 68 have the same diameter, the angle that the output link 62 is moved relative to the input link 60 will be exactly twice the angle between the side struts 64 and each link 60 and 62. In other words, if the output link 62 is rotated 90° to the input link 60, the side struts 64 will rotate 45° to each link 60 and 62, as shown in FIG. 9. Likewise, the output link 62 can rotate up to 180° at which point the side struts 64 will be at 90° to each link 60 and 62, as shown in FIG. 10.

Figure 10:
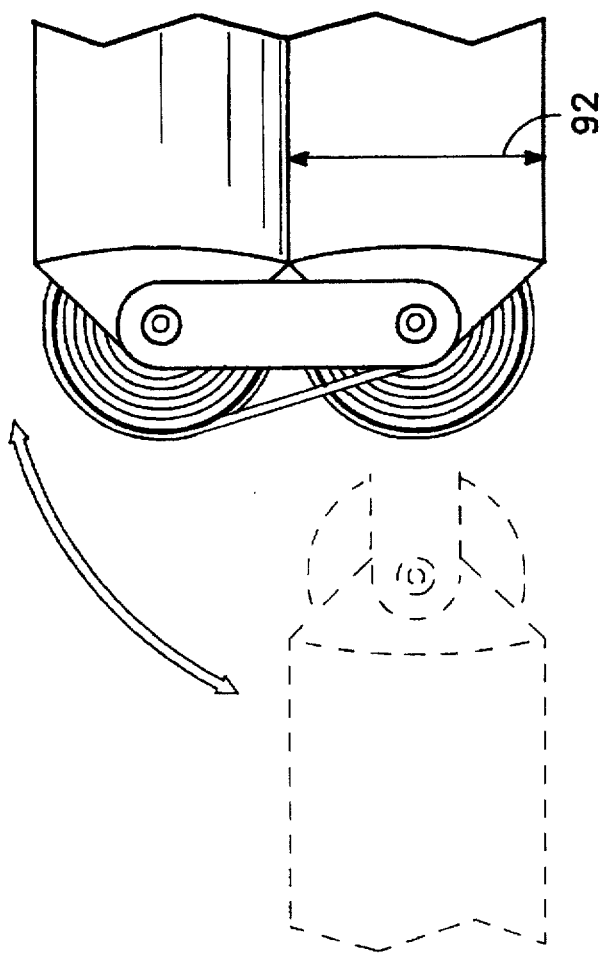
FIG. 10 illustrates a 180 degree deflection of the robot arm connected to the decoupled joint of the present invention.

In order to achieve the maximum 180° rotation, the distance between the input and output axes must be at least equal or greater than an effective diameter 92 of each links 60 and 62, as shown in FIG. 10. It is important to note that the 180° range of motion is bidirectional, thus the full range of joint motion is 360°. Alternatively, if the keying pulleys 66 and 68 have different diameters, other kinematic relationships can be achieved between the input link 60, output link 62, and side struts 64 without affecting other features of the robot.

FIGS. 7 and 8 are cross-sectional views through the input and output axes, respectively. The joint can be actuated by two input dual actuation pulleys 94 and 96. Each input dual actuation pulley 94 and 96 includes transmission pulleys 98 and 100 and connecting pulleys 102 and 104, respectively. The two input dual actuation pulleys 94 and 96 sandwich the input keying pulley 66 on the input axis 84 as shown in FIG. 7. The actuation pulleys 94 and 96 rotate independently of the input keying pulley 66.

Also, two output actuation pulleys 106 and 108 sandwich the output keying pulley 68 on the output axis 86 as shown in FIG. 8. Referring to both FIGS. 7 and 8, each of the connecting pulleys 102 and 104 have corresponding actuation cables 110 and 112 terminated to it. Also, the transmission pulleys 98 and 100 have transmission cables 114 and 116 coupled to the actuator base for actuating the pulleys 94 and 96.

Referring to FIGS. 6–8, the first actuation cable 110 can be terminated to a top side of the connecting pulley 102 of the first input actuation pulley 94 and the second actuation cable 112 can be terminated to a bottom side of the connecting pulley 104 of the second input actuation pulley 96. The first actuation cable 110 travels from the first input actuation pulley 94, winds around a top side of the first output actuation pulley 106, and terminates to a bottom side of the output link 62. The second actuation cable 112 travels from the second input actuation pulley 96, winds around a bottom side of the second output actuation pulley 108, and terminates to a top side of the output link 62. Connecting pulleys 102 and 104 can have the same diameters of actuation pulleys 106 and 108, but this is not necessary. The transmission cables 114 and 116 are coupled to the transmission pulleys 98 and 100 of the input actuation pulleys 94 and 96, respectively, to actuate the output actuation pulleys 106 and 108 through the connecting pulleys 102 and 104 via the actuation cables 110 and 112.

Motors typically operate at high speeds with low torque. However, actuation of the robot joints by motors located at the actuator base typically requires the motor to have low speed with high torque. Gear reduction at the joints resolves this problem by reducing a motor's high speed with low torque to low speed with high torque. The actuation pulleys 106 and 108 can incorporate gear reduction at the joints. For example, if the connecting pulleys 102 and 104 of the input actuation pulleys 94 and 96 have the same diameters, and the output actuation pulleys 106 and 108 have the same diameters, and the connecting pulleys 102 and 104 have different diameters from the output actuation pulleys 106 and 108, a resultant gear reduction ratio for the particular joint will be created.

The resultant gear reduction ratio between the input actuation pulleys 94 and 96 and the output actuation pulleys 106 and 108 is given by:

$$\text{RATIO} = \tfrac{1}{2}(1 + d_o/d_i)$$

where $d_o$ is the diameter of the output actuation pulleys 106 and 108 and $d_i$ is the diameter of the connecting pulleys 102 and 104 of the input actuation pulleys 94 and 96. This relationship also assumes that both keying pulleys 66 and 68 have the same diameter. Therefore, if the ratio of the diameters of the output actuation pulleys 106 and 108 to the diameters of the connecting pulleys 102 and 104 of the input actuation pulley is 3:1, the resultant gear ratio for the joint will be 2:1 (the output actuation pulley revolves once for every two revolutions of the input actuation pulley).

Also, gear reduction in close proximity to the joint increases stiffness. Typically, stiffness of a tendon-driven mechanism is directly related to the spring constant of the cable or tendon. Thus, high stiffness is achieved by a high spring constant. In addition, the spring constant is inversely proportional to the cable or tendon length. Hence, short cable paths will yield a high spring constant which in turn produces high stiffness. Relatively high stiffness can be achieved with relatively larger diameter cables or tendons.

A resultant gear reduction ratio of 2:1 will produce a short actuation cable length and relatively high stiffness in the transmission cables 114 and 116. The stiffness is related to the resultant gear ratio by a factor of the resultant gear ratio squared. Thus, the diameter of the transmission cables 114 and 116 can be small, thereby enabling small bend radii and more compact packaging.

Similar to the keying drive components of FIGS. 2 and 3, the actuation pulleys/cables can be a spur gear arrangement which would further increase stiffness. However, unlike the keying drive components 48 and 50 of FIGS. 2 and 3, the use of spur gears with dual transmission path cables 114 and 116 (two transmission paths from the actuator) for the actuation pulleys/cables would not induce backlash into the robot manipulator system. This is because the dual transmission paths are tied together at the actuator of the actuator base of FIG. 1 and the output link only. For example, as a result of the actuation pulley arrangement, the tension in the transmission paths defined by the transmission cables 114 and 116 will automatically preload the actuation cables 110 and 112. Further, if the actuation cables 110 and 112 were replaced with a spur gear train, preloading would likewise occur due to this dual transmission path arrangement.

Referring to FIGS. 4, 7, and 8, the joint of the robot manipulator of the present invention also includes an idler pulley/passing cable system. Passing cables 76 and 78 of passing pulleys 72 and 74 pass through a particular joint to actuate other joints of the robot manipulator, thereby mechanically decoupling the particular joint's motion from the other joints' motion. The passing cables 76 and 78 pass through the joint over input idler pulleys 120 and output 126 idler pulleys. The input idler pulleys 72 and 120 and output idler pulleys 74 and 126 rotate freely about the input axis 84 and output axis 86, respectively. The robot can have an unlimited number of idler pulleys and corresponding passing cables.

In order effectuate complete decoupling from the particular joint's motion to other joints' motion, two constraints must be met. First, for a given passing cable 78, corresponding input 72 and output 74 idler pulleys must have the same diameter ratio as that of the input 66 and output 68 keying pulleys, respectively. For example, if the keying pulleys 66 and 68 have equal diameters (1:1 ratio), the idler pulleys 72 and 74 for a corresponding passing cable 78 must have equal diameters (1:1 ratio), or coupling will occur. The absolute size of the idler pulleys 72 and 74 have no consequence.

The second constraint is that the passing cables 78 must follow the same path as the keying cables 88 and 90 and define the same instantaneous center 70 of rotation as the keying cables 88 and 90. Namely, the passing cables 78 must cross from the idler pulleys 72 on input axis 84 to the idler pulleys 74 on the output axis 86 at the same location the keying cables 88 and 90 cross. As a result, as the joint rotates, the amount of passing cable 78 that is wound onto one idler pulley 72 on the input axis 84 equals the amount of passing cable 78 that is unwound off the idler pulley 74 on the output axis 86.

Also, since the keying pulleys 66 and 68 do not rotate relative to their corresponding links 60 and 62, and the passing cables 78 are cabled via the same scheme as the keying cables 88 and 90, the idler pulleys 72 and 74 are stationary relative to the links 60 and 62. This produces complete decoupling of the joint and the passing cables 78. Further, there is no restriction (other than physical packaging) to the amount of passing cables 78 that can be passed through a particular joint.

In addition, the passing cables 78 path lengths are constant throughout the entire range of travel. Depending on the idler pulley 72 and 74 diameters, it may be necessary to confine the passing cables 78 to prevent lifting off their corresponding idler pulleys 72 and 74. Confinement can be accomplished by wrapping the passing cables 78 completely around the corresponding idler pulleys 72 and 74, or by adding idler pulleys (not shown) inside the links 60 and 62.

If adjacent joints are to be moved perpendicular to one another (the output link of one joint attaches to the input link of another joint such that the resulting output and input axes are perpendicular), two additional constraints on the passing cables 78 are necessary. The first constraint is that two sets of independent idler pulleys, each consisting of an input idler pulley and an output idler pulley, are needed for each path of cable. The second constraint is that the passing cables 78 must be arranged in such a way that they will align to idler pulleys on the next perpendicular joint. In other words, all the passing cables 78 on their respective idler pulleys of a particular joint must align smoothly onto the idler pulleys of a connecting joint.

For example, FIGS. 7 and 8 illustrate one embodiment to achieve smooth alignment. A first set of passing cables 78 are arranged on incrementally smaller idler pulleys to form a 45° imaginary line 132 on one side of the keying pulley. Likewise, a second set of passing cables 76 are symmetrically arranged on incrementally smaller idler pulleys about the joint's center to form a 45° imaginary line 130 on an opposite side of the keying pulley. As a result, the joint can be rotated at 90° increments and still align with the previous joint. Other angular increments can be achieved by positioning the passing cables in other configurations as long as all the passing cables on their respective idler pulleys of a particular joint are aligned smoothly onto the idler pulleys of a connecting joint.

DECOUPLED TENDON-DRIVEN WRIST

Figure 11:
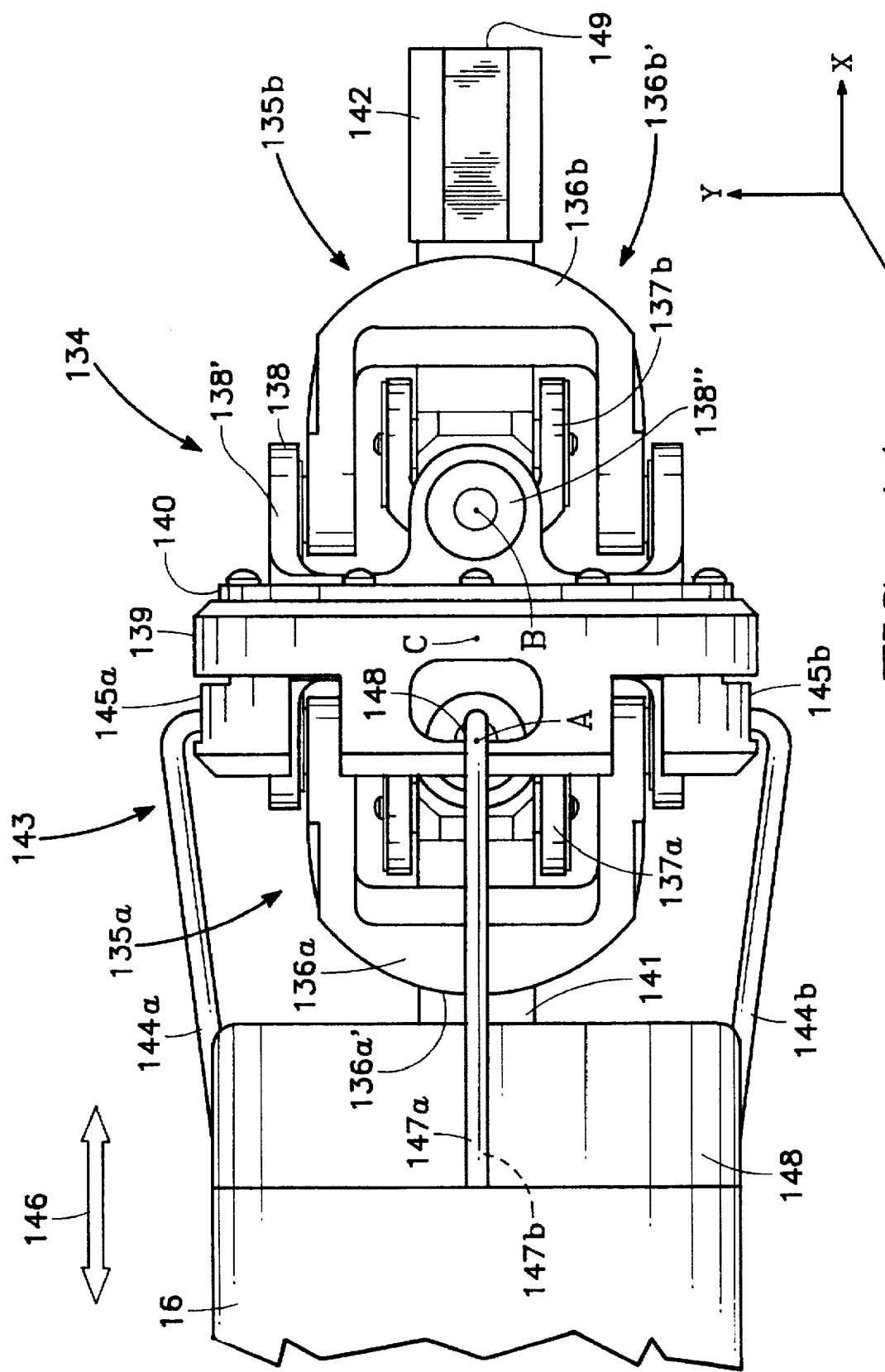
FIG. 11 illustrates the robot wrist of the present invention.

FIG. 11 illustrates the robot wrist of the present invention. The robot wrist 134 includes an input assembly 135A, an output assembly 135B, an inner housing 138, an outer housing 139, a middle housing 140, an input shaft 141, an output shaft 142, and a linkage assembly 143. The input and output assemblies 135A, 135B define a dual universal joint system that provides a three degree of freedom, singularity free, mechanically decoupled joint that operates in a full hemisphere of motion (up to 90 degrees in any direction).

The input assembly 135A includes an input outer universal 136A and an input inner universal 137A. Likewise, the output assembly 135B includes output outer and inner universals 136B, 137B which are counterparts of the input universals 136A, 137A. Each input universal 136A, 137A is symmetrical to its output universal 136B, 137B counterpart, respectively. The corresponding counterparts, defined by the symmetrical arrangement, are rotatably coupled to each other. The input and output universals are preferably coupled to each other by a tendon or cable arrangement (not shown) along a longitudinal axis parallel to an x axis.

Specifically, the universals are U-shaped and have arcuate faces on opposing input and output sides. The U-shaped configuration of the outer universals 136A, 136B define a respective slot 136A', 136B' for slidably receiving the input and output shafts 141, 142, respectively. The outer universals 136A, 136B terminate in a pair of the arcuate faces 136A", 136B". The arcuate faces 136A", 136B" have holes (not shown) for mounting the cables (not shown) between respective input and output outer universals 136A, 136B. Also, each inner universal 137A, 137B terminates in a pair of the arcuate faces (not shown) in a similar manner. The arcuate faces of the inner universals also have holes (not shown) for mounting the cables (not shown) between respective input and output inner universals 137A, 137B. The arcuate faces of the input universals 136A, 137A rotate on corresponding arcuate faces of the output universals 136B, 137B to define an instantaneous center C of rotation.

The tendon or cable coupling arrangement of each set of universals is functionally similar to the keying pulley/cable arrangement of FIGS. 4–8. For example, the input universals 136A, 137A are fixed to an input origin A and the output universals 136B, 137B are fixed to an output origin B. Each input and output origin, A, B, consists of two orthogonal axes parallel to the y and z axes. A set of outer universal cables (not shown) couples the input outer universal 136A to the output outer universal 136B. Likewise, a set of inner universal cables (not shown) couples the input inner universal 137A to the output inner universal 137B. The outer universal set of cables is aligned perpendicularly to the inner universal set of cables. The outer and inner universal cables are preloaded (in accordance with the discussion below in FIG. 12) in order to eliminate backlash in the y and z axes. The outer and inner universal cables are preferably steel cables.

Also, each pair of coupled universals rotate with respect to one another about the defined instantaneous center C of rotation, similar to the input and output keying pulley arrangement of FIGS. 4-8. However, the instantaneous center C of FIG. 11 has two axes of rotation, namely the y and z axes, unlike the instantaneous center 70 of FIGS. 4-8 which has only one axis or rotation. The rotational movements of the universals about their respective axes will be discussed below in detail.

The inner housing 138 has two halves, each being defined by two pairs of symmetrical crowns 138', 138". Each crown 138', 138" has four holes (not shown) centered on respective input and output origins A, B. The input universals 136A, 137A are rotatably mounted in the holes in each crown 138', 138" on the input origin A via bearings (not shown). The output universals 136B, 137B are rotatably mounted in the holes in each crown 138', 138" on the output origin B via bearings. When mounted in the inner housing 138, the input universals 136A, 137A rotate while constrained to the input origin A, and the output universals 136B, 137B rotate while constrained to the output origin B.

The output shaft 142 is rotatably coupled to the output inner universal 137B at the origin point B at the inner housing 138. The input shaft 141 is rotatably coupled to the input inner universal 136A at the input origin point A at the inner housing 138. This arrangement enables rotation of the input and output shafts 141, 142 about the y axis. The input and output shafts 141, 142 are coupled to the input and output inner universals 137A, 137B, respectively, with bearings (not shown). The inner universals 137A, 137B are rotatably coupled to the inner housing 138 at the z axis.

The output shaft 142 slides within the slot defined by the U-shaped configuration of the output outer universal 136B along the y axis. The input shaft 141 slides within the slot defined by the U-shaped configuration of the input outer universal 136A along y axis. This arrangement enables the input shaft 141 to rotate around the z axis and move the output inner universal 137B. Rotation of output shaft 142 around the y axis results in no movement of the output inner universal 137B. However, rotation of output shaft 142 around the y axis results in movement around the y axis of the output outer universal 136B.

The outer housing 139 is rotatably coupled to the middle housing 140 via a bearing assembly (not shown). The middle housing 140 is rotatably coupled to the inner housing 138 via a second bearing assembly (not shown). This enables rotation about the x axis between both the inner housing 138 and the middle housing 140 and the outer housing 139 and the middle housing 140. Thus, middle housing 140 rotates relative to inner housing 138 and outer housing 139.

The bearing assemblies are concentric and are nested inside one another. This concentric configuration allows both bearings to be assembled simultaneously, for easy assembly at any scale. Thus, the rotation of the input shaft 141 is transmitted through the housings and the universals to the output shaft 142 so that bidirectional rotation of the input shaft 141 results in bidirectional rotation of the output shaft 142. An actuator (not shown), which can be located in the forearm 16, rotates the input shaft 141 about the x axis (roll axis).

The linkage assembly 143 provides movement about the y and z axes of the output shaft 142 simultaneously. The linkage assembly 143 includes four links 144a, 144b, 147a, 147b, each having hooked ends (not shown). The links 144a, 144b are pivotally coupled about the y and z axes by a ball socket (not shown) at corresponding link attachments 145a, 145b, via the hooked ends. The link attachments 145a and 145b are rigidly attached to the middle housing 140. The links 147a and 147b are attached in a similar manner to the outer housing 139. Movement of the links 144a, 144b in the general direction of arrows 146 causes rotational movement of the inner housing 138 about the z axis of the wrist 134.

Movement of the links 147a, 147b in the general direction of arrows 146 results in rotational movement of the inner housing 138 about the y axis of the wrist 134. Any displacement of inner housing 138 relative to input shaft 141 is mirrored on output shaft 142 relative to inner housing 138. Hence, there is a 2:1 amplification of movement of output shaft 142 over inner housing 138. This enables a full hemisphere of motion.

The links 144a, 144b, 147a, and 147b are confined to move in the x-y plane. Each link 144a, 144b, 147a, 147b is connected to a corresponding linear carriage (not shown). The linear carriages are located within the forearm 16 and are fully symmetrical. Each linear carriage moves the corresponding link attached to it in a back and forth direction as indicated by arrow 146. The linear carriages are coupled and actuated by actuators (not shown) located in the forearm 16 or base. The linear carriages include a 2:1 force multiplier that counteracts a 2:1 force divider inherent to the kinematics of the system. Inclusion of the 2:1 force multiplier increases the stiffness of the wrist 134 by a factor of four. Corresponding linear carriages actuate links 144a and 147a in opposition to links 144b and 147b in order to actuate the z and y axes, respectively. Also, the linkages inherently preload one another, thereby eliminating their source of backlash.

The wrist 134 of the present invention provides movement about the x, y, and z axes simultaneously. The wrist 134 provides up to 180 degrees of motion about the y and z axes for the output shaft 142. The input shaft 141 is bidirectionally rotatable 360 degrees simultaneous with movement about the y and z axes. Thus, the work envelope of the wrist is a full hemisphere of motion.

An end cap 148 guides and positions the input shaft 141 and links 144a, 144b, 147a, 147b within the forearm 16. The input shaft 141 can be rotated inside the forearm within a ring bearing (not shown). The input shaft 141 can be coupled to a pulley assembly (not shown) within the forearm 16. This pulley assembly can be coupled to an actuator (not shown) located either within the forearm 16 or in the actuator base of FIG. 1. The actuator would transmit movement to the pulley assembly in order to move the input shaft 141.

The output shaft 142 has an end effector 149 for holding all types of tools (not shown). Circuitry can be routed through the arm to provide power to tools coupled to the end effector 149 that require electrical or pneumatic power. Also, the tendon or cable-driven arrangement (in accordance with the antibacklash scheme described below in detail) negates backlash in two of the three axes. In addition, the wrist 134 of the present invention has low stiction, high stiffness, and high strength-to-weight ratio.

For microsurgical applications, the wrist 134 can be approximately one inch in diameter, weigh approximately three ounces, and have a payload of about three inch-pounds. This allows the wrist 134 of the present invention to sustain a high work volume, while being lightweight, compact, and miniature in size.

ANTIBACKLASH MECHANISM

FIG. 12 illustrates the antibacklash mechanism of the present invention incorporated in the actuator base 28 of FIG. 1. The antibacklash mechanism 154 can be used with the joints of FIGS. 2–11 to overcome the problems of conventional antibacklash schemes. The antibacklash mechanism of the present invention is incorporated in the robot manipulator between the actuators, such as motors 156 at the actuator base, and an output 157 or the device to be actuated, such as the output link 62 of FIG. 5 of a particular joint.

The antibacklash mechanism 154 is a multiple stage device not limited to any particular number of stages. The antibacklash mechanism 154 utilizes a drivetrain system 158 with drive components such as gears, belts, and/or cables. FIG. 12 illustrates the antibacklash mechanism 154 having three stages 160, 162, and 164 with a pair of gears 166 and 168 and 170 and 172 at the first 160 and second stages 162, respectively.

Two independent transmission paths, defined by the gears 166, 182, 170, and 168, 184, 172, are formed as two identical geartrains in parallel for each drive. For example, a given joint's motor 156 would have one spur pinion 178 on its shaft 180 which would engage with two independent gears 166 and 168 of the first stage 160. The two independent transmission paths are mechanically coupled only at an input, such as the motor 156, and an output, such as an actuation pulley located on a particular joint.

The first and second stage gears 166 and 168 are free to rotate independent of each other, respectively. The pinion 178 on the motor 156 at the input drives both of the independent first stage gears 166 and 168 to complete a first stage 160 reduction. Two second stage 162 pinions 182 and 184 are rigidly attached to each of the first stage gears 166 and 168, for example on a gear shaft. The two second stage 162 pinions 182 and 184 drive the two independent second stage gears 170 and 172, thus completing the second stage 162 reduction (additional gear stages can be used).

Each of the second stage gears 170 and 172 drives an independent actuation drum or tendon spool 186 and 188 on a common shaft. Two cables 190 and 192, each attached to one of the spools 188 and 186, terminate on the output, which can be for example the actuation pulleys 106 and 108 of FIGS. 4–11. The cables 190 and 192 actuate the particular joint, thereby completing the third stage 164 and completing a dual drive system 174 and 176. Thus, with this arrangement, the only common points between the dual drive system 174 and 176 are at an origination at the input 156 (i.e. the motor 156) and the termination at the output 157 (i.e. the actuation pulleys 106 and 108 at the joint).

This dual drive arrangement allows for cable tensioning, eliminates backlash, and maximizes mechanical efficiency. Hence, from this feature, one of the advantages of the antibacklash mechanism of the present invention is convenient preloading of the gear stages 160, 162, and 164 to eliminate backlash. The dual drivetrain system is preloaded by first disengaging the motor 156 from the first stage 160 gears 166 and 168 so that the two gears 166 and 168 can be counter-rotated relative to one another. This counter-relation preloads the cables 190 and 192 to the desired tension. This rotation passes from stage to stage until all the cables become tensioned. When the desired preload tension is achieved, the motor 156 is simply re-engaged and the preload is locked.

Also, by disengaging the motor 156, the two drivetrains 174 and 176 can be reloaded relative to one another if necessary. In addition, since the preload is passed from one stage to the next stage, the value of the preload is proportional to any gear ratios between the stages 160, 162, and 164. Moreover, an optimum preload is achieved automatically in all the stages 160, 162, and 164 simultaneously because the preloading is passed via the gearing from the input motor 156 to the output 157. This preload is transmitted throughout the entire dual drivetrains 174 and 176, thereby eliminating backlash in all drivetrains. Further, the preload is transmitted proportionately to the gear ratio for each stage, to optimize the preload for maximum mechanical efficiency, unlike the prior art where each stage is independently preloaded.

Thus, the antibacklash mechanism 154 of the present invention provides geartrains with zero backlash, convenient preload adjustment, preload adjustment of all stages simultaneously, and stage preload proportional to stage ratio to achieve maximum mechanical efficiency. Also, since the required gear ratio for the microsurgical robot manipulator described above is between the actuator and each joint, the antibacklash mechanism of FIG. 12 is global for all the joints and encompasses a wide range of ratios. In addition, for the cable-driven robot manipulator, the cable preload is adjustable to accommodate stretching over time.

DETAILED COMPONENTS OF THE MICROSURGICAL ROBOT MANIPULATOR

Figure 13:
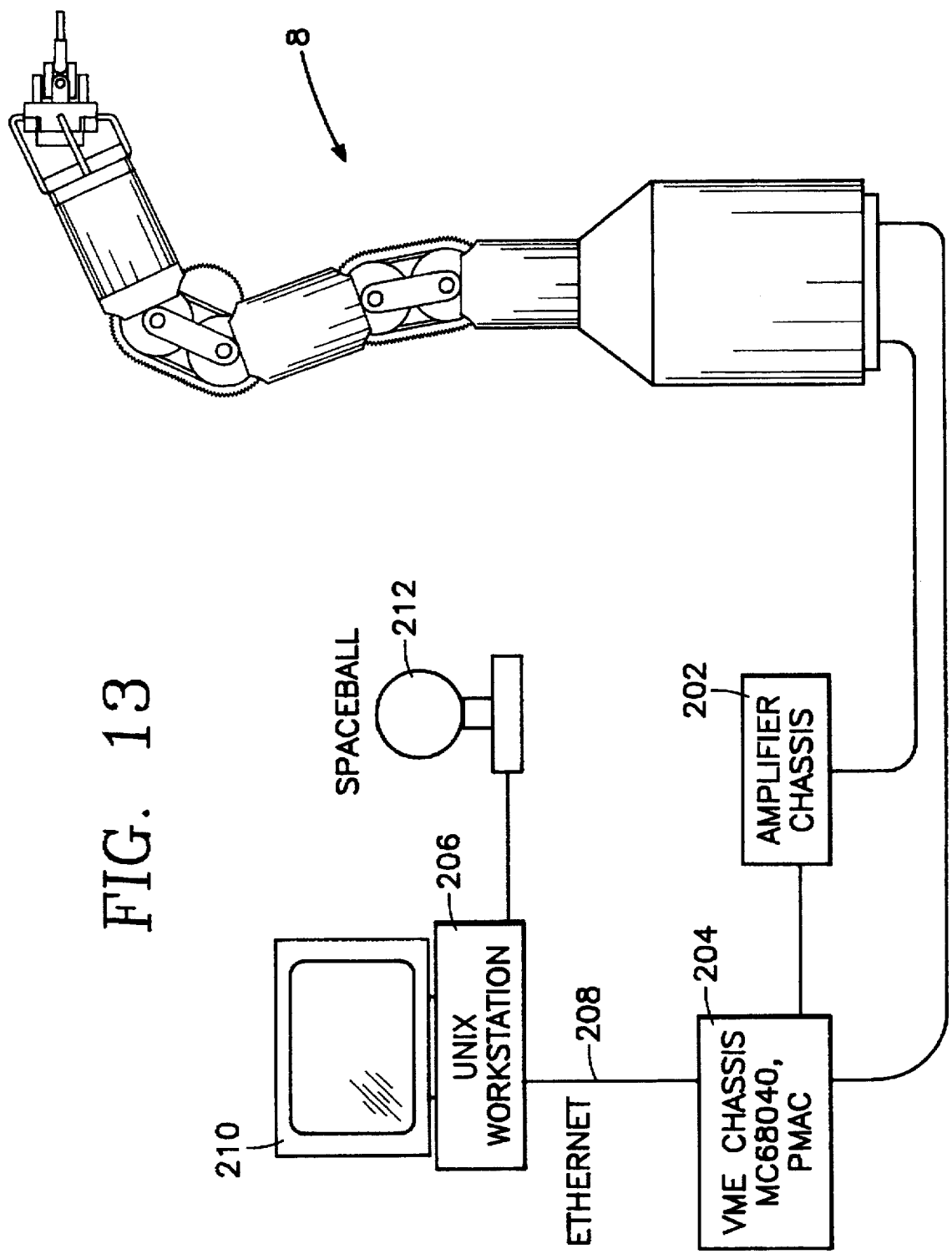
FIG. 13 illustrates an overview of the interaction between the sub-systems of the robot manipulator of the present invention.

FIG. 13 is the preferred embodiment illustrating an overview of the sub-systems of the present invention. The system architecture of the preferred embodiment of the present invention includes a slave robot manipulator 8 coupled to an amplifier chassis 202 which is coupled to a control chassis 204, such as a VME chassis. The VME chassis 204 is coupled to a workstation 206, such as a UNIX workstation via standard twisted pair Ethernet 208. The UNIX workstation 206 has a user interface 210 which can have a keyboard or other six degrees of freedom input device 212 for ease of control by a user.

Components of the robot manipulator are categorized into four sub-systems. The subsystems include the mechanical sub-system, the electronics sub-system, the servo-control sub-system, and the high-level software control sub-system. These sub-systems are described in detail in sections that follow.

Figure 14B:
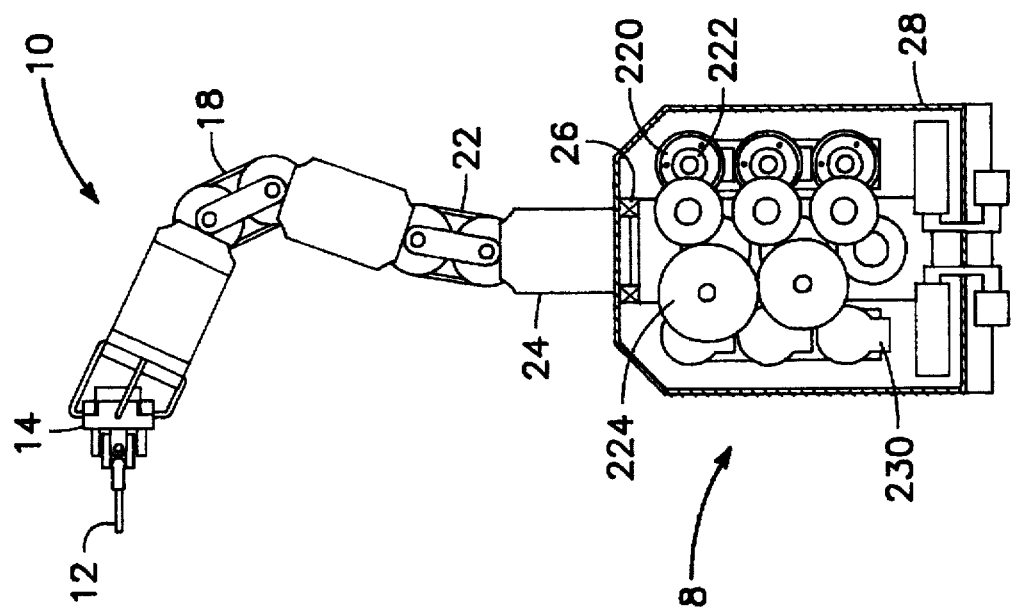
FIG. 14B illustrates a right side view of the mechanical sub-system of the robot manipulator of the present invention.
Figure 14A:
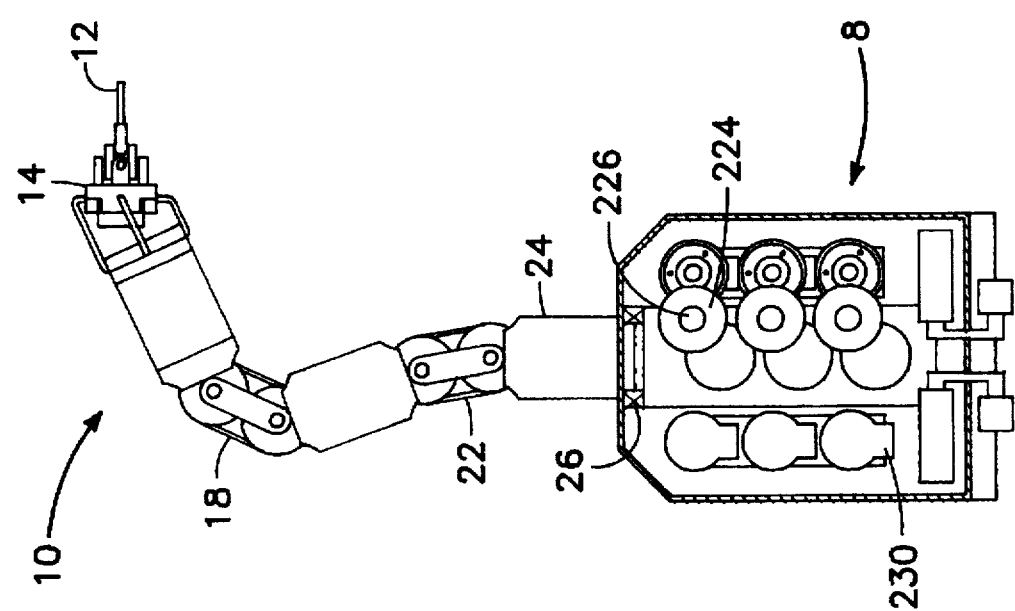
FIG. 14A illustrates a left side view of the mechanical sub-system of the robot manipulator of the present invention.

Mechanical Sub-system:

FIG. 14 is the preferred mechanical sub-system of the microsurgical robot manipulator 8 of the present invention. The mechanical sub-system consists of motors 220 with shafts 222, encoders (not shown), gears 224, pinions 226, bearings (not shown), cable spools (not shown) and other conventional components. The arm 10 of the robot 8 has tendons or cables, pulleys, and linkages located in the arm 10 and joints 14, 18, and 22 of the robot 8. These components mechanically operate the end effector 12 of the robot manipulator under computer control.

The robot manipulator 8 is preferably a compact six degree of freedom tendon-driven robot having very precise relative positioning capability (down to 10 microns) as well as a very high work volume. Physically, the arm 10 measures 2.5 cm. in diameter and is 24.6 cm long from the actuator base 28 to a tip of the end effector 12. The arm 10 is mounted to the actuator base 28 which can be a cylindrical base housing measuring 12.0 cm in diameter by 18.0 cm long. Also, the double-jointed decoupled cable or tendon-driven joints described in FIGS. 4–10 are used in the microsurgical robot manipulator 8. As shown in FIGS. 4–10, the joints 18 and 22 have very high ranges of motion, are double-jointed, and can pass any number of tendons through which are completely mechanically decoupled from the particular joint's motion.

Each degree of freedom of the robot is actuated by its own motor, such as a D.C. brushless motor encapsulated inside a sterile housing. Thus, there are six motors 220 (six degrees of freedom), three for the wrist joint 14, one for elbow joint 18, one for the shoulder joint 22, and one for the torso joint 26, which rotates the shoulder 24 about the actuator 28 or torso. The motors 220 are coupled to the gears 224 directly or via the pinions 226 for operating the gears 224. Preferably, the gears 224 and pinions are spur gears to define spur drivetrains. Although the number of gears 224 and pinions 226 to be used can vary with different design considerations, motor 220, pinion 226, and gear 224 configurations of the present invention are preferably in accordance with the novel antibacklash system described in detail in FIG. 12 above.

Each motor 220 is equipped with an optical encoder (not shown) on its shaft 222 for position sensing. The optical encoders preferably have 512 lines per revolution and produce outputs of 2048 counts per revolution. Since the smallest incremental movement during microsurgery is approximately 10 microns, 10 encoder counts is the minimum desirable incremental movement. As a result, one encoder count corresponds to one micron movement at the tip of the end effector 12. Based on the above dimensions and geometry of the preferred robot arm 10, the minimum required gear ratio for the wrist joint 14 is approximately 60:1, 300:1 for the elbow joint 18, and approximately 550:1 for both the torso 26 and shoulder 22 joints.

The gear reduction based on the tendons for each joint can be accomplished as described above in FIGS. 4–8. Preferably, the gear reduction is approximately 2.5:1 in the torso joint 26, wrist pitch, and wrist yaw axes (see FIG. 11), and approximately 1.5:1 in the shoulder 22 and elbow 18 joints, and the wrist roll axes (see FIG. 11). In addition, the robot has multi-stage spur drivetrain gear reductions based on the multi-stage gearing arrangement in the antibacklash scheme of FIG. 12 described above in detail.

The wrist pitch, yaw, and roll axes all have two-stage spur reductions of approximately 37:1, making the total reduction ratios approximately 92:1 (2.5 tendon gear reduction multiplied by 37 multi-stage gear reduction) for the wrist pitch and wrist yaw axes and approximately 60:1 (1.5 tendon gear reduction multiplied by 37 multi-stage gear reduction) for the roll axis. Also, the torso 26 and elbow 18 joints all have three-stage spur reductions of about 269:1, whereas the shoulder joint 22 has a three-stage reduction of about 411:1. The resulting total reduction ratios are approximately 667:1, 614:1, and 370:1 for the torso 26, shoulder 22, and elbow joints 18, respectively.

The microsurgical robot 8 of the present invention can be autoclaved for sterilization. Since the motors 220 and optical encoders are not capable of surviving such an environment, these components are removably attached within the actuator base 28. The motors 220 and optical encoders can be removed prior to sterilization and reinstalled afterwards. The motors 220 are removably attached on two mounting blocks 230 within the actuator base 28 on alignment pins (not shown). Each mounting block 230 contains three motors. The motors 220 are coupled to an electrical power source (not shown) via an electrical connector (not shown). The housing of the actuator base 28 tightly encloses the base 28 with screw mounts (not shown) or quick-release latches (not shown).

The joints 14, 18, and 22 of the microsurgical robot require high stiffness. Thus, relatively larger diameter tendon cables with short path lengths are used as described in FIGS. 4–8 above. Also, low stiction (stick/slip characteristic) is needed to achieve precise motions, especially since the optical encoder position sensors are in the robot's 8 base 28. Low stiction is accomplished by using precision ball bearings (not shown) in every rotating location, such as in all of the pulleys, joint axes, and drive shafts, to eliminate metal-to-metal sliding contact.

Figure 15:
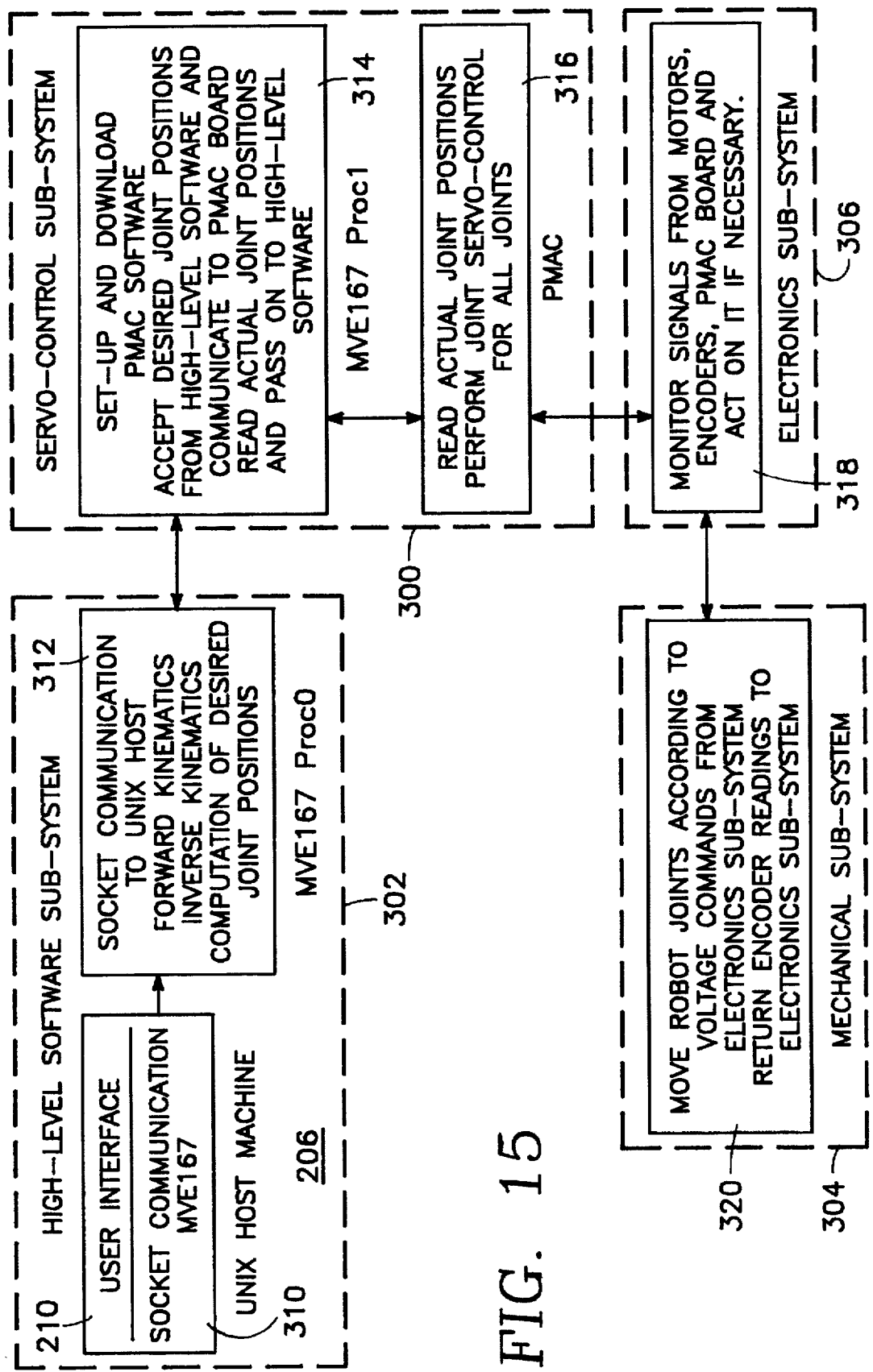
FIG. 15 is a block diagram illustrating the interaction of the high-level control software and servo-control sub-systems with the mechanical and electronic sub-systems of the present invention.

Servo-control and High-level Software Sub-systems:

FIG. 15 is a block diagram illustrating the interaction of the servo-control sub-system 300 and the high-level software sub-system 302 with the mechanical and electronic sub-systems 304, 306 of the present invention. The servo-control sub-system 300 is partly hardware and partly software. Referring to FIG. 15 with FIG. 13, the relevant hardware components of the servo-control sub-system are amplifier cards (not shown) within the amplifier box 202, and controller boards (not shown), which can be Delta Tau Data Systems, Inc.'s PMAC board and two MVMEP167 boards, Proc0 and Proc1, on the VME chassis 204.

Software runs under an operating environment, such as VxWorks operating environment, on the MVME167 boards of the VME chassis 204 to perform certain functions. These functions include setting-up control parameters and running a servo-loop on the PMAC board to control the six motors 220, implementing communication between the MVME167 and PMAC boards, initializing the servo-control system and communicating with the electronics sub-system, and communicating with a high-level software sub-system. The high-level software sub-system resides on the UNIX workstation 206 and on the Proc0 board on the VME chassis 204. The high-level software sub-system 302 is connected to the user interface 210 and controls initialization of the software and hardware. Also, a communication system 310, which can be based on the UNIX socket protocol or Real-time Innovation, Inc.'s Network Data Delivery System (NDDS), connects the UNIX host to Proc0. This high-level software sub-system 302 implements a number of demonstration modes 312 of robot control and computes forward and inverse kinematics and desired joint positions.

A first servo-control software module 314 is implemented on Proc1, is coupled to the high-level software through the backplane of the VME chassis with the use of shared memory between Proc0 and Proc1. The first module 314 configures and downloads PMAC software, accepts the desired joint positions from the high-level software and communicates these positions to the PMAC board, and reads the actual joint positions and sends these positions to the high-level software. Also, a second module 316 of the servo-control sub-system performs joint servo-control for all the joints based on the reading of the actual joint positions.

The electronics sub-system 306 is coupled to the servo-control sub-system 300 and will be discussed below. The mechanical sub-system 304 is coupled to the electronics sub-system 306 and has a mode 320 which moves robot joints according to voltage commands from the electronics sub-system and returns encoder readings to the electronics subsystem.

Robot Kinematic Algorithms

The present invention uses kinematic algorithms for computation of the forward and inverse kinematics of the robot. Kinematic algorithms are described in U.S. Pat. No. 5,303,384, the disclosure of which is incorporated by reference in its entirety. The forward kinematics computation refers to the determination of the tip position and orientation given known joint angle positions of the robot. The inverse kinematics is the determination of the joint angle positions given a desired tip position and orientation.

Specifically, the robot is modeled as a 10-joint serial linkage due to the unique shoulder and elbow joint design that has two points of rotation and the wrist design that also has a double rotation transformation similar to a universal joint for both the y and z axes degrees of freedom. There are a total of 10 transformation matrices, each mapping a coordinate frame from a base coordinate to the first joint, from each succeeding joint to the next, and finally to the tip of the robot. Since the robot has three degrees of freedom in the decoupled joints (torso, shoulder and elbow joints) and three degrees of freedom in the wrist joint, there are a total of 10 transformations.

The forward kinematic algorithm computes an attitude matrix of a coordinate system attached to the tip of the manipulator, as well as the location of the tip. The tip is defined as a distance 1(−1) away from the base of the output shaft 142 of FIG. 11, measured along the direction of the output shaft 142. The algorithm starts with pre-defined equations that are functions of joint angles of the robot for all elements of the 10 matrices. The forward kinematics starts with computing values of the elements of the matrices given current positions of the joint angles of the robot. Next, a loop is executed that determines the position and orientation of each succeeding joint coordinate frame. Quantitatively, the steps taken in the computation of the forward kinematics are:

Step 1:
Compute A(k) matrix elements given robot joint angles
Step 2:
Initialize the matrix S and the vector r, where: S=U; and r=0
Step 3:
Perform the following computation

```
for k = 0 until k = 9 {
    S = A*(k) S
    r = A*(k) r + 1(k) z
    k = k + 1
}
``` where S is a 3 by 3 matrix that accumulates the new orientation of the joint coordinate frame, r is a 3 by 1 vector that accumulates the position of the joint coordinate frame in a base referenced coordinate frame, U is a 3 by 3 unit matrix, z is the 3 by 1 vector with elements {0, 0, 1}, l(k) is the link length between joint k and joint k−1, and A*(k) is the coordinate transformation matrix of the k-th joint. The derivation of the A*(k) matrices for the torso, shoulder, elbow and wrist roll joints is trivial. The pitch and yaw joints, however, require a non-linear transformation from the actuator position to the modeled joint angle. A closed form method is derived for this transformation based on the measured pitch and yaw actuator positions.

The inverse kinematics is computed by solving the following equation:

$$v = Jw$$

where w is the modeled joint displacement vector, v is the tip displacement vector and J is the Jacobian matrix. The vector v is known and it is desired to determine the vector w. The computation of the of the vector w is performed with the following algorithm.

Step 1:
Compute P(k) matrix elements given the robot joint angles
Step 2:
Set-up H(k) vectors
Step 3:
Transform v to a tip based coordinate frame
Step 4:
Perform the following computation

```
for i = 5 until i = 0 {
    V = 0
    for j = 9 until j = 0 {
        T = P(k + 1) V
        if (
            ((i = 5) and (j = 9))
            or ((i = 4) and ((j = 8) or (j = 7)))
            or ((i = 3) and ((j = 6) or (j = 5)))
            or ((i = 2) and (j = 4))
            or ((i = 0) and ((j = 3) or (j = 0)))
            or ((i = 1) and ((j = 2) or (j = 1)))
        ) {
            V = T H(j)
        }
        else {
            V = T
        }
        j = j − 1
    }
    for j = 0 until j = 5 {
        J[i, 5 − j] = V[j]
        j = j + 1
    }
    i = i − 1
}
```

Step 5:
Perform the LU decomposition of the matrix J and then perform back substitution with the vector v to determine the vector w. In the computation above, P(k) are 6 by 6 transition matrices for each joint, H(k) are 6 by 1 vectors indicating the axis of rotation of the respective joint, V is a 6 by 1 temporary accumulation vector, T is a temporary 6 by 6 matrix and J is the 6 by 6 Jacobian matrix of the robot. The pitch and yaw axes joint displacements then need to be transformed to actuator joint displacements through a non-linear transformation. The conversion of the remaining joints to actuator velocities involve a linear transformation.

Figure 16:
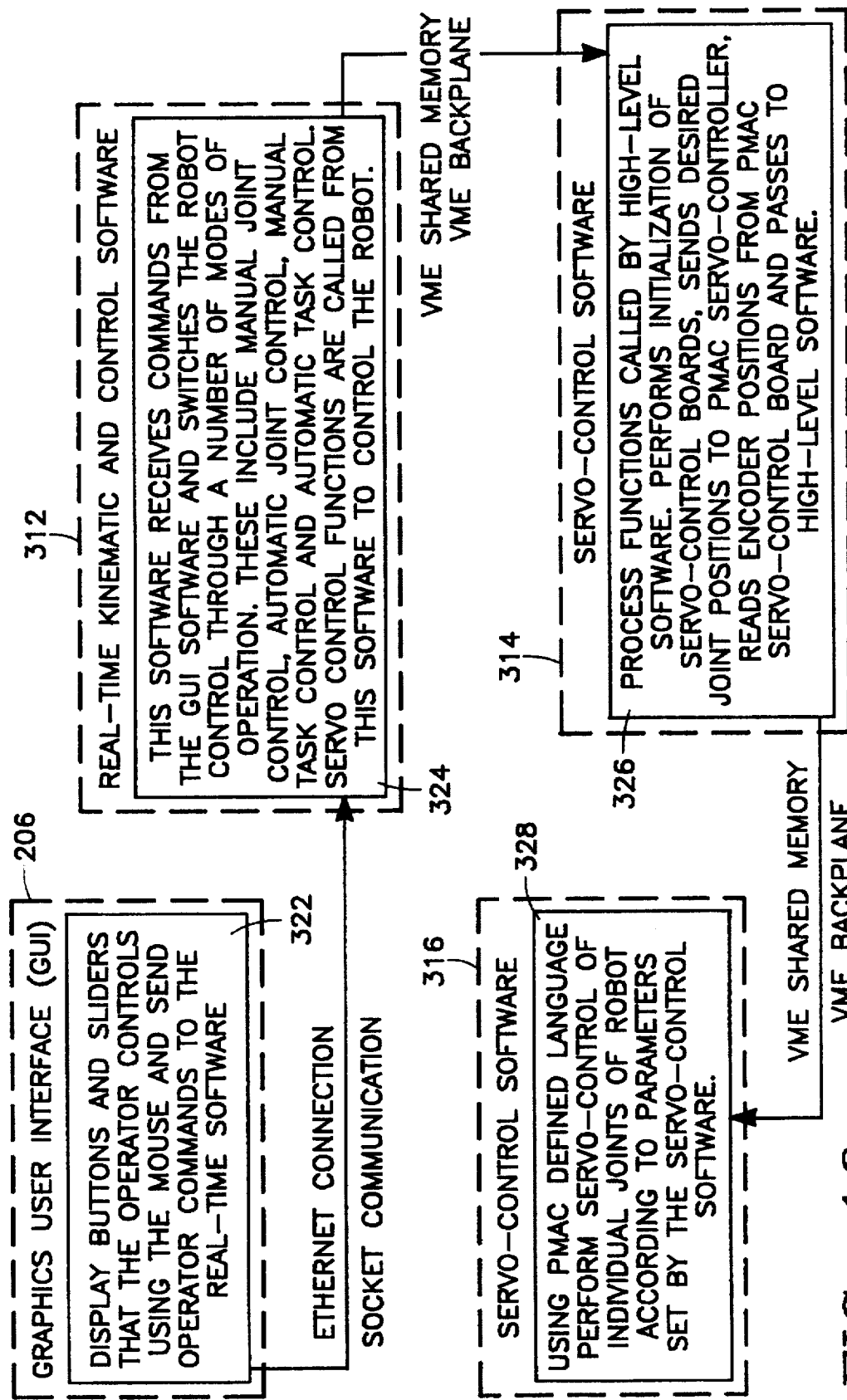
FIG. 16 is a block diagram illustrating an overview of the high-level software architecture.

High-level Software Sub-system:

FIG. 16 is a block diagram illustrating an overview of the high-level software architecture. The high-level software has two components, graphics user interface software 322 and real-time kinematic and control software 324. The graphics user interface software 322 produces a graphics user interface (GUI) residing on the Unix host machine 206. The GUI interacts with the user and communicates user input to the MVME167 Proc0 board 312 through the socket interface. The UNIX workstation 206 is coupled to the MVME167 Proc0 board in the VME chassis through, for example, an Ethernet connection, as described above in FIG. 15. The real-time kinematic and control software 324 is implemented on the MVME167 Proc0 board 312.

Specifically, the GUI displays buttons and sliders that the user controls using an input device, such as a mouse. The two components 322, 324 have input and ouput communication channels implemented for message passing between the two components 322, 324. The software could be, for example, using the UNIX socket utility or Real-time Innovation, Inc.'s NDDS.

The real-time kinematic control software 324 of the high-level control software runs on the MVME167 Proc0 board 312 in the VME chassis and receives user commands input to the GUI software module 322 in real-time. Also, the real-time kinematic control software 324 switches control of the robot through a number of modes of operation. These modes of operation include manual joint control, automatic joint control, manual Cartesian control, and automatic Cartesian control. In all of these modes, servo control functions are called from the real-time software to control the robot.

A servo-control software module 326 runs on the MVME167 Proc1 board 314 in the VME chassis. The servo-control software module 326 processes functions called by the high-level software, performs initialization of servo-control boards, sends desired joint positions to the PMAC servo-controller, reads encoder positions from PMAC servo-controlled board, and sends the information back to the high-level software. A servo-controller 328 resident on the PMAC boards 316 performs servo-control of individual joints of the robot according to parameters set by the servo-control software module. It should be noted that the servo-control software module and the servo-controller on the PMAC boards can have shared memory through the VME backplane.

Figure 17:
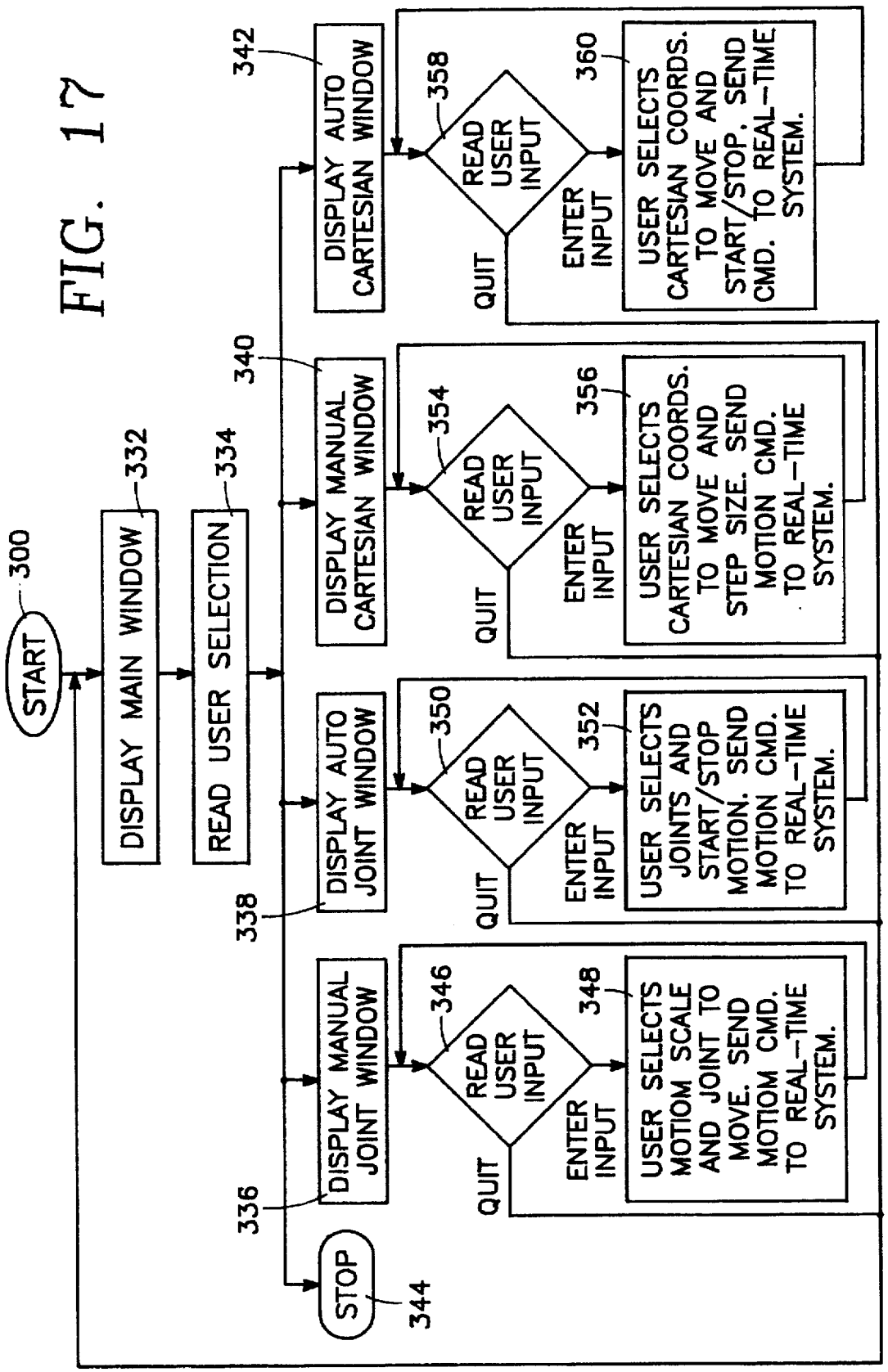
FIG. 17 is a block diagram illustrating the details of the graphics user interface (GUI) software of the high-level software architecture.

FIG. 17 is a block diagram illustrating the details of the GUI software 322 of the high-level software architecture. The GUI software 322 can be implemented, for example, using X Windows/Motif and Tcl/Tk or the Widget creation libraries (Wcl).

In an initialization procedure 330, the program first establishes the communication channel to the software running on the MVME167 Proc0 board for sending user commands to the control system. Next, the parameters within the program are initialized and a main display window 332 is displayed on the screen of the UNIX workstation. The display window 332 can have a graphics menu with user selections. The user's selection is then read 334 by the GUI software. The selections include a manual joint control command 336, a autonomous joint control command 338, a manual Cartesian control command 340, a autonomous Cartesian control command 342, and an exit or stop command 344 to terminate the session. Each selection for robot control results in a procedure being executed.

The manual joint control command 336 allows joint space control of the robot manually with the mouse input device on the UNIX workstation. The software reads 346 user input for the manual joint control command 336. The user is able to move 348 each joint in steps either incrementing or decrementing the joint position by clicking on appropriate buttons of the new display. The step size is scalable using the sliders on the display. The joint space control can have its own window on the display.

The autonomous joint control command 338 implements a demonstration mode to show the robot exercising its joints. Upon selection of the autonomous joint control command from the main display window, a new window appears on the display. User input is then read 350 by the software. The user can select 352 one or more joints to be exercised. Also, each of the selected joints can be moved in a sinusoidal motion. The frequency of the motion is different for each of the joints. In addition, the user can stop the motion at any time. The user can also return to the main menu window at any time.

The manual Cartesian control command 340 allows the user to control the robot in Cartesian space. Upon selection of the manual Cartesian control command from the main display window, a new window appears on the display. User input is then read 354 by the software. The user selects Cartesian coordinates 356 to incrementally or decrementally move the robot tip linearly along X, Y, and Z axes and to rotate the robot tip about the X, Y, and Z axes. The input is communicated to the software through an input device, such a mouse or a 6 degrees-of-freedom joystick or a spaceball (6 degrees-of-freedom spaceball). A slider on the display is used to change the motion scaling of the robot.

The autonomous Cartesian control command 342 is a demonstration mode for showing robot movement autonomously in Cartesian space. Upon selection of the autonomous Cartesian control command from the main display window, a new window appears on the display. User input is then read 358 by the software. The user selects Cartesian coordinates 360 in one or more degrees-of-freedom for motion along the x, y, and z axes, and to rotate the robot tip about the x, y, and z axes. The robot can be set into sinusoidal motion for the selected degrees-of-freedom. The user can stop 344 the motion at any time. The user can also return to the main menu window 332 at any time.

There are two components to the real-time software. The components include a state transition controller (described in FIG. 18 below) and computation executions (described in FIGS. 19–24 below). These components may be implemented in a programming language, for example, C or C++ or more easily with a real-time software development environment, such as, Real-time Innovation Inc.'s Control Shell.

Figure 18:
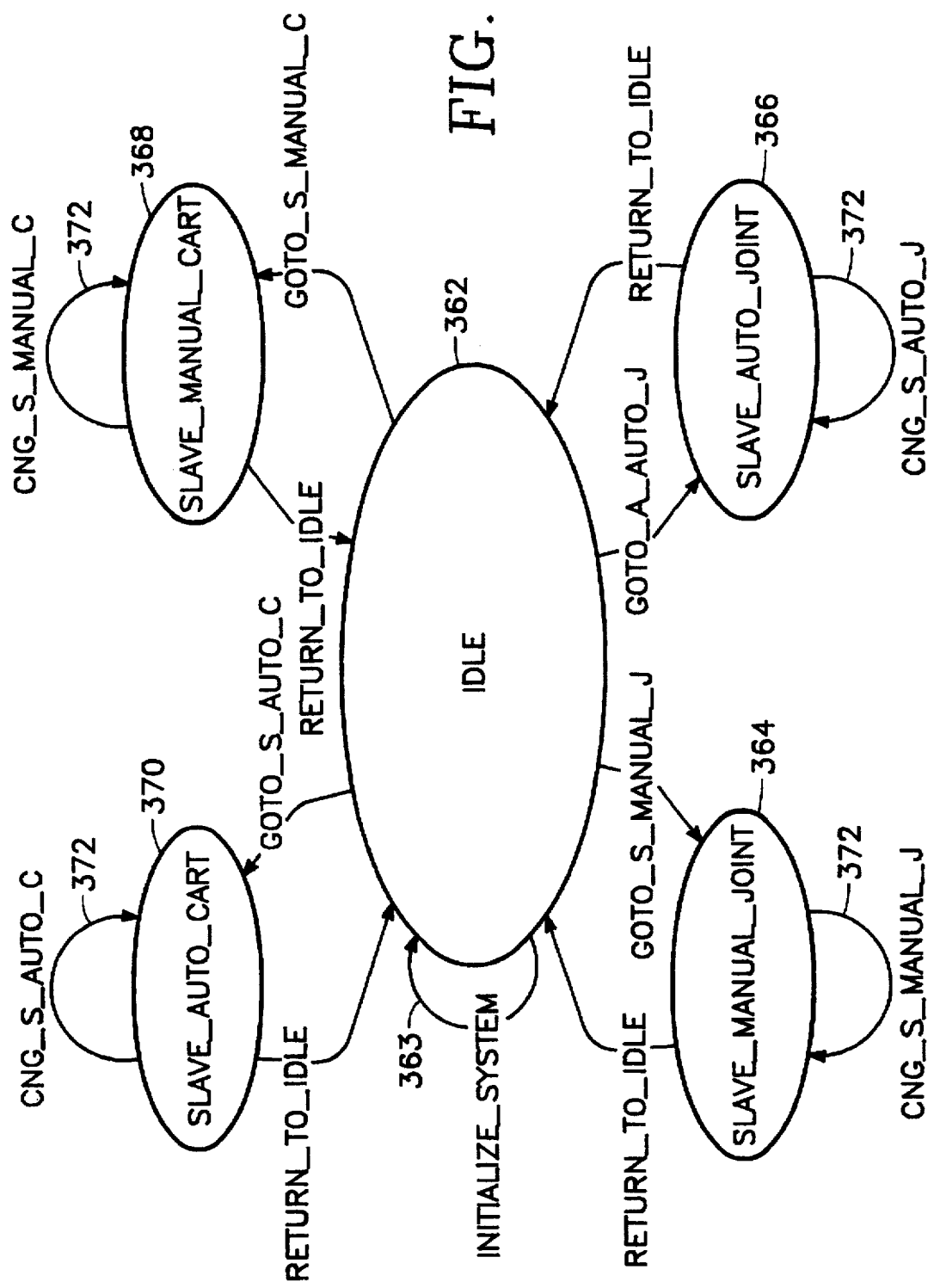
FIG. 18 is a block diagram illustrating the states and their possible transitions in the real-time high-level software architecture.

FIG. 18 is a block diagram illustrating states and their possible transitions of the state transition controller component of the real-time high-level software. The states implemented in the control of the slave robot are: an idle state 362, a manual joint control state 364, an autonomous joint control state 366, a manual Cartesian control state 368, and an autonomous Cartesian control state 370. When the system is initialized 363, the system returns to the idle state 362. Within each state, changes 372 can be made to accommodate a user's particular input. Transitions from one state to another are performed in response to messages from the GUI 322 of FIG. 16. For example, transitions may cause the system to change state or return to the same state. A state corresponds to a subset of software computational modules used to perform the computations for the state.

Figure 19:
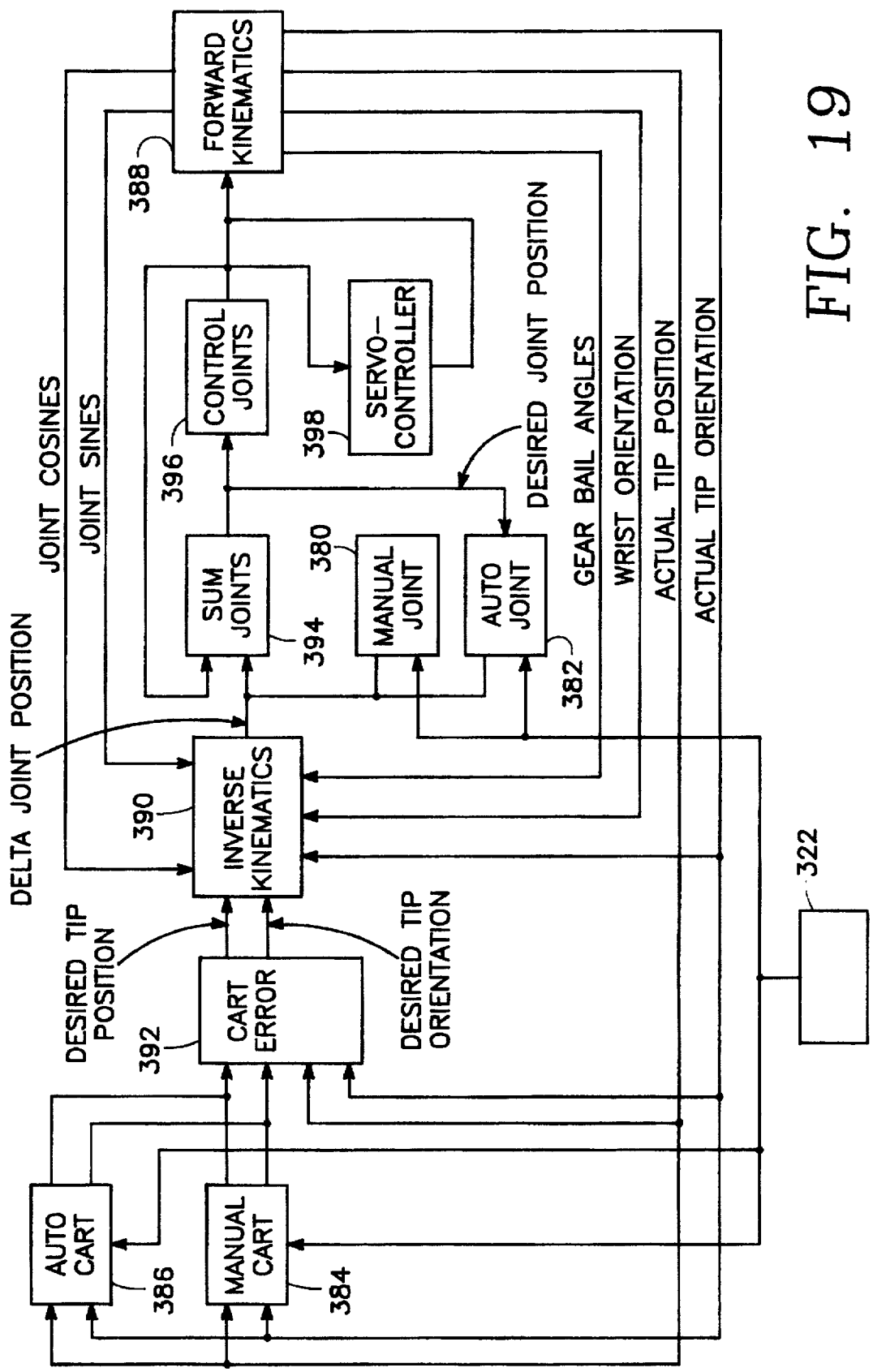
FIG. 19 is the total set of computational modules used for the slave robot and their data flow paths.

FIG. 19 is a block diagram illustrating a total set of computational modules of the computation execution component used for the slave robot and their data flow paths. State transitions between states cause a change in the data flow paths and the use of a different set of computational modules to be executed. State transitions back to the start state cause a change in the parameters of modules used in the state.

The real-time software 324 running on the MVME167 Proc0 board 312 of FIGS. 15 and 16 cycles continuously through the set of active modules that are connected by data paths. The robot has five states of control of the robot. Two of the states are Cartesian space control states that require computation of the forward and inverse kinematics of the robot arm. These computations were discussed in detail above. The architecture of the other three states is presented in the following sections. Messages sent from the GUI software 322 through the Ethernet communication channel (see FIG. 16) to the real time software 324 cause transitions or switching of the real-time software 324 between the five different states. Also, these messages cause the real-time software 324 to change parameters of the control states and return.

The computational modules include a manual joint module 380, an auto joint module 382, a manual cart (i.e., Cartesian) module 384, an auto cart module 386, a forward kinemat module 388, an inverse kinemat module 390, a cart error module 392, a sum joints module 394, a control joints module 396, and a servo-controller module 398.

The manual joint module 380 receives commands from the GUI software 322 of FIG. 16 through the state transition routine of FIG. 18 for joint angle changes. When active, the manual joint module 380 sends commands to the sum joints module 394 to change the position of each of the robot joints for this computation cycle and then returns to a zero joint change output.

The auto joint module 382 receives commands from the GUI software 322 of FIG. 16 through the state transition routine of FIG. 18 transition routine on starting, stopping and selecting combinations of joints for motion. When active, the auto joint module 382 sends commands to the sum joints module 394 to change the position of each of the robot joints for each cycle so that the selected robot joints start and continue or stop moving in a sinusoidal motion.

The control joints module 396 receives the desired set of joint angle positions from the sum joints module 394 to limit the joint angles sent to the servo-controller so that they are within a safe set of joint angle ranges. The servo-controller module 398 receives the set of joint angles from the control joints module 396 to control the robot. The servo-controller module 398 converts the joint angle positions from units of radians to units of encoder counts, then sends this set to the PMAC board so that the control loop in the PMAC will move the joints to this set of measurements. Also, the servo-controller module 398 reads the actual angle positions from the PMAC and converts them from units of encoder counts to units of radians. The set of actual joint positions determined by the servo-controller module 398 are sent to the forward kinemat module 388.

The forward kinemat module 388 receives the input from the control joints module 396 and the servo controller module 398 on the robot joint angles the robot link lengths. The forward kinemat module 388 computes the forward kinematics of the robot based on these inputs. The robot tip position vector, the robot tip orientation matrix, the robot joint angle sines, the robot joint angle cosines, the transformation matrix from robot wrist to tip, and the gear bail angles are determined from the computations of the forward kinemat module 388.

The robot joint angle sines, robot joint angle cosines, gear bail angles, and transformation matrix from robot wrist to tip are sent to the inverse kinemat module 390. The robot tip position vector is sent to the cart error module 392, manual cart module 384, and auto cart module 386. The robot tip orientation matrix is sent to the inverse kinemat module 390, cart error module 392, manual cart module 384, and auto cart module 386.

The inverse kinemat module 390 also receives the desired tip position and the desired tip orientation from the cart error module 392. The inverse kinemat module 390 computes the inverse kinematics of the robot based on these inputs. The change in the robot joint angles that result in the desired change in tip position and orientation are determined from the computations of the inverse kinemat module 390.

The sum joints module 394 receives the desired change in joint angle positions from either the inverse kinemat module 390, the manual joint module 380, or the auto joint module 382, depending which is active. Current control joint positions are received from the control joints module 396. The sum joints module 394 computes the sum of the desired change in joint angle positions and the current joint angle positions. The output of the sum joints module 394 is reset to the actual joint angle positions upon a change in transition. The sum joints module 394 then sends a new set of joint angle positions to the control joints module 396 to control the robot.

When active, the manual cart module 384 receives commands from the GUI software 322 of FIG. 16 through the state transition routine of FIG. 18 transition routine. The manual cart module 384 computes the change in the Cartesian position of the robot tip so that the commanded coordinate will move by the commanded step size. The manual cart module 384 changes the position of each of the Cartesian position and orientation of the robot tip for this computation cycle and then returns to zero the tip position and orientation change.

When active, the auto cart module 386 receives commands from the GUI software 322 of FIG. 16 through the state transition routine of FIG. 18 transition routine on starting, stopping and selecting combinations of tip coordinates for motion. The auto cart module 386 computes the change in the robot tip position and orientation so that the selected tip coordinates will move continuously in a sinusoidal fashion at different frequencies. The auto cart module 386 changes the position of each of the robot tip coordinates for each cycle so that the selected robot tip coordinates start and continue or stop moving in a sinusoidal motion.

In addition to receiving the actual tip position vector and the actual tip orientation vector, the cart error module 392 also receives the desired tip position vector and the desired tip orientation matrix from the either the manual or auto cart modules 384, 386, depending which is active. The cart error module 392 computes the difference between the desired tip position and the actual tip position and the difference between desired tip orientation and actual tip orientation based on these inputs. The cart error module 392 then sends the difference between desired and actual tip position and the difference between desired and actual tip orientation to the inverse kinemat module 390.

Figure 20:
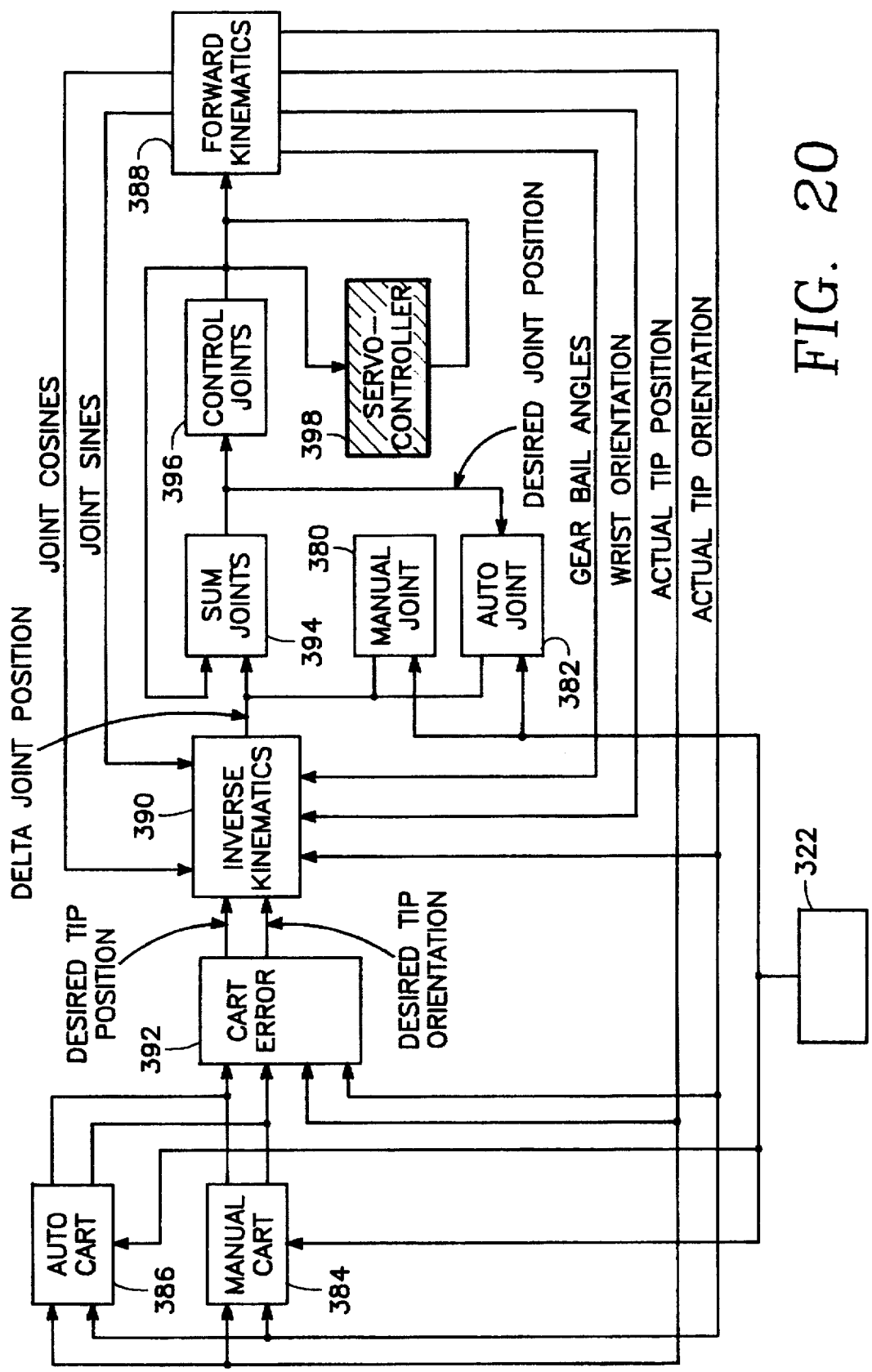
FIG. 20 is the only active module in the idle state is the servo controller.

FIG. 20 is a block diagram illustrating the idle state computational module. The active module is shaded and in the idle state is the servo controller module 398. The robot is controlled at its current position in the idle state. From the idle state, the system may transition to any other state or in an initialization transition, back to itself. The initialization transition resets the parameters of the servo-controller module 398.

Figure 21:
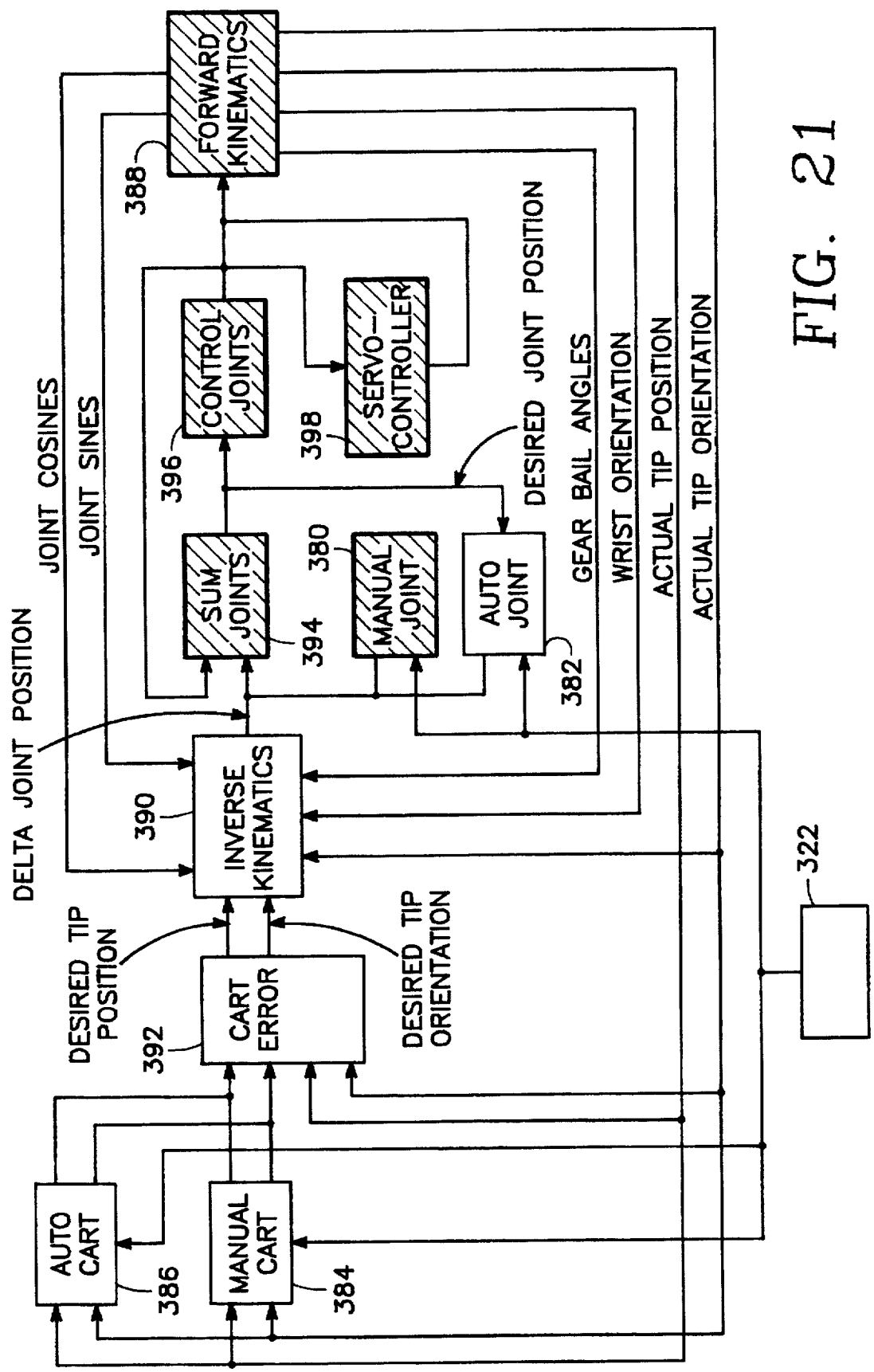
FIG. 21 is a block diagram illustrating the modules used in the manual joint space control state of the high-level software architecture.

FIG. 21 is a block diagram illustrating the modules used in the manual joint space control state of the high-level software architecture. The active modules are the manual joint module 380, the sum joints module 394, the control joints module 396, the forward kinemat module 388, and the servo-controller module 398. Transitions from this state either return the system to the idle state or change the parameters of the manual joint module 380 and return back to the manual joint control state. The parameters changed cause the module to momentarily signal its succeeding module for a change in a specified joint angle by a specified step size. The manual joint module 380 then continues to signal a zero step size for all joints. The result is that the robot will move one of its joints by the specified change then stop.

Figure 22:
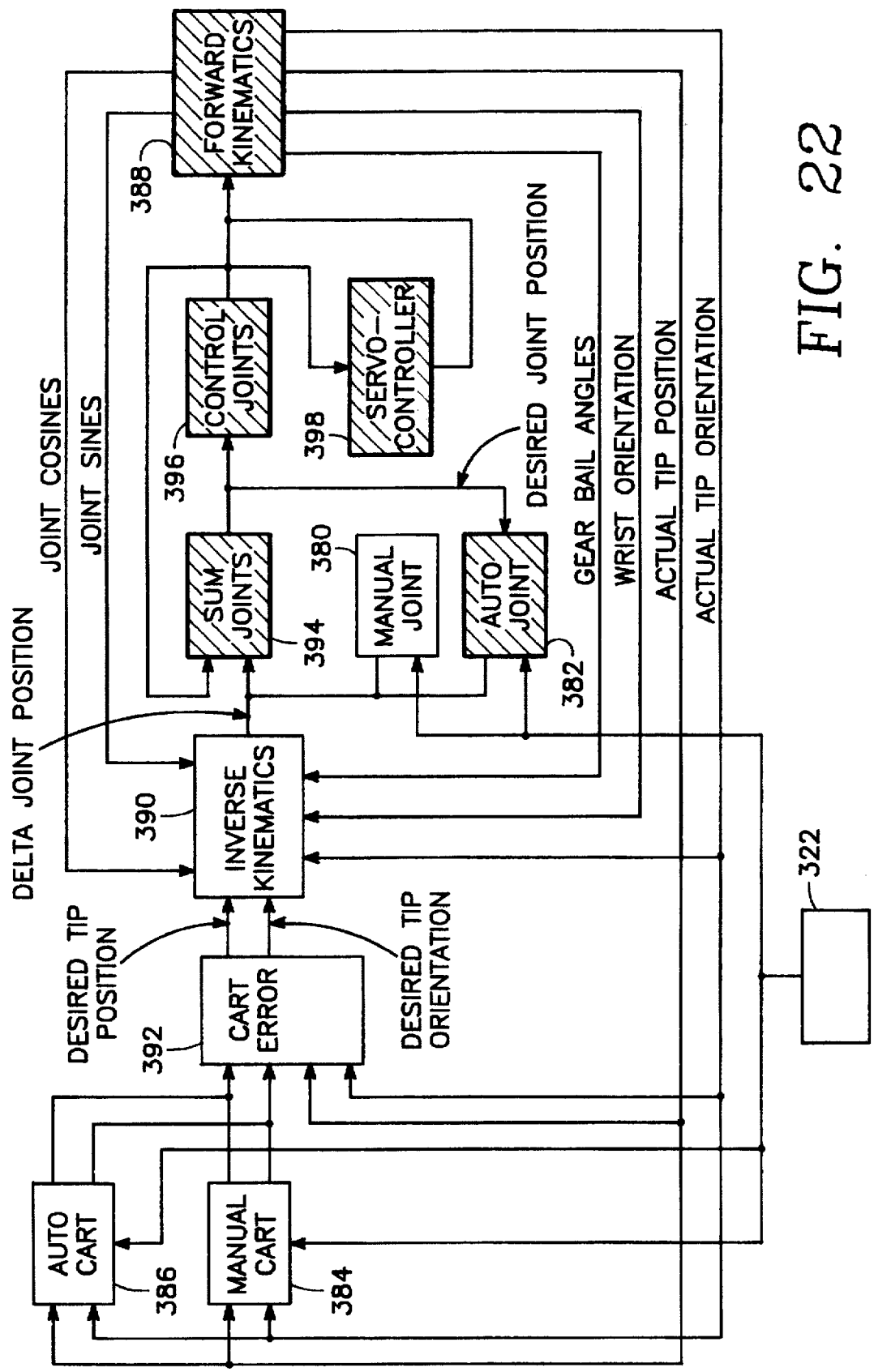
FIG. 22 shows the active modules for autonomous joint control.

FIG. 22 is a block diagram illustrating the autonomous joint control module. The active modules are the auto joint module 382, the sum joints module 394, the control joints module 396, the forward kinemat module 388, and the servo-controller module 398. In the autonomous joint control state, the robot moves selected joints in a sinusoidal motion at different frequencies. Referring to FIGS. 18 and 22, the state transitions for this state is a return to the idle state or a return to its current state with a change in parameters of the auto joint module. When a message for change of parameters of the autonomous joint control is received, the motion can be stopped, or started with a different set of joints set in motion.

Figure 23:
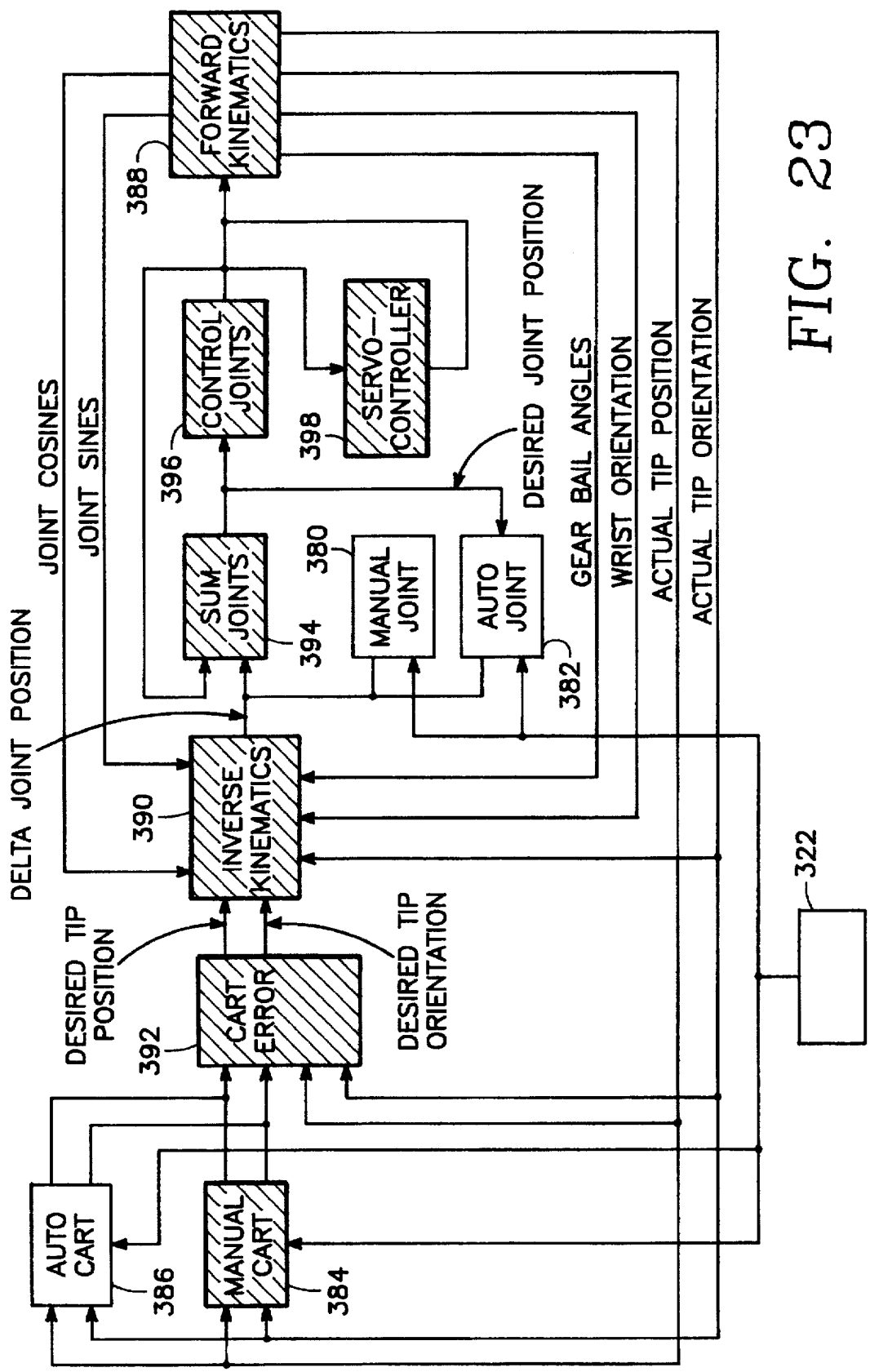
FIG. 23 is a block diagram illustrating manual Cartesian space control of the slave robot.

FIG. 23 is a block diagram illustrating the manual Cartesian space control module of the slave robot. The active modules are the manual cart module 384, the cart error module 392, the sum joints module 394, the control joints module 396, the forward kinemat module 388, the inverse kinemat module 390, and the servo-controller module 398. Referring to FIGS. 18 and 23, for manual Cartesian space control, a message from the user interface can switch the state to back to the idle state or back to the manual Cartesian space control state. In a switch back to the manual Cartesian control state, the user also specifies the Cartesian space coordinate to be moved and its step size. For manual Cartesian motion, the manual cart module 384 computes Cartesian positions by adding specific Cartesian position increments to the current position of the robot. The computed change in joint angles from the inverse kinematics module are summed with the current joint angles then sent to the joint servo controller for robot movement. Increments in the respective coordinates are computed so that the end effector moves along the selected coordinate.

Figure 24:
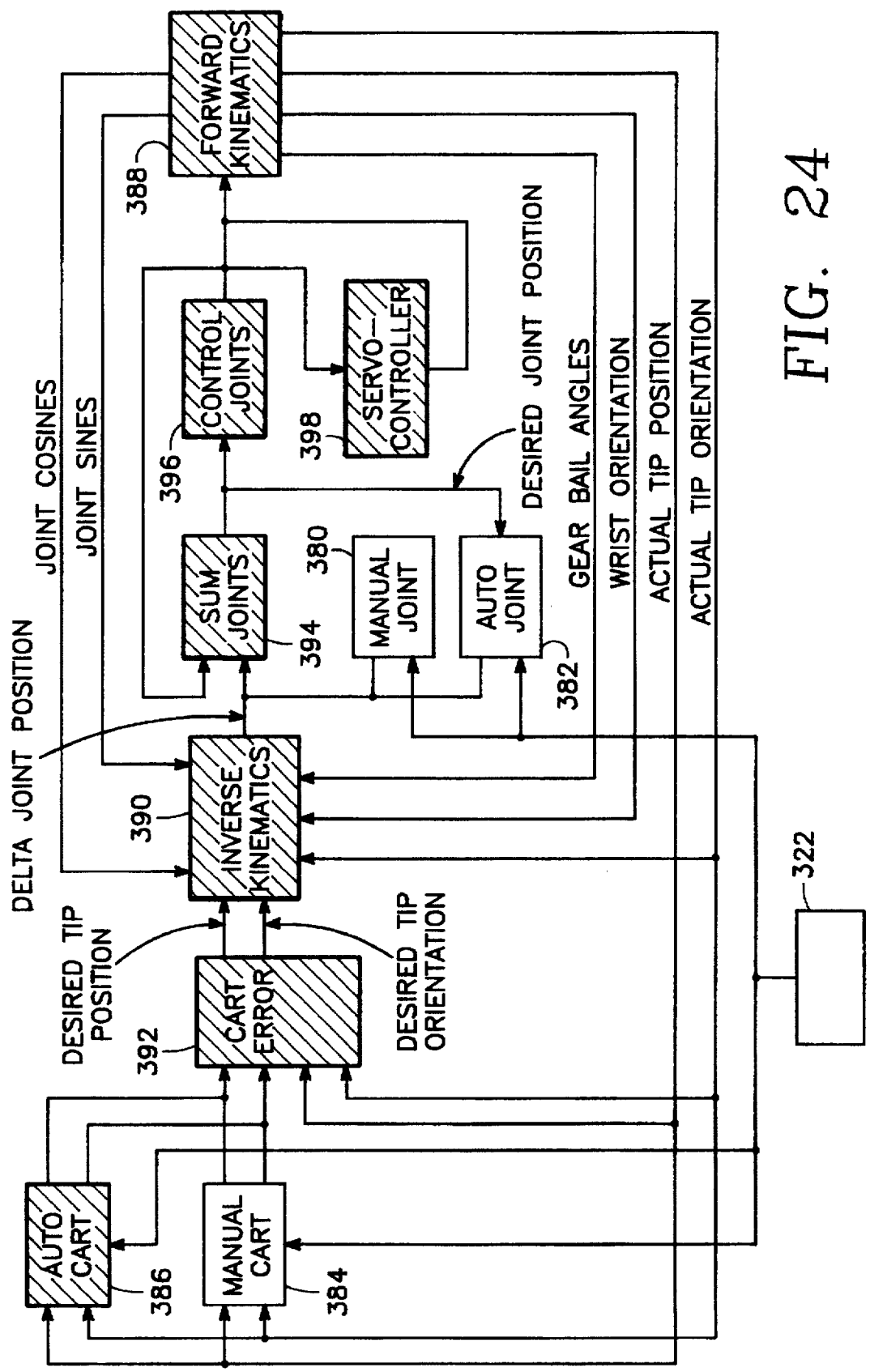
FIG. 24 shows the modules used in the autonomous Cartesian control state.

FIG. 24 is a block diagram illustrating the autonomous Cartesian control state module. The active modules are the auto cart module 386, the cart error module 392, the sum joints module 394, the control joints module 396, the forward kinemat module 388, the inverse kinemat module 390, and the servo-controller module 398. In this state, the robot moves its tip in a sinusoidal motion along specified Cartesian coordinates. Referring to FIG. 18 and FIG. 24, the transitions available from this state are a return to the idle state or back to this state with some change in parameters in the auto cart module 386. A change in parameters of the auto cart module 386 cause either the motion of the robot to stop or to start with a new set of Cartesian coordinates set in motion. The corresponding joint positions are computed using inverse kinematics. The computed joint angles are sent to the joint servo controller for robot movement.

Robot Operation:

The robot is started by powering the VME chassis, thereby initiating the down-loading and running of software on the MVME167 boards and PMAC boards. The GUI program is then run on the UNIX host machine to start-up the graphics user interface and establish communication between the UNIX host and the MVME167 board using the NDDS facility. A procedure of phasing the motors is performed after the boot-up sequence and powering up the amplifier chassis. The system is then ready for demonstrating the various control modes available. During the demonstration modes of control, the high-level software computes the desired joint positions for the robot. These are fed to the PMAC board by the servo-control software. The control loop within the PMAC board reads the actual joint positions and applies the appropriate voltages to the motors to drive the joints to the desired positions. The motors, in turn, drive gears that rotate the spools of cables on the robot so that the joints move in the desired motion.

Electronics sub-subsystem:

The electronics sub-subsystem amplifies 2-phase voltage signals from the servo-control system into 3-phase current signals using linear brushless motor servo amplifiers such as the BLH-S1-4/8 from Western Servo Design, Inc. The electronics sub-system also transmits motor shaft position digital signals from the optical encoders to the servo-control sub-system.

Figure 25:
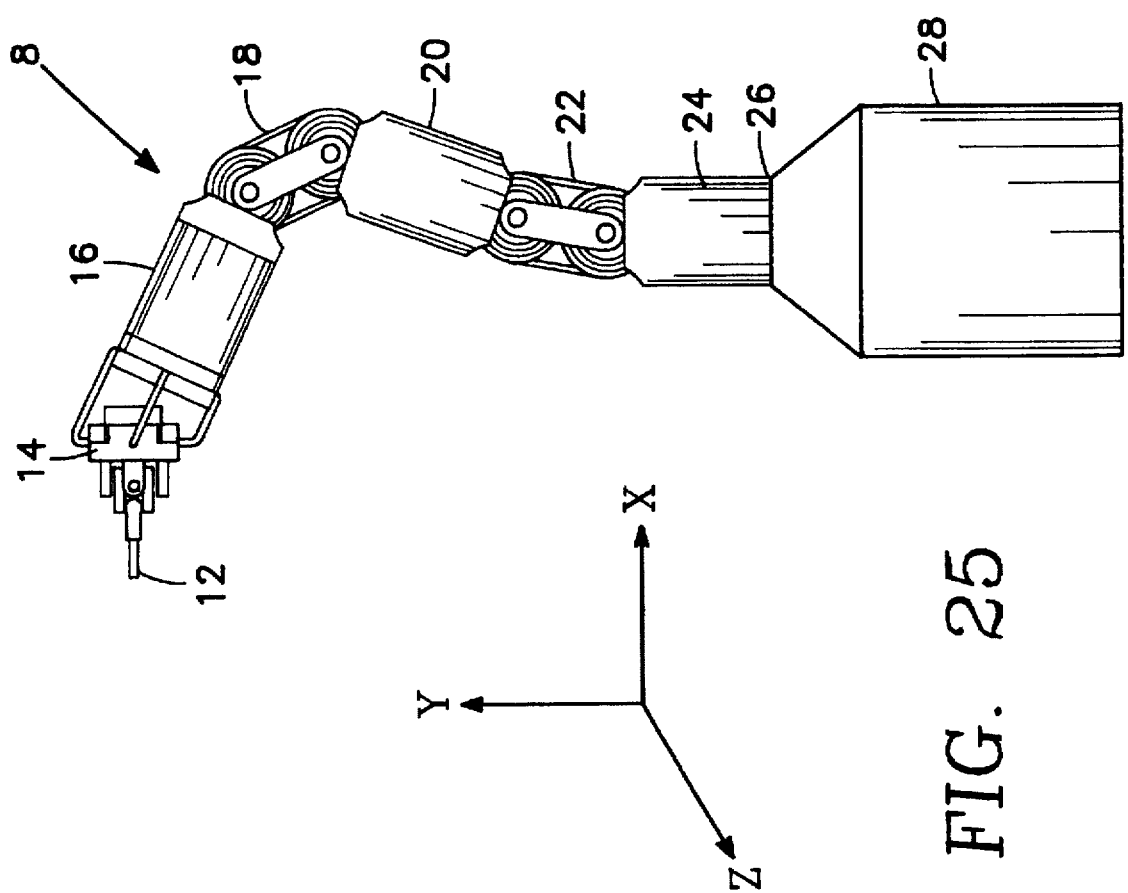
FIG. 25 illustrates the range of motion of the robot manipulator of the present invention.

Robot Range of Motion:

FIG. 25 illustrates the range of motion of the robot manipulator 8 of the present invention. The arm 10 has a large work volume so that the actuator base 28 will not have to be repositioned frequently during tasks. For example, the torso joint 26 is capable of rotating the shoulder 24 360 degrees of full rotary motion about the y axis. The elbow joint 18 and the shoulder joint 22 are capable of 360 degree limited rotary motion about the z axis. The wrist joint 14 is capable of motion about the x, y, and z axes (as described in FIG. 11 above). Since each axis is completely decoupled from the joint's motion, the wrist joint 14 is capable of 180 degrees motion about the y and z axes (pitch-and-yaw motion) and 540 degrees of continuous motion about the x axis (roll motion) and thus, operates in a full hemisphere of motion.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

APPENDIX A

COPYRIGHT
CALIFORNIA INSTITUTE OF TECHNOLOGY 1995

Table of Contents

The GUI Software Module..........................................................................Page A3
- rams_command.tcl — the Tcl/Tk script file for generating the GUI
- rams_callbacks.c — the mail prog to start up the GUI
- rams_gui_main.c — routines that are called when buttons on the screen are hit.

The NDDS Software Modules......................................................................Page A46
- RamsCommandMsg_producer.c — the message producer routines
- RamsCommandMsg_consumer.c — the message consumer routines The TRANS software Modules....................................................................Page A52
- return_to_idle.cc — the return to idle transition
- initialize_slave.cc — the initialize transition
- auto_cng_slave_task.cc — the auto change joint transition
- auto_cng_slave_joint.cc — the auto change Cartesian transition
- auto_slave_joint.cc — the go to auto joint transition
- auto_slave_task.cc — the go to auto Cartersian transition
- manual_slave_task.cc — the go to manual joint transition
- manual_slave_joint.cc — the go to manual Cartesian transition
- control_slave_joint.cc — the manual joint change transition
- control_slave_task.cc — the manual Cartesian change transition The COMPMOD software Modules.............................................................Page A106
- manual_joint.cc — the manual joint module
- manual_task.cc — the manual Cartesian module
- auto_joint.cc — the auto joint module
- auto_task.cc — the auto Cartesian module
- rams_slave_fk.cc — the forward kinematics module
- rams_slave_ik.cc — the inverse kinematics module
- controlSlave.cc — the controller
- slaveJointActuator.cc — the servo controller for setting joints
- slaveJointSensor.cc — the servo controller for reading joints The GUI Software Modules
```
/#########################################
############################
# Copyright (C) 1994, California Institute of Technology.     #
# U.S. Government Sponsorship under NASA Contract NAS9-1270 is acknowledged.#
#                                                              #
# Author: Hari Das                                             #
#                                                              #
# $Id: rams_command.tcl,v 1.3 1995/03/11 00:47:38 hari Exp hari $    #
# $Source: /home/hari/ram/software/tcl/RCS/rams_command.tcl,v $     #
##########################################
############################
# $Log: rams_command.tcl,v $
# Revision 1.3  1995/03/11  00:47:38  hari
# Added pop-up menus for master only demos and for master&slave demos.

# Revision 1.2  1995/03/09  19:07:13  hari
# Changed slave manual joint motion window and implemented commands
# to increment, decrement joint angles, select a joint to move,
# scale joint motion and quit the window.

# Revision 1.1  1995/02/25  00:06:32  hari
# Initial revision

# Revision 1.1  1995/02/25  00:05:37  hari
# Initial revision

source [info library]/init.tcl
source $tk_library/tk.tcl
#-----------------------------------------------------------
#-----------------------------------------------------------

#Set background color

#-----------------------------------------------------------
#-----------------------------------------------------------
#set backcolor grey50
#set backcolor PaleTurquoise
set backcolor #b0d8e6
#-----------------------------------------------------------

#Set w to null so that this tcl file can be used standalone
```

```
#for testing.

set w {}

#Set a flag to indicate if any other window has already been opened.
#This is so that the flag can determine is a new is to be opened.
set winOpenFlag 0

#-----------------------------------------------------------------

#set smj(scale) 1
#set smt(scale) 1
#set msd(sscale) 0
#set msd(dscale) 0
#set msp(dscale) 1
#set msp(tscale) 1
#set msp(sscale) 0
#set m_sj(pscale) 0
#set m_st(pscale) 0
#set m_st(fscale) 0
#-----------------------------------------------------------------
#-----------------------------------------------------------------

#Define procedure for main window

proc rams_cmd {{w .rams} title iconName} {
#-----------------------------------------------------------------
#-----------------------------------------------------------------

#Create window

        toplevel $w -background {#31e0ff}
        wm geometry $w +300+300
        wm title $w "$title"
        wm iconname $w "$iconName"
}
#-----------------------------------------------------------------
#-----------------------------------------------------------------

#Set min and max window sizes

        wm minsize $w. 435 350
        wm maxsize $w. 1200 800
#-----------------------------------------------------------------
```

A4

```
#                       MAIN WINDOW
#-----------------------------------------------------------------------

#Split window into 5 sections for title, slave, master, master&slave and exit

        frame $w.title -relief raised -borderwidth 4 -background $backcolor
        frame $w.init -relief raised -borderwidth 4 -background $backcolor
        frame $w.slave -relief raised -borderwidth 4 -background $backcolor
        frame $w.master -relief raised -borderwidth 4 -background $backcolor
        frame $w.masterslave -relief raised -borderwidth 4 \
                -background $backcolor
        frame $w.exit -relief raised -borderwidth 4 -background $backcolor
        pack $w.title $w.init $w.slave $w.master $w.masterslave $w.exit \
                -side top -fill both -expand 1
#-----------------------------------------------------------------------
#-----------------------------------------------------------------------

#Do title

        label $w.title.main -text "RAMS Operator's Interface" -background $backcolor
        pack $w.title.main -side left -padx 3m -pady 6m \
                -fill both -expand 1 -in $w.title
#-----------------------------------------------------------------------
#-----------------------------------------------------------------------
#                       INIT
#-----------------------------------------------------------------------

#Do init

        button $w.init.initbutton -text "INITIALIZE SYSTEM" -background green \
                -command {tclInit 0}
        pack $w.init.initbutton -side left -padx 3m -pady 6m \
                -fill both -expand 1 -in $w.init
#-----------------------------------------------------------------------
#-----------------------------------------------------------------------
#-----------------------------------------------------------------------
#                       SLAVE
#-----------------------------------------------------------------------

#Do slave

        label $w.slave.label -text "Slave" -background $backcolor
        button $w.slave.mj -text "Joint"
        button $w.slave.mt -text "Teleop"
```

A5

```
        button $w.slave.aj -text "AutomJ"
        button $w.slave.at -text "AutomT"
        pack $w.slave.label $w.slave.mj $w.slave.mt \
                $w.slave.aj $w.slave.at \
                -side left -padx 3m -pady 6m -fill both -expand 1 -in $w.slave
#------------------------------------------------------------------------

#Popwindow for Slave manual joint control
#Window has a title, a frame for selection of joint to be moved,
#frame for incrementing or decrementing selected joint,
#and a quit button.

        bind $w.slave.mj <Button-1> {
            if { $winOpenFlag < 1 } {
                set winOpenFlag 1
                tclOpenSlaveManualJ
                toplevel $w.slave.mj.win
                wm geometry $w.slave.mj.win +400+400
                label $w.slave.mj.win.title \
                        -text "Slave Keyboard Manual Joint Positioning" \
                        -background $backcolor
                frame $w.slave.mj.win.jointselect \
                        -relief raised -borderwidth 4 \
                        -background $backcolor
                frame $w.slave.mj.win.incdec \
                        -relief raised -borderwidth 4 \
                        -background $backcolor
                frame $w.slave.mj.win.scale \
                        -relief raised -borderwidth 4 \
                        -background $backcolor
                frame $w.slave.mj.win.quitframe \
                        -relief raised -borderwidth 4 \
                        -background $backcolor
                pack $w.slave.mj.win.title \
                        $w.slave.mj.win.jointselect \
                        $w.slave.mj.win.incdec \
                        $w.slave.mj.win.scale \
                        $w.slave.mj.win.quitframe \
                        -side top -fill both -expand 1 \
                        -in $w.slave.mj.win
#------------------------------------------------------------------------
#Setup radio buttons for joint selection, buttons for
#incrementing and decrementing joints, a scale for scaling
#the joint setpsize and a quit button.
```

A6

```

            foreach index {1 2 3 4 5 6 } {
                    radiobutton $w.slave.mj.win.jointselect.j$index \
                            -text "Joint$index" -variable smjindex \
                            -value $index \
                            -command {set smj(joint) $smjindex}
                    pack $w.slave.mj.win.jointselect.j$index \
                            -side left -padx 3m -pady 6m \
                            -fill both -expand 1 \
                            -in $w.slave.mj.win.jointselect
            }
            button $w.slave.mj.win.incdec.inc\
                    -text "increment joint angle" \
                    -command \
                    {tclSlaveManualJ $smj(joint) $smj(scale)}
            button $w.slave.mj.win.incdec.dec\
                    -text "decrement joint angle" \
                    -command \
                    {tclSlaveManualJ $smj(joint) [expr -1*$smj(scale)]}
            pack $w.slave.mj.win.incdec.inc \
                    $w.slave.mj.win.incdec.dec \
                    -side left -padx 3m -pady 6m \
                    -fill both -expand 1 \
                    -in $w.slave.mj.win.incdec
            scale $w.slave.mj.win.scale.name \
                    -label "stepsize increments" -from 1 -to 1000 \
                    -orient horizontal -background $backcolor \
                    -command {set smj(scale)}
            pack $w.slave.mj.win.scale.name \
                    -side top -padx 3m -pady 6m -fill both -expand 1 \
                    -in $w.slave.mj.win.scale
            button $w.slave.mj.win.quitframe.quit \
                    -text "QUIT" -background red \
                    -command {destroy $w.slave.mj.win; set winOpenFlag 0; \
                    tclCloseWin }
            pack $w.slave.mj.win.quitframe.quit \
                    -side top -padx 3m -pady 6m -fill both -expand 1 \
                    -in $w.slave.mj.win.quitframe
        }
    }
#-----------------------------------------------------------------

#Popwindow for Slave manual teleop control
#Window has a title, a frame for selection of joint to be moved,
```

A7

```
#frame for incrementing or decrementing selected task space axis,
#and a quit button.

    bind $w.slave.mt <Button-1> {
        if { $winOpenFlag < 1 } {
            set winOpenFlag 1
            tclOpenSlaveManualT
            toplevel $w.slave.mt.win -background $backcolor
            wm geometry  $w.slave.mt.win +400+400
            label $w.slave.mt.win.title \
                    -text "Slave Keyboard Manual Task Space Positioning" \
                    -background $backcolor
            frame $w.slave.mt.win.taskselect \
                    -relief raised -borderwidth 4 \
                    -background $backcolor
            frame $w.slave.mt.win.incdec \
                    -relief raised -borderwidth 4 \
                    -background $backcolor
            frame $w.slave.mt.win.scale \
                    -relief raised -borderwidth 4 \
                    -background $backcolor
            frame $w.slave.mt.win.quitframe \
                    -relief raised -borderwidth 4 \
                    -background $backcolor
            pack $w.slave.mt.win.title \
                    $w.slave.mt.win.taskselect \
                    $w.slave.mt.win.incdec \
                    $w.slave.mt.win.scale \
                    $w.slave.mt.win.quitframe \
                    -side top -fill both -expand 1 \
                    -in $w.slave.mt.win
#-----------------------------------------------------------------
#Setup radio buttons for joint selection, buttons for
#incrementing and decrementing joints, a scale for scaling
#the joint stepsize and a quit button.

            foreach index {x y z ro pi ya} {
                radiobutton $w.slave.mt.win.taskselect.t$index \
                        -text "$index" \
                        -variable smtindex \
                        -value $index \
                        -command {set smt(coord) $smtindex}
                pack $w.slave.mt.win.taskselect.t$index \
                        -side left -padx 3m -pady 6m \
```

A8

```
                              -fill both -expand 1 \
                              -in $w.slave.mt.win.taskselect
        }
        button $w.slave.mt.win.incdec.inc\
                -text "increment position" \
                -command \
                {tclSlaveManualT $smt(coord)  $smt(scale)}
        button $w.slave.mt.win.incdec.dec\
                -text "decrement position" \
                -command \
                {tclSlaveManualT $smt(coord)  [expr -1*$smt(scale)]}
        pack $w.slave.mt.win.incdec.inc \
                $w.slave.mt.win.incdec.dec \
                -side left -padx 3m -pady 6m \
                -fill both -expand 1 \
                -in $w.slave.mt.win.incdec
        scale $w.slave.mt.win.scale.name \
                -label "stepsize increments" -from 1 -to 1000 \
                -orient horizontal -background $backcolor \
                -command {set smt(scale) }
        pack $w.slave.mt.win.scale.name \
                -side top -padx 3m -pady 6m -fill both -expand 1 \
                -in $w.slave.mt.win.scale
        button $w.slave.mt.win.quitframe.quit \
                -text "QUIT" -background red \
                -command {destroy $w.slave.mt.win; set winOpenFlag 0; \
                tclCloseWin }
        pack $w.slave.mt.win.quitframe.quit \
                -side top -padx 3m -pady 6m -fill both -expand 1 \
                -in $w.slave.mt.win.quitframe
    }
}
#-----------------------------------------------------------------------

#Popwindow for Slave autonomous joint control
#Window has a title, a frame for selection of joint to be moved,
#frame for starting and stopping motion, and a quit button.

        bind $w.slave.aj <Button-1> {
            if { $winOpenFlag < 1 } {
                set winOpenFlag 1
                tclOpenSlaveAutomJ
                toplevel $w.slave.aj.win -background $backcolor
                wm geometry $w.slave.aj.win +400+400
```

A9

```
            label $w.slave.aj.win.title \
                    -text "Slave Autonomous Joint Space Positioning" \
                    -background $backcolor
            frame $w.slave.aj.win.jointselect \
                    -relief raised -borderwidth 4 \
                    -background $backcolor
            frame $w.slave.aj.win.onoff \
                    -relief raised -borderwidth 4 \
                    -background $backcolor
            frame $w.slave.aj.win.quitframe \
                    -relief raised -borderwidth 4 \
                    -background $backcolor
            pack $w.slave.aj.win.title \
                    $w.slave.aj.win.jointselect \
                    $w.slave.aj.win.onoff \
                    $w.slave.aj.win.quitframe \
                    -side top -fill both -expand 1 \
                    -in $w.slave.aj.win
#----------------------------------------------------------------------
#Setup check buttons for joint selection, button for
#starting and stopping autonomous motion and a quit button.

            foreach index {1 2 3 4 5 6} {
                    checkbutton $w.slave.aj.win.jointselect.j$index \
                            -variable saj($index) \
                            -text "$index"
                    pack $w.slave.aj.win.jointselect.j$index \
                            -side left -padx 3m -pady 6m \
                            -fill both -expand 1 \
                            -in $w.slave.aj.win.jointselect
            }
            checkbutton $w.slave.aj.win.onoff.onoffButton \
                    -text "Start/Stop" \
                    -variable sajonoff \
                    -command {tclSlaveAutomJ $saj(1) $saj(2) $saj(3) \
                    $saj(4) $saj(5) $saj(6) $sajonoff }
            pack $w.slave.aj.win.onoff.onoffButton \
                    -side left -padx 3m -pady 6m \
                    -fill both -expand 1 \
                    -in $w.slave.aj.win.onoff
            button $w.slave.aj.win.quitframe.quit \
                    -text "QUIT" -background red \
                    -command {destroy $w.slave.aj.win; set winOpenFlag 0; \
                    tclCloseWin ; set sajonoff 0 }
```

A10

```
                    pack $w.slave.aj.win.quitframe.quit \
                        -side top -padx 3m -pady 6m -fill both -expand 1 \
                        -in $w.slave.aj.win.quitframe
            }
        }
#---------------------------------------------------------------------

#Popwindow for Slave autonomous task space control
#Window has a title, a frame for selection of task space axis to be moved,
#frame for starting and stopping motion, and a quit button.

        bind $w.slave.at <Button-1> {
            if { $winOpenFlag < 1 } {
                set winOpenFlag 1
                tclOpenSlaveAutomT
                toplevel $w.slave.at.win -background $backcolor
                wm geometry $w.slave.at.win +400+400
                label $w.slave.at.win.title \
                        -text "Slave Autonomous Task Space Positioning" \
                        -background $backcolor
                frame $w.slave.at.win.taskselect \
                        -relief raised -borderwidth 4 \
                        -background $backcolor
                frame $w.slave.at.win.onoff \
                        -relief raised -borderwidth 4 \
                        -background $backcolor
                frame $w.slave.at.win.quitframe \
                        -relief raised -borderwidth 4 \
                        -background $backcolor
                pack $w.slave.at.win.title \
                        $w.slave.at.win.taskselect \
                        $w.slave.at.win.onoff \
                        $w.slave.at.win.quitframe \
                        -side top -fill both -expand 1 \
                        -in $w.slave.at.win
#---------------------------------------------------------------------
#Setup check buttons for joint selection, button for
#starting and stopping autonomous motion and a quit button.

                foreach index {x y z ro pi ya} {
                    checkbutton $w.slave.at.win.taskselect.t$index \
                        -text "$index" \
                        -variable sat($index)
                    pack $w.slave.at.win.taskselect.t$index \
```

```
                    -side left -padx 3m -pady 6m \
                    -fill both -expand 1 \
                    -in $w.slave.at.win.taskselect
            }
            checkbutton $w.slave.at.win.onoff.onoffButton\
                    -text "Start/Stop" \
                    -variable satonoff \
                    -command {tclSlaveAutomT $sat(x) $sat(y) $sat(z) \
                    $sat(ro) $sat(pi) $sat(ya) $satonoff}
            pack $w.slave.at.win.onoff.onoffButton \
                    -side left -padx 3m -pady 6m \
                    -fill both -expand 1 \
                    -in $w.slave.at.win.onoff
            button $w.slave.at.win.quitframe.quit \
                    -text "QUIT" -background red \
                    -command {destroy $w.slave.at.win; set winOpenFlag 0; \
                    tclCloseWin ; set satonoff 0 }
            pack $w.slave.at.win.quitframe.quit \
                    -side top -padx 3m -pady 6m -fill both -expand 1 \
                    -in $w.slave.at.win.quitframe
        }
    }
#----------------------------------------------------------------------
#                       MASTER
#----------------------------------------------------------------------

#Do master

        label $w.master.label -text "Master" -background $backcolor
        button $w.master.mj -text "ManualJ"
        button $w.master.aj -text "AutoJ"
        button $w.master.sd -text "Spr&Damp"
        button $w.master.sphere -text "Sphere"
        button $w.master.demo -text "TipForce"
        pack $w.master.label \
                $w.master.mj \
                $w.master.aj \
                $w.master.sd \
                $w.master.sphere \
                $w.master.demo \
                -side left -padx 3m -pady 6m \
                -fill both -expand 1 -in $w.master
#----------------------------------------------------------------------

```

A12

```
#Popwindow for Master manual joint control
#Window has a title, a frame for selection of joint to be moved,
#frame for incrementing or decrementing selected joint,
#and a quit button.

        bind $w.master.mj <Button-1> {
            if { $winOpenFlag < 1 } {
                set winOpenFlag 1
                tclOpenMasterManualJ
                toplevel $w.master.mj.win
                wm geometry $w.master.mj.win +400+400
                label $w.master.mj.win.title \
                        -text "Master Keyboard Manual Joint Positioning" \
                        -background $backcolor
                frame $w.master.mj.win.jointselect \
                        -relief raised -borderwidth 4 \
                        -background $backcolor
                frame $w.master.mj.win.incdec \
                        -relief raised -borderwidth 4 \
                        -background $backcolor
                frame $w.master.mj.win.scale \
                        -relief raised -borderwidth 4 \
                        -background $backcolor
                frame $w.master.mj.win.quitframe \
                        -relief raised -borderwidth 4 \
                        -background $backcolor
                pack $w.master.mj.win.title \
                        $w.master.mj.win.jointselect \
                        $w.master.mj.win.incdec \
                        $w.master.mj.win.scale \
                        $w.master.mj.win.quitframe \
                        -side top -fill both -expand 1 \
                        -in $w.master.mj.win
#-----------------------------------------------------------------
#Setup radio buttons for joint selection, buttons for
#incrementing and decrementing joints, a scale for scaling
#the joint setpsize and a quit button.

                foreach index {1 2 3 4 5 6 } {
                    radiobutton $w.master.mj.win.jointselect.j$index \
                            -text "Joint$index" -variable mmjindex \
                            -value $index \
                            -command {set mmj(joint) $mmjindex}
                    pack $w.master.mj.win.jointselect.j$index \
```

A13

```
                    -side left -padx 3m -pady 6m \
                    -fill both -expand 1 \
                    -in $w.master.mj.win.jointselect
        }
            button $w.master.mj.win.incdec.inc\
                    -text "increment joint angle" \
                    -command \
                    {tclMasterManualJ $mmj(joint)  $mmj(scale)}
            button $w.master.mj.win.incdec.dec\
                    -text "decrement joint angle" \
                    -command \
                    {tclMasterManualJ $mmj(joint)  [expr -1*$mmj(scale)]}
            pack $w.master.mj.win.incdec.inc \
                    $w.master.mj.win.incdec.dec \
                    -side left -padx 3m -pady 6m \
                    -fill both -expand 1 \
                    -in $w.master.mj.win.incdec
            scale $w.master.mj.win.scale.name \
                    -label "stepsize increments" -from 1 -to 1000 \
                    -orient horizontal -background $backcolor \
                    -command {set mmj(scale)}
            pack $w.master.mj.win.scale.name \
                    -side top -padx 3m -pady 6m -fill both -expand 1 \
                    -in $w.master.mj.win.scale
            button $w.master.mj.win.quitframe.quit \
                    -text "QUIT" -background red \
                    -command {destroy $w.master.mj.win; set winOpenFlag 0; \
                    tclCloseWin }
            pack $w.master.mj.win.quitframe.quit \
                    -side top -padx 3m -pady 6m -fill both -expand 1 \
                    -in $w.master.mj.win.quitframe
        }
    }
#------------------------------------------------------------------
#------------------------------------------------------------------

#Popwindow for Master autonomous joint control
#Window has a title, a frame for selection of joint to be moved,
#frame for starting and stopping motion, and a quit button.

        bind $w.master.aj <Button-1> {
            if { $winOpenFlag < 1 } {
                set winOpenFlag 1
                tclOpenMasterAutomJ
```

```
                toplevel $w.master.aj.win -background $backcolor
                wm geometry $w.master.aj.win +400+400
                label $w.master.aj.win.title \
                        -text "Master Autonomous Joint Space Positioning" \
                        -background $backcolor
                frame $w.master.aj.win.jointselect \
                        -relief raised -borderwidth 4 \
                        -background $backcolor
                frame $w.master.aj.win.onoff \
                        -relief raised -borderwidth 4 \
                        -background $backcolor
                frame $w.master.aj.win.quitframe \
                        -relief raised -borderwidth 4 \
                        -background $backcolor
                pack $w.master.aj.win.title \
                        $w.master.aj.win.jointselect \
                        $w.master.aj.win.onoff \
                        $w.master.aj.win.quitframe \
                        -side top -fill both -expand 1 \
                        -in $w.master.aj.win
#------------------------------------------------------------------------
#Setup check buttons for joint selection, button for
#starting and stopping autonomous motion and a quit button.

                foreach index {1 2 3 4 5 6} {
                        checkbutton $w.master.aj.win.jointselect.j$index \
                                -variable maj($index) \
                                -text "$index"
                        pack $w.master.aj.win.jointselect.j$index \
                                -side left -padx 3m -pady 6m \
                                -fill both -expand 1 \
                                -in $w.master.aj.win.jointselect
                }
                checkbutton $w.master.aj.win.onoff.onoffButton \
                        -text "Start/Stop" \
                        -variable majonoff \
                        -command {tclMasterAutomJ $maj(1) $maj(2) $maj(3) \
                        $maj(4) $maj(5) $maj(6) $majonoff }
                pack $w.master.aj.win.onoff.onoffButton \
                        -side left -padx 3m -pady 6m \
                        -fill both -expand 1 \
                        -in $w.master.aj.win.onoff
                button $w.master.aj.win.quitframe.quit \
                        -text "QUIT" -background red \
```

A15

```
                    -command {destroy $w.master.aj.win; set winOpenFlag 0; \
                    tclCloseWin ; set majonoff 0 }
                pack $w.master.aj.win.quitframe.quit \
                    -side top -padx 3m -pady 6m -fill both -expand 1 \
                    -in $w.master.aj.win.quitframe
            }
        }
#-----------------------------------------------------------------------

#Popwindow for Slave autonomous task space control
#Window has a title, a frame for selection of task space axis to be moved,
#frame for starting and stopping motion, and a quit button.

        bind $w.master.sd <Button-1> {
            if { $winOpenFlag < 1 } {
                set winOpenFlag 1
                tclOpenMasterSprDamp
                toplevel $w.master.sd.win -background $backcolor
                wm geometry  $w.master.sd.win +400+400
                label $w.master.sd.win.title \
                    -text "Master Spring and Damper Force Feedback Simulation" \
                    -background $backcolor
                frame $w.master.sd.win.taskselect \
                    -relief raised -borderwidth 4 \
                    -background $backcolor
                frame $w.master.sd.win.scale \
                    -relief raised -borderwidth 4 \
                    -background $backcolor
                frame $w.master.sd.win.onoff \
                    -relief raised -borderwidth 4 \
                    -background $backcolor
                frame $w.master.sd.win.quitframe \
                    -relief raised -borderwidth 4 \
                    -background $backcolor
                pack $w.master.sd.win.title \
                    $w.master.sd.win.taskselect \
                    $w.master.sd.win.scale \
                    $w.master.sd.win.onoff \
                    $w.master.sd.win.quitframe \
                    -side top -fill both -expand 1 \
                    -in $w.master.sd.win
#-----------------------------------------------------------------------
#Setup check buttons for joint selection, button for
#starting and stopping autonomous motion and a quit button.
```

A16

```
#              foreach index {x y z ro pi ya} {
                      checkbutton $w.master.sd.win.taskselect.t$index \
                              -text "$index" \
                              -variable msd($index)
                      pack $w.master.sd.win.taskselect.t$index \
                              -side left -padx 3m -pady 6m \
                              -fill both -expand 1 \
                              -in $w.master.sd.win.taskselect
              }
              scale $w.master.sd.win.scale.spring \
                      -label "Spring Constant" -from 0 -to 1000 \
                      -orient horizontal -background $backcolor \
                      -command {set msd(sscale) }
              scale $w.master.sd.win.scale.damper \
                      -label "Damping Coefficient" -from 0 -to 1000 \
                      -orient horizontal -background $backcolor \
                      -command {set msd(dscale) }
              pack $w.master.sd.win.scale.spring \
                      $w.master.sd.win.scale.damper \
                      -side top -padx 3m -pady 6m -fill both -expand 1 \
                      -in $w.master.sd.win.scale
              checkbutton $w.master.sd.win.onoff.onoffButton\
                      -text "Start/Stop" \
                      -variable msdonoff \
                      -command { tclMasterSprDamp $msd(x) $msd(y) $msd(z) \
                      $msd(ro) $msd(pi) $msd(ya) $msd(sscale) \
                      $msd(dscale) $msdonoff}
              pack $w.master.sd.win.onoff.onoffButton \
                      -side left -padx 3m -pady 6m \
                      -fill both -expand 1 \
                      -in $w.master.sd.win.onoff
              button $w.master.sd.win.quitframe.quit \
                      -text "QUIT" -background red \
                      -command {destroy $w.master.sd.win; set winOpenFlag 0; \
                      tclCloseWin ; set msdonoff 0}
              pack $w.master.sd.win.quitframe.quit \
                      -side top -padx 3m -pady 6m -fill both -expand 1 \
                      -in $w.master.sd.win.quitframe
       }
    }
#-----------------------------------------------------------------------

#Popwindow for Slave autonomous task space control
```

A17

```
#Window has a title, a frame for selection of task space axis to be moved,
#frame for starting and stopping motion, and a quit button.

        bind $w.master.sphere <Button-1> {
            if { $winOpenFlag < 1 } {
                set winOpenFlag 1
                tclOpenMasterSphere
                toplevel $w.master.sphere.win -background $backcolor
                wm geometry $w.master.sphere.win +400+400
                label $w.master.sphere.win.title \
                        -text "Moving within a Sphere Force Feedback Simulation" \
                        -background $backcolor
                frame $w.master.sphere.win.taskselect \
                        -relief raised -borderwidth 4 \
                        -background $backcolor
                frame $w.master.sphere.win.scale \
                        -relief raised -borderwidth 4 \
                        -background $backcolor
                frame $w.master.sphere.win.onoff \
                        -relief raised -borderwidth 4 \
                        -background $backcolor
                frame $w.master.sphere.win.quitframe \
                        -relief raised -borderwidth 4 \
                        -background $backcolor
                pack $w.master.sphere.win.title \
                        $w.master.sphere.win.taskselect \
                        $w.master.sphere.win.scale \
                        $w.master.sphere.win.onoff \
                        $w.master.sphere.win.quitframe \
                        -side top -fill both -expand 1 \
                        -in $w.master.sphere.win
#-----------------------------------------------------------------------
#Setup check buttons for joint selection, button for
#starting and stopping autonomous motion and a quit button.

                foreach index {x y z ro pi ya} {
                    checkbutton $w.master.sphere.win.taskselect.t$index \
                        -text "$index" \
                        -variable msp($index)
                    pack $w.master.sphere.win.taskselect.t$index \
                        -side left -padx 3m -pady 6m \
                        -fill both -expand 1 \
                        -in $w.master.sphere.win.taskselect
                }
```

```
            scale $w.master.sphere.win.scale.diameter \
                    -label "Sphere Diameter" -from 1 -to 1000 \
                    -orient horizontal -background $backcolor\
                    -command {set msp(dscale) }
            scale $w.master.sphere.win.scale.buffer_thickness \
                    -label "Buffer Thickness" -from 1 -to 1000 \
                    -orient horizontal -background $backcolor \
                    -command {set msp(tscale) }
            scale $w.master.sphere.win.scale.spring_const \
                    -label "Buffer Spring Constant" -from 0 -to 1000 \
                    -orient horizontal -background $backcolor\
                    -command {set msp(sscale) }
            pack $w.master.sphere.win.scale.diameter \
                    $w.master.sphere.win.scale.buffer_thickness \
                    $w.master.sphere.win.scale.spring_const \
                    -side top -padx 3m -pady 6m -fill both -expand 1 \
                    -in $w.master.sphere.win.scale
            checkbutton $w.master.sphere.win.onoff.onoffButton\
                    -text "Start/Stop" \
                    -variable msponoff \
                    -command { tclMasterSphere $msp(x) $msp(y) $msp(z) \
                    $msp(ro) $msp(pi) $msp(ya) $msp(dscale) \
                    $msp(tscale) $msp(sscale) $msponoff}
            pack $w.master.sphere.win.onoff.onoffButton \
                    -side left -padx 3m -pady 6m \
                    -fill both -expand 1 \
                    -in $w.master.sphere.win.onoff
            button $w.master.sphere.win.quitframe.quit \
                    -text "QUIT" -background red \
                    -command {destroy $w.master.sphere.win; set winOpenFlag 0; \
                    tclCloseWin ; set msponoff 0}
            pack $w.master.sphere.win.quitframe.quit \
                    -side top -padx 3m -pady 6m -fill both -expand 1 \
                    -in $w.master.sphere.win.quitframe
        }
    }
#-------------------------------------------------------------

#Popwindow for Slave autonomous task space control
#Window has a title, a frame for selection of task space axis to be moved,
#frame for starting and stopping motion, and a quit button.

        bind $w.master.demo <Button-1> {
            if { $winOpenFlag < 1 } {
```

```
set winOpenFlag 1
tclOpenMasterDemo
toplevel $w.master.demo.win -background $backcolor
wm geometry $w.master.demo.win +400+400
label $w.master.demo.win.title \
        -text "Manual Master Arm Force Setting" \
        -background $backcolor
frame $w.master.demo.win.taskselect \
        -relief raised -borderwidth 4 \
        -background $backcolor
frame $w.master.demo.win.scale \
        -relief raised -borderwidth 4 \
        -background $backcolor
frame $w.master.demo.win.incdec \
        -relief raised -borderwidth 4 \
        -background $backcolor
frame $w.master.demo.win.quitframe \
        -relief raised -borderwidth 4 \
        -background $backcolor
pack $w.master.demo.win.title \
        $w.master.demo.win.taskselect \
        $w.master.demo.win.scale \
        $w.master.demo.win.incdec \
        $w.master.demo.win.quitframe \
        -side top -fill both -expand 1 \
        -in $w.master.demo.win
#------------------------------------------------------------------------
#Setup check buttons for joint selection, button for
#starting and stopping autonomous motion and a quit button.

        foreach index {x y z ro pi ya} {
                radiobutton $w.master.demo.win.taskselect.t$index \
                        -text "$index" \
                        -variable mdmindex \
                        -value $index \
                        -command {set mdm(coord) $mdmindex}
                pack $w.master.demo.win.taskselect.t$index \
                        -side left -padx 3m -pady 6m \
                        -fill both -expand 1 \
                        -in $w.master.demo.win.taskselect
        }
        button $w.master.demo.win.incdec.inc\
                -text "increment force" \
                -command \
```

A20

```
                {tclMasterDemo $mdm(coord) $mdm(scale)}
        button $w.master.demo.win.incdec.dec\
                -text "decrement force" \
                -command \
                {tclMasterDemo $mdm(coord) [expr -1*$mdm(scale)]}
        pack $w.master.demo.win.incdec.inc \
                $w.master.demo.win.incdec.dec \
                -side left -padx 3m -pady 6m \
                -fill both -expand 1 \
                -in $w.master.demo.win.incdec
        scale $w.master.demo.win.scale.name \
                -label "stepsize increments" -from 1 -to 1000 \
                -orient horizontal -background $backcolor \
                -command {set mdm(scale) }
        pack $w.master.demo.win.scale.name \
                -side top -padx 3m -pady 6m -fill both -expand 1 \
                -in $w.master.demo.win.scale
        button $w.master.demo.win.quitframe.quit \
                -text "QUIT" -background red \
                -command {destroy $w.master.demo.win; set winOpenFlag 0; \
                tclCloseWin }
        pack $w.master.demo.win.quitframe.quit \
                -side top -padx 3m -pady 6m -fill both -expand 1 \
                -in $w.master.demo.win.quitframe
        }
    }
#----------------------------------------------------------------------
#                       MASTER & SLAVE
#----------------------------------------------------------------------

#Do master&slave

        label $w.masterslave.label -text "Master&Slave" -background $backcolor
        button $w.masterslave.mj -text "Joint"
        button $w.masterslave.mt -text "Task"
        pack $w.masterslave.label \
                $w.masterslave.mj \
                $w.masterslave.mt \
                -side left -padx 3m -pady 6m \
                -fill both -expand 1 -in $w.masterslave
#----------------------------------------------------------------------

#Popwindow for Slave autonomous task space control
#Window has a title, a frame for selection of task space axis to be moved,
```

A21

```
#frame for starting and stopping motion, and a quit button.

      bind $w.masterslave.mj <Button-1> {
           if { $winOpenFlag < 1 } {
                set winOpenFlag 1
                tclOpenMasterSlaveJoint
                toplevel $w.masterslave.mj.win -background $backcolor
                wm geometry  $w.masterslave.mj.win  +400+400
                label $w.masterslave.mj.win.title \
                         -text "Manual Joint Space Positioning" \
                         -background $backcolor
                frame $w.masterslave.mj.win.jointselect \
                         -relief raised -borderwidth 4 \
                         -background $backcolor
                frame $w.masterslave.mj.win.scale \
                         -relief raised -borderwidth 4 \
                         -background $backcolor
                frame $w.masterslave.mj.win.onoff \
                         -relief raised -borderwidth 4 \
                         -background $backcolor
                frame $w.masterslave.mj.win.quitframe \
                         -relief raised -borderwidth 4 \
                         -background $backcolor
                pack $w.masterslave.mj.win.title \
                         $w.masterslave.mj.win.jointselect \
                         $w.masterslave.mj.win.scale \
                         $w.masterslave.mj.win.onoff \
                         $w.masterslave.mj.win.quitframe \
                         -side top -fill both -expand 1 \
                         -in $w.masterslave.mj.win
#------------------------------------------------------------------
#Setup check buttons for joint selection, button for
#starting and stopping autonomous motion and a quit button.

                foreach index {1 2 3 4 5 6} {
                     checkbutton $w.masterslave.mj.win.jointselect.j$index \
                              -text "$index" \
                              -variable m_sj($index)
                     pack $w.masterslave.mj.win.jointselect.j$index \
                              -side left -padx 3m -pady 6m \
                              -fill both -expand 1 \
                              -in $w.masterslave.mj.win.jointselect
                }
                scale $w.masterslave.mj.win.scale.position \
```

```
                    -label "position scaling" -from 0 -to 1000 \
                    -orient horizontal -background $backcolor \
                    -command {set m_sj(pscale) }
            pack $w.masterslave.mj.win.scale.position \
                    -side top -padx 3m -pady 6m -fill both -expand 1 \
                    -in $w.masterslave.mj.win.scale
            checkbutton $w.masterslave.mj.win.onoff.onoffButton\
                    -text "Start/Stop" \
                    -variable m_sjonoff \
                    -command {tclMasterSlaveJoint $m_sj(1) $m_sj(2) $m_sj(3) \
                    $m_sj(4) $m_sj(5) $m_sj(6) $m_sj(pscale) $m_sjonoff}
            pack $w.masterslave.mj.win.onoff.onoffButton \
                    -side left -padx 3m -pady 6m \
                    -fill both -expand 1 \
                    -in $w.masterslave.mj.win.onoff
            button $w.masterslave.mj.win.quitframe.quit \
                    -text "QUIT" -background red \
                    -command {destroy $w.masterslave.mj.win; \
                    set winOpenFlag 0; \
                    tclCloseWin ; set m_sjonoff 0}
            pack $w.masterslave.mj.win.quitframe.quit \
                    -side top -padx 3m -pady 6m -fill both -expand 1 \
                    -in $w.masterslave.mj.win.quitframe
        }
    }
#-----------------------------------------------------------------------

#Popwindow for Master & Slave autonomous task space control
#Window has a title, a frame for selection of task space axis to be moved,
#frame for starting and stopping motion, and a quit button.

        bind $w.masterslave.mt <Button-1> {
            if { $winOpenFlag < 1 } {
                set winOpenFlag 1
                tclOpenMasterSlaveTask
                toplevel $w.masterslave.mt.win -background $backcolor
                wm geometry $w.masterslave.mt.win +400+400
                label $w.masterslave.mt.win.title \
                        -text "Manual Task Space Positioning" \
                        -background $backcolor
                frame $w.masterslave.mt.win.taskselect \
                        -relief raised -borderwidth 4 \
                        -background $backcolor
                frame $w.masterslave.mt.win.control \
```

```
                    -relief raised -borderwidth 4 \
                    -background $backcolor
            frame $w.masterslave.mt.win.scale \
                    -relief raised -borderwidth 4 \
                    -background $backcolor
            frame $w.masterslave.mt.win.onoff \
                    -relief raised -borderwidth 4 \
                    -background $backcolor
            frame $w.masterslave.mt.win.quitframe \
                    -relief raised -borderwidth 4 \
                    -background $backcolor
            pack $w.masterslave.mt.win.title \
                    $w.masterslave.mt.win.taskselect \
                    $w.masterslave.mt.win.control \
                    $w.masterslave.mt.win.scale \
                    $w.masterslave.mt.win.onoff \
                    $w.masterslave.mt.win.quitframe \
                    -side top -fill both -expand 1 \
                    -in $w.masterslave.mt.win
#-----------------------------------------------------------------------
#Setup check buttons for task selection, button for
#starting and stopping autonomous motion and a quit button.

            foreach index {x y z ro pi ya} {
                    checkbutton $w.masterslave.mt.win.taskselect.t$index \
                            -text "$index" \
                            -variable m_st($index)
                    pack $w.masterslave.mt.win.taskselect.t$index \
                            -side left -padx 3m -pady 6m \
                            -fill both -expand 1 \
                            -in $w.masterslave.mt.win.taskselect
            }
            checkbutton $w.masterslave.mt.win.control.ffb \
                    -text "FFB on/off" \
                    -variable m_stfonoff
            checkbutton $w.masterslave.mt.win.control.view \
                    -text "Scope view" \
                    -variable m_stview
            checkbutton $w.masterslave.mt.win.control.all \
                    -text "All axes on/off" \
                    -variable m_staonoff \
                    -command { \
                    foreach index {x y z ro pi ya} \
                            { set m_st($index) $m_staonoff}}
```

A24

```
            pack $w.masterslave.mt.win.control.ffb \
                    $w.masterslave.mt.win.control.all \
                    $w.masterslave.mt.win.control.view \
                    -side left -padx 3m -pady 6m \
                    -fill both -expand 1 \
                    -in $w.masterslave.mt.win.control
            scale $w.masterslave.mt.win.scale.position \
                    -label "position scaling" -from 0 -to 1000 \
                    -orient horizontal -background $backcolor \
                    -command {set m_st(pscale) }
            scale $w.masterslave.mt.win.scale.force \
                    -label "force scaling" -from 0 -to 1000 \
                    -orient horizontal -background $backcolor \
                    -command {set m_st(fscale) }
            pack $w.masterslave.mt.win.scale.position \
                    $w.masterslave.mt.win.scale.force \
                    -side top -padx 3m -pady 6m -fill both -expand 1 \
                    -in $w.masterslave.mt.win.scale
            checkbutton $w.masterslave.mt.win.onoff.onoffButton\
                    -text "Start/Stop" \
                    -variable m_stonoff \
                    -command {tclMasterSlaveTask $m_st(x) $m_st(y) $m_st(z) \
                    $m_st(ro) $m_st(pi) $m_st(ya) $m_st(pscale) $m_st(fscale) \
                    $m_stonoff $m_stfonoff $m_stview }
            pack $w.masterslave.mt.win.onoff.onoffButton \
                    -side left -padx 3m -pady 6m \
                    -fill both -expand 1 \
                    -in $w.masterslave.mt.win.onoff
            button $w.masterslave.mt.win.quitframe.quit \
                    -text "QUIT" -background red \
                    -command {destroy $w.masterslave.mt.win; \
                    set winOpenFlag 0; tclCloseWin ; set m_stonoff 0}
            pack $w.masterslave.mt.win.quitframe.quit \
                    -side top -padx 3m -pady 6m -fill both -expand 1 \
                    -in $w.masterslave.mt.win.quitframe
        }
    }
#-------------------------------------------------------------------------
#-------------------------------------------------------------------------
#                    EXIT
#-------------------------------------------------------------------------

#Do exit

```

```
button $w.exit.exitbutton -text "EXIT" -background red -command tclExit
pack $w.exit.exitbutton -side left -padx 3m -pady 6m \
        -fill both -expand 1 -in $w.exit
#----------------------------------------------------------------
#----------------------------------------------------------------

#Callback procedures

proc tclInit { a } {
    applInit $a
    }
proc tclSlaveManualJ { a b } {
        applSlaveManualJ $a $b
    }
proc tclSlaveManualT { a b } {
        applSlaveManualT $a $b
    }
proc tclSlaveAutomJ { a b c d e f g } {
        applSlaveAutomJ $a $b $c $d $e $f $g
    }
proc tclSlaveAutomT { a b c d e f g } {
        applSlaveAutomT $a $b $c $d $e $f $g
    }
proc tclMasterManualJ { a b } {
        applMasterManualJ $a $b
    }
proc tclMasterAutomJ { a b c d e f g } {
        applMasterAutomJ $a $b $c $d $e $f $g
    }
proc tclMasterSprDamp { a b c d e f g h i } {
        applMasterSprDamp $a $b $c $d $e $f $g $h $i
    }
proc tclMasterSphere { a b c d e f g h i j } {
        applMasterSphere $a $b $c $d $e $f $g $h $i $j
    }
proc tclMasterDemo { a b } {
        applMasterDemo $a $b
    }
proc tclMasterSlaveJoint { a b c d e f g h } {
        applMasterSlaveJoint $a $b $c $d $e $f $g $h
    }
proc tclMasterSlaveTask { a b c d e f g h i j k } {
        applMasterSlaveTask $a $b $c $d $e $f $g $h $i $j $k
    }
```

```
proc tclOpenSlaveManualJ { } {
    applOpenSlaveManualJ
}
proc tclOpenSlaveManualT { } {
    applOpenSlaveManualT
}
proc tclOpenSlaveAutomJ { } {
    applOpenSlaveAutomJ
}
proc tclOpenSlaveAutomT { } {
    applOpenSlaveAutomT
}
proc tclOpenMasterManualJ { } {
    applOpenMasterManualJ
}
proc tclOpenMasterAutomJ { } {
    applOpenMasterAutomJ
}
proc tclOpenMasterSprDamp { } {
    applOpenMasterSprDamp
}
proc tclOpenMasterSphere { } {
    applOpenMasterSphere
}
proc tclOpenMasterDemo { } {
    applOpenMasterDemo
}
proc tclOpenMasterSlaveJoint { } {
    applOpenMasterSlaveJoint
}
proc tclOpenMasterSlaveTask { } {
    applOpenMasterSlaveTask
}
proc tclCloseWin { } {
  applCloseWin
  }
proc tclExit { } {
  applExit
  }
```

```
/************************************************************************
 *      Copyright (c) 1993 Jet Propulsion Laboratory
 *      U.S. Government Sponsorship under NASA Contract NAS7-1270 is acknowledge
 *
 *      Author: Hari Das
 *
 *      $Id: rams_callbacks.c,v 1.1 1995/08/25 21:55:20 hari Exp hari $
 *      $Source: /home/hari/ram/software/tcl/rams/RCS/rams_callbacks.c,v $
 *      $Revision: 1.1 $
 *      $Date: 1995/08/25 21:55:20 $
 *      $Author: hari $
 ************************************************************************
 * $Log: rams_callbacks.c,v $
 * Revision 1.1  1995/08/25  21:55:20  hari
 * Initial revision
 *
 *
 */ static char rcsid[] = "$Id: rams_callbacks.c,v 1.1 1995/08/25 21:55:20 hari Exp hari $";

/***
   NAME
     rams_gui_main
   PURPOSE
     Main program to initialize and run the GUI for the RAMS
     master slave system demonstration.
   NOTES HISTORY
     Hari Das - Feb 28, 1995: Created.
***/
#include "rams_gui.h"
#ifdef NDDS
/* NDDS related variables */
#include "transitionCommands.h"
#include "NDDS.h"
#include "/home/hari/ram/software/ndds/rams/RamsCommandMsg.h"

int nddsDomain = 7491;
NDDSProducer commandProducer;
RamsCommandMsg command;
float persistence = 15.0f;
float strength = 1.0f;
```

```
#endif /* ifdef NDDS */

/* Tcl variables */
extern Tcl_Interp *theInterpreter;

static CommandHandlerType
    applInit, applSlaveManualJ, applSlaveManualT,
    applSlaveAutomJ, applSlaveAutomT,
    applMasterManualJ, applMasterSprDamp, applMasterSphere, applMasterDemo,
    applMasterSlaveJoint, applMasterAutomJ, applMasterSlaveTask,
    applOpenSlaveManualJ, applOpenSlaveManualT,
    applOpenSlaveAutomJ, applOpenSlaveAutomT,
    applOpenMasterManualJ, applOpenMasterAutomJ, applOpenMasterSprDamp,
    applOpenMasterSphere, applOpenMasterDemo,
    applOpenMasterSlaveJoint, applOpenMasterSlaveTask,
    applCloseWin, applExit;

callbackFn newCommands[] = {
    { "applInit", applInit },
    { "applSlaveManualJ", applSlaveManualJ },
    { "applOpenSlaveManualJ", applOpenSlaveManualJ },
    { "applSlaveManualT", applSlaveManualT },
    { "applOpenSlaveManualT", applOpenSlaveManualT },
    { "applSlaveAutomJ", applSlaveAutomJ },
    { "applOpenSlaveAutomJ", applOpenSlaveAutomJ },
    { "applSlaveAutomT", applSlaveAutomT },
    { "applOpenSlaveAutomT", applOpenSlaveAutomT },
    { "applMasterManualJ", applMasterManualJ },
    { "applOpenMasterManualJ", applOpenMasterManualJ },
    { "applMasterAutomJ", applMasterAutomJ },
    { "applOpenMasterAutomJ", applOpenMasterAutomJ },
    { "applMasterSprDamp", applMasterSprDamp},
    { "applOpenMasterSprDamp", applOpenMasterSprDamp},
    { "applMasterSphere", applMasterSphere},
    { "applOpenMasterSphere", applOpenMasterSphere},
    { "applMasterDemo", applMasterDemo},
    { "applOpenMasterDemo", applOpenMasterDemo},
    { "applMasterSlaveJoint", applMasterSlaveJoint},
    { "applOpenMasterSlaveJoint", applOpenMasterSlaveJoint},
    { "applMasterSlaveTask", applMasterSlaveTask},
    { "applOpenMasterSlaveTask", applOpenMasterSlaveTask},
    { "applCloseWin", applCloseWin},
    { "applExit", applExit },
    { NULL, NULL }
```

A29

```
};
#ifdef NDDS
void initNDDS();
void reset_trans_param();
void print_command();
#endif /* ifdef NDDS */
void ramsInit(int initSys);
void ramsSlaveManualJ(int joint, int change);
void ramsSlaveManualT(char *coord, int change);
void ramsSlaveAutomJ(int joint1, int joint2, int joint3, int joint4, int
                joint5, int joint6, int onoff);
void ramsSlaveAutomT(int coord1, int coord2, int coord3,
                int coord4, int coord5, int coord6,
                int onoff);
void ramsMasterManualJ(int joint, int change);
void ramsMasterAutomJ(int joint1, int joint2, int joint3, int joint4, int
                joint5, int joint6, int onoff);
void ramsMasterSprDamp(int coord1, int coord2, int coord3,
                int coord4, int coord5, int coord6,
                int sscale, int dscale, int onoff);
void ramsMasterSphere(int coord1, int coord2, int coord3,
                int coord4, int coord5, int coord6,
                int dscale, int tscale, int sscale,
                int onoff);
void ramsMasterDemo(char *axis, int change);
void ramsMasterSlaveJoint(int joint1, int joint2, int joint3, int joint4, int
                joint5, int joint6,
                    int pscale, int onoff);
void ramsMasterSlaveTask(int coord1, int coord2, int coord3,
                int coord4, int coord5, int coord6,
                    int pscale, int fscale, int onoff, int
                    fonoff, int view);
void ramsOpenSlaveManualJ();
void ramsOpenSlaveManualT();
void ramsOpenSlaveAutomJ();
void ramsOpenSlaveAutomT();
void ramsOpenMasterManualJ();
void ramsOpenMasterAutomJ();
void ramsOpenMasterSprDamp();
void ramsOpenMasterSphere();
void ramsOpenMasterDemo();
void ramsOpenMasterSlaveJoint();
void ramsOpenMasterSlaveTask();
void ramsCloseWin();
```

```
void ramsExit();

#ifdef NDDS
void init_NDDS()
{
    NddsInit(nddsDomain);
    NddsVerbositySet(2);
    RamsCommandMsgNddsRegister();
    command = (RamsCommandMsg)calloc(1, sizeof(*command));
    command->current_mode = calloc(128, sizeof(char));
    command->dest_mode = calloc(128, sizeof(char));
    commandProducer = NddsProducerCreate("Producer", NDDS_ASYNCHRONOUS,
                            persistence, strength);
    NddsProducerAddProduction(commandProducer, "RamsCommandMsg",
                    "Example RamsCommandMsg", command,
                    0, NULL, NULL);
    reset_trans_param();
    printf("Finished init_NDDS\n");

}
void reset_trans_param()
{
    register int i;

for ( i=0; i<11; i++ ) command->trans_param.change_int[i] = 0;
    for ( i=0; i<6; i++ ) command->trans_param.change_flt[i] = 0.0;
} void print_command()
{
    register int i;

printf("transition = %d\n", command->transitionCommand);
    printf("current_mode = %s", command->current_mode);
    printf("dest_mode    = %s", command->dest_mode);
    printf("Integer = ");
    for ( i=0; i<11; i++ ) printf("%d ", command->trans_param.change_int[i]);
    printf("\nFloat = ");
    for ( i=0; i<6; i++ ) printf("%d ", command->trans_param.change_flt[i]);
    printf("\n");
} endif /* ifdef NDDS */
```

A31

```c
void ramsInit(int initSys)
{
    printf("Command to initialize system\n");
#ifdef NDDS
    command->transitionCommand = INITIALIZE;
    sprintf(command->current_mode, "idle\n");
    sprintf(command->dest_mode, "idle\n");
    NddsProducerSample(commandProducer);
    print_command();
#endif /* ifdef NDDS */
}
void ramsSlaveManualJ(int joint, int change)
{
    printf("Command to change joint %d angle by %d\n",
        joint, change);
#ifdef NDDS
    command->trans_param.change_int[0] = joint;
    command->trans_param.change_int[1] = change;
    command->transitionCommand = SLAVE_JOINTS_MANUAL_CHANGE;
    sprintf(command->current_mode, "slave_joints_manual\n");
    sprintf(command->dest_mode, "slave_joints_manual\n");
    NddsProducerSample(commandProducer);
    print_command();
    reset_trans_param();

#endif /* ifdef NDDS */
}
void ramsSlaveManualT(char *axis, int change)
{
    printf("Command to change coordinate %s by %d\n",
        axis, change);
#ifdef NDDS
    if (strncmp(axis, "ro", 2) ==0) command->trans_param.change_int[0] = 4;
    else if (strncmp(axis, "pi", 2)==0) command->trans_param.change_int[0] = 5;
    else if (strncmp(axis, "ya", 2)==0) command->trans_param.change_int[0] = 6;
    else if (strncmp(axis, "x", 1)==0) command->trans_param.change_int[0] = 1;
    else if (strncmp(axis, "y", 1)==0) command->trans_param.change_int[0] = 2;
    else if (strncmp(axis, "z", 1)==0) command->trans_param.change_int[0] = 3;
    command->trans_param.change_int[1] = change;
    command->transitionCommand = SLAVE_TASK_MANUAL_CHANGE;
    sprintf(command->current_mode, "slave_task_manual\n");
    sprintf(command->dest_mode, "slave_task_manual\n");
    NddsProducerSample(commandProducer);
    print_command();
```

A32

```c
    reset_trans_param();
#endif /* ifdef NDDS */
}
void ramsSlaveAutomJ(int joint1, int joint2, int joint3, int joint4,
              int joint5, int joint6, int onoff)
{
    printf("Joints selected: %d %d %d %d %d %d to turn %d\n",
         joint1, joint2, joint3, joint4, joint5, joint6, onoff);
#ifdef NDDS
    command->transitionCommand = SLAVE_JOINTS_AUTO_CHANGE;
    sprintf(command->current_mode, "slave_joints_auto\n");
    sprintf(command->dest_mode, "slave_joints_auto\n");
    command->trans_param.change_int[0] = joint1;
    command->trans_param.change_int[1] = joint2;
    command->trans_param.change_int[2] = joint3;
    command->trans_param.change_int[3] = joint4;
    command->trans_param.change_int[4] = joint5;
    command->trans_param.change_int[5] = joint6;
    command->trans_param.change_int[6] = onoff;
    NddsProducerSample(commandProducer);
    print_command();
    reset_trans_param();
#endif /* ifdef NDDS */
}
void ramsSlaveAutomT(int coord1, int coord2, int coord3,
              int coord4, int coord5, int coord6, int onoff)
{
    printf("Coords selected: %d %d %d %d %d %d to turn %d\n",
         coord1, coord2, coord3,
         coord4, coord5, coord6, onoff);
#ifdef NDDS
    command->transitionCommand = SLAVE_TASK_AUTO_CHANGE;
    sprintf(command->current_mode, "slave_task_auto\n");
    sprintf(command->dest_mode, "slave_task_auto\n");
    command->trans_param.change_int[0] = coord1;
    command->trans_param.change_int[1] = coord2;
    command->trans_param.change_int[2] = coord3;
    command->trans_param.change_int[3] = coord4;
    command->trans_param.change_int[4] = coord5;
    command->trans_param.change_int[5] = coord6;
    command->trans_param.change_int[6] = onoff;
    NddsProducerSample(commandProducer);
    print_command();
    reset_trans_param();
```

```c
#endif /* ifdef NDDS */
}
void ramsMasterManualJ(int joint, int change)
{
    printf("Command to change joint %d angle by %d\n",
           joint, change);
#ifdef NDDS
    command->trans_param.change_int[0] = joint;
    command->trans_param.change_int[1] = change;
    command->transitionCommand = MASTER_JOINTS_MANUAL_CHANGE;
    sprintf(command->current_mode, "master_joints_manual\n");
    sprintf(command->dest_mode, "master_joints_manual\n");
    NddsProducerSample(commandProducer);
    print_command();
    reset_trans_param();

#endif /* ifdef NDDS */
}
void ramsMasterAutomJ(int joint1, int joint2, int joint3, int joint4,
              int joint5, int joint6, int onoff)
{
    printf("Joints selected: %d %d %d %d %d %d to turn %d\n",
           joint1, joint2, joint3, joint4, joint5, joint6, onoff);
#ifdef NDDS
    command->transitionCommand = MASTER_JOINTS_AUTO_CHANGE;
    sprintf(command->current_mode, "master_joints_auto\n");
    sprintf(command->dest_mode, "master_joints_auto\n");
    command->trans_param.change_int[0] = joint1;
    command->trans_param.change_int[1] = joint2;
    command->trans_param.change_int[2] = joint3;
    command->trans_param.change_int[3] = joint4;
    command->trans_param.change_int[4] = joint5;
    command->trans_param.change_int[5] = joint6;
    command->trans_param.change_int[6] = onoff;
    NddsProducerSample(commandProducer);
    print_command();
    reset_trans_param();
#endif /* ifdef NDDS */
}
void ramsMasterSprDamp(int coord1, int coord2, int coord3,
              int coord4, int coord5, int coord6,
              int sscale, int dscale, int onoff)
{
    printf(
```

```
            "Coords selected: %d %d %d %d %d %d, scale spr %d, damp %d "
            "turn %d\n",
            coord1, coord2, coord3,
            coord4, coord5, coord6, sscale,
            dscale, onoff);
#ifdef NDDS
    command->transitionCommand = MASTER_SPRING_DAMPER_CHANGE;
    sprintf(command->current_mode, "master_spring_damper\n");
    sprintf(command->dest_mode, "master_spring_damper\n");
    command->trans_param.change_int[0] = coord1;
    command->trans_param.change_int[1] = coord2;
    command->trans_param.change_int[2] = coord3;
    command->trans_param.change_int[3] = coord4;
    command->trans_param.change_int[4] = coord5;
    command->trans_param.change_int[5] = coord6;
    command->trans_param.change_int[6] = sscale;
    command->trans_param.change_int[7] = dscale;
    command->trans_param.change_int[8] = onoff;
    NddsProducerSample(commandProducer);
    print_command();
    reset_trans_param();
#endif /* ifdef NDDS */
}
void ramsMasterSphere(int coord1, int coord2, int coord3,
                      int coord4, int coord5, int coord6,
                      int dscale, int tscale, int sscale,
                      int onoff)
{
    printf(
            "Coords selected: %d %d %d %d %d %d, diam %d, thick %d "
            "spring %d turn %d\n",
            coord1, coord2, coord3,
            coord4, coord5, coord6, dscale,
            tscale, sscale, onoff);
#ifdef NDDS
    command->transitionCommand = MASTER_SPHERE_CHANGE;
    sprintf(command->current_mode, "master_sphere\n");
    sprintf(command->dest_mode, "master_sphere\n");
    command->trans_param.change_int[0] = coord1;
    command->trans_param.change_int[1] = coord2;
    command->trans_param.change_int[2] = coord3;
    command->trans_param.change_int[3] = coord4;
    command->trans_param.change_int[4] = coord5;
    command->trans_param.change_int[5] = coord6;
```

```c
        command->trans_param.change_int[6] = dscale;
        command->trans_param.change_int[7] = tscale;
        command->trans_param.change_int[8] = sscale;
        command->trans_param.change_int[9] = onoff;
        NddsProducerSample(commandProducer);
        print_command();
        reset_trans_param();
#endif /* ifdef NDDS */
} void ramsMasterDemo(char *axis, int change)
{
    printf("Command to change task %s angle by %d\n",
        axis, change);
#ifdef NDDS
    if (strncmp(axis, "ro", 2) ==0) command->trans_param.change_int[0] = 4;
    else if (strncmp(axis, "pi", 2)==0) command->trans_param.change_int[0] = 5;
    else if (strncmp(axis, "ya", 2)==0) command->trans_param.change_int[0] = 6;
    else if (strncmp(axis, "x", 1)==0) command->trans_param.change_int[0] = 1;
    else if (strncmp(axis, "y", 1)==0) command->trans_param.change_int[0] = 2;
    else if (strncmp(axis, "z", 1)==0) command->trans_param.change_int[0] = 3;
    command->trans_param.change_int[1] = change;
    command->transitionCommand = MASTER_DEMO_CHANGE;
    sprintf(command->current_mode, "master_demo_manual\n");
    sprintf(command->dest_mode, "master_demo_manual\n");
    NddsProducerSample(commandProducer);
    print_command();
    reset_trans_param();

#endif /* ifdef NDDS */
}
void ramsMasterSlaveJoint(int joint1, int joint2, int joint3, int joint4,
                int joint5, int joint6,
                int pscale, int onoff)
{
    printf("Joints selected: %d %d %d %d %d %d, pscale %d to turn %d\n",
        joint1, joint2, joint3, joint4, joint5, joint6, pscale, onoff);
#ifdef NDDS
    command->transitionCommand = MASTER_SLAVE_JOINTS_CHANGE;
    sprintf(command->current_mode, "master_slave_joints\n");
    sprintf(command->dest_mode, "master_slave_joints\n");
    command->trans_param.change_int[0] = joint1;
    command->trans_param.change_int[1] = joint2;
    command->trans_param.change_int[2] = joint3;
```

```
        command->trans_param.change_int[3] = joint4;
        command->trans_param.change_int[4] = joint5;
        command->trans_param.change_int[5] = joint6;
        command->trans_param.change_int[6] = pscale;
        command->trans_param.change_int[7] = onoff;
        NddsProducerSample(commandProducer);
        print_command();
        reset_trans_param();
#endif /* ifdef NDDS */
}
void ramsMasterSlaveTask(int coord1, int coord2, int coord3,
                int coord4, int coord5, int coord6,
                int pscale, int fscale, int onoff,
                int fonoff, int view)
{
    printf(
        "Coords selected: %d %d %d %d %d %d, posscale%d, frscale %d "
        "turn %d forceonoff %d view %d\n",
        coord1, coord2, coord3,
        coord4, coord5, coord6, pscale,
        fscale, onoff, fonoff, view);
#ifdef NDDS
    command->transitionCommand = MASTER_SLAVE_TASK_CHANGE;
    sprintf(command->current_mode, "master_slave_task\n");
    sprintf(command->dest_mode, "master_slave_task\n");
    command->trans_param.change_int[0] = coord1;
    command->trans_param.change_int[1] = coord2;
    command->trans_param.change_int[2] = coord3;
    command->trans_param.change_int[3] = coord4;
    command->trans_param.change_int[4] = coord5;
    command->trans_param.change_int[5] = coord6;
    command->trans_param.change_int[6] = pscale;
    command->trans_param.change_int[7] = fscale;
    command->trans_param.change_int[8] = fonoff;
    command->trans_param.change_int[9] = onoff;
    command->trans_param.change_int[10] = view;
    NddsProducerSample(commandProducer);
    print_command();
    reset_trans_param();
#endif /* ifdef NDDS */
} void ramsOpenSlaveManualJ()
{
```

A37

```
    printf("Open SlaveManualJ\n");
#ifdef NDDS
    command->transitionCommand = SLAVE_JOINTS_MANUAL;
    sprintf(command->current_mode, "idle\n");
    sprintf(command->dest_mode, "slave_joints_manual\n");
    NddsProducerSample(commandProducer);
    print_command();
#endif /* ifdef NDDS */
} void ramsOpenSlaveManualT()
{
    printf("Open SlaveManualT\n");
#ifdef NDDS
    command->transitionCommand = SLAVE_TASK_MANUAL;
    sprintf(command->current_mode, "idle\n");
    sprintf(command->dest_mode, "slave_task_manual\n");
    NddsProducerSample(commandProducer);
    print_command();
#endif /* ifdef NDDS */
} void ramsOpenSlaveAutomJ()
{
    printf("Open SlaveAutomJ(\n");
#ifdef NDDS
    command->transitionCommand = SLAVE_JOINTS_AUTO;
    sprintf(command->current_mode, "idle\n");
    sprintf(command->dest_mode, "slave_joints_auto\n");
    NddsProducerSample(commandProducer);
    print_command();
#endif /* ifdef NDDS */
} void ramsOpenSlaveAutomT()
{
    printf("Open SlaveAutomT\n");
#ifdef NDDS
    command->transitionCommand = SLAVE_TASK_AUTO;
    sprintf(command->current_mode, "idle\n");
    sprintf(command->dest_mode, "slave_task_auto\n");
    NddsProducerSample(commandProducer);
    print_command();
#endif /* ifdef NDDS */
```

A38

```
} void ramsOpenMasterManualJ()
{
    printf("Open MasterManualJ\n");
#ifdef NDDS
    command->transitionCommand = MASTER_JOINTS_MANUAL;
    sprintf(command->current_mode, "idle\n");
    sprintf(command->dest_mode, "master_joints_manual\n");
    NddsProducerSample(commandProducer);
    print_command();
#endif /* ifdef NDDS */
} void ramsOpenMasterAutomJ()
{
    printf("Open MasterAutomJ(\n");
#ifdef NDDS
    command->transitionCommand = MASTER_JOINTS_AUTO;
    sprintf(command->current_mode, "idle\n");
    sprintf(command->dest_mode, "master_joints_auto\n");
    NddsProducerSample(commandProducer);
    print_command();
#endif /* ifdef NDDS */
}
void ramsOpenMasterSprDamp()
{
    printf("Open MasterSprDamp\n");
#ifdef NDDS
    command->transitionCommand = MASTER_SPRING_DAMPER;
    sprintf(command->current_mode, "idle\n");
    sprintf(command->dest_mode, "master_spring_damper\n");
    NddsProducerSample(commandProducer);
    print_command();
#endif /* ifdef NDDS */
} void ramsOpenMasterSphere()
{
    printf("Open MasterSphere\n");
#ifdef NDDS
    command->transitionCommand = MASTER_SPHERE;
    sprintf(command->current_mode, "idle\n");
    sprintf(command->dest_mode, "master_sphere\n");
```

A39

```
    NddsProducerSample(commandProducer);
    print_command();
#endif /* ifdef NDDS */
} void ramsOpenMasterDemo()
{
    printf("Open MasterDemo\n");
#ifdef NDDS
    command->transitionCommand = MASTER_DEMO;
    sprintf(command->current_mode, "idle\n");
    sprintf(command->dest_mode, "master_demo\n");
    NddsProducerSample(commandProducer);
    print_command();
#endif /* ifdef NDDS */
} void ramsOpenMasterSlaveJoint()
{
    printf("Open MasterSlaveJoint\n");
#ifdef NDDS
    command->transitionCommand = MASTER_SLAVE_JOINTS;
    sprintf(command->current_mode, "idle\n");
    sprintf(command->dest_mode, "master_slave_joints\n");
    NddsProducerSample(commandProducer);
    print_command();
#endif /* ifdef NDDS */
} void ramsOpenMasterSlaveTask()
{
    printf("Open MasterSlaveTask\n");
#ifdef NDDS
    command->transitionCommand = MASTER_SLAVE_TASK;
    sprintf(command->current_mode, "idle\n");
    sprintf(command->dest_mode, "master_slave_task\n");
    NddsProducerSample(commandProducer);
    print_command();
#endif /* ifdef NDDS */
} void ramsCloseWin()
{
    printf("Close poped up window\n");
```

```c
#ifdef NDDS
    command->transitionCommand = RETURN_TO_IDLE;
    sprintf(command->current_mode, "any\n");
    sprintf(command->dest_mode, "idle\n");
    NddsProducerSample(commandProducer);
    print_command();
#endif /* ifdef NDDS */
} void ramsExit()
{
    printf("Ending session and exiting\n");
#ifdef NDDS
    command->transitionCommand = EXIT;
    sprintf(command->current_mode, "idle\n");
    sprintf(command->dest_mode, "quit\n");
    NddsProducerSample(commandProducer);
    print_command();
#endif /* ifdef NDDS */
}

DEF_CMD(applInit, {
    ramsInit(atoi(argv[1]));
})
DEF_CMD(applSlaveManualJ, {
    ramsSlaveManualJ(atoi(argv[1]), atoi(argv[2]));
})
DEF_CMD(applSlaveManualT, {
    ramsSlaveManualT(argv[1], atoi(argv[2]));
})
DEF_CMD(applSlaveAutomJ, {
    ramsSlaveAutomJ(atoi(argv[1]), atoi(argv[2]), atoi(argv[3]),
            atoi(argv[4]), atoi(argv[5]), atoi(argv[6]), atoi(argv[7]));
})
DEF_CMD(applSlaveAutomT, {
    ramsSlaveAutomT(atoi(argv[1]), atoi(argv[2]), atoi(argv[3]),
            atoi(argv[4]), atoi(argv[5]), atoi(argv[6]), atoi(argv[7]));
})
DEF_CMD(applMasterManualJ, {
    ramsMasterManualJ(atoi(argv[1]), atoi(argv[2]));
})
DEF_CMD(applMasterAutomJ, {
    ramsMasterAutomJ(atoi(argv[1]), atoi(argv[2]), atoi(argv[3]),
            atoi(argv[4]), atoi(argv[5]), atoi(argv[6]), atoi(argv[7]));
```

A41

```
    })
    DEF_CMD(applMasterSprDamp, {
        ramsMasterSprDamp(atoi(argv[1]), atoi(argv[2]), atoi(argv[3]),
                    atoi(argv[4]), atoi(argv[5]), atoi(argv[6]),
                    atoi(argv[7]), atoi(argv[8]), atoi(argv[9]));
    })
    DEF_CMD(applMasterSphere, {
        ramsMasterSphere(atoi(argv[1]), atoi(argv[2]), atoi(argv[3]),
                    atoi(argv[4]), atoi(argv[5]), atoi(argv[6]),
                    atoi(argv[7]), atoi(argv[8]), atoi(argv[9]),
                    atoi(argv[10]));
    })
    DEF_CMD(applMasterDemo, {
        ramsMasterDemo(argv[1], atoi(argv[2]));
    })
    DEF_CMD(applMasterSlaveJoint, {
        ramsMasterSlaveJoint(atoi(argv[1]), atoi(argv[2]), atoi(argv[3]),
                    atoi(argv[4]), atoi(argv[5]), atoi(argv[6]),
                    atoi(argv[7]), atoi(argv[8]));
    })
    DEF_CMD(applMasterSlaveTask, {
        ramsMasterSlaveTask(atoi(argv[1]), atoi(argv[2]), atoi(argv[3]),
                    atoi(argv[4]), atoi(argv[5]), atoi(argv[6]),
                    atoi(argv[7]), atoi(argv[8]), atoi(argv[9]),
                    atoi(argv[10]), atoi(argv[11]));
    })
    DEF_CMD(applOpenSlaveManualJ, {
        ramsOpenSlaveManualJ();
    })
    DEF_CMD(applOpenSlaveManualT, {
        ramsOpenSlaveManualT();
    })
    DEF_CMD(applOpenSlaveAutomJ, {
        ramsOpenSlaveAutomJ();
    })
    DEF_CMD(applOpenSlaveAutomT, {
        ramsOpenSlaveAutomT();
    })
    DEF_CMD(applOpenMasterManualJ, {
        ramsOpenMasterManualJ();
    })
    DEF_CMD(applOpenMasterAutomJ, {
        ramsOpenMasterAutomJ();
    })
```

A42

```
DEF_CMD(applOpenMasterSprDamp, {
    ramsOpenMasterSprDamp();
})
DEF_CMD(applOpenMasterSphere, {
    ramsOpenMasterSphere();
})
DEF_CMD(applOpenMasterDemo, {
    ramsOpenMasterDemo();
})
DEF_CMD(applOpenMasterSlaveJoint, {
    ramsOpenMasterSlaveJoint();
})
DEF_CMD(applOpenMasterSlaveTask, {
    ramsOpenMasterSlaveTask();
})
DEF_CMD(applCloseWin, {
    ramsCloseWin();
})
DEF_CMD(applExit, {
    ramsExit();
    Tcl_Eval(theInterpreter, "exit 0");
})
```

```
/*****************************************************************
 *    Copyright (c) 1993 Jet Propulsion Laboratory
 *    U.S. Government Sponsorship under NASA Contract NAS7-1270 is acknowledge
 *
 *    Author: Hari Das
 *
 *    $Id: rams_gui_main.c,v 1.1 1995/08/25 21:55:20 hari Exp hari $
 *    $Source: /home/hari/ram/software/tcl/rams/RCS/rams_gui_main.c,v $
 *    $Revision: 1.1 $
 *    $Date: 1995/08/25 21:55:20 $
 *    $Author: hari $
 *****************************************************************
 * $Log: rams_gui_main.c,v $
 * Revision 1.1  1995/08/25  21:55:20  hari
 * Initial revision
 *
 *
 */ static char rcsid[] = "$Id: rams_gui_main.c,v 1.1 1995/08/25 21:55:20 hari Exp hari $";

/***
   NAME
     rams_gui_main
   PURPOSE
     Main program to initialize and run the GUI for the RAMS
     master slave system demonstration.
   NOTES HISTORY
     Hari Das - Feb 28, 1995: Created.
***/
#include "rams_gui.h"

extern callbackFn newCommands[];
Tcl_Interp *theInterpreter;
#ifdef NDDS
extern void init_NDDS();
endif /* ifdef NDDS */ int main()
{
   int i;
```

```
    theInterpreter = Tcl_CreateInterp();

/* signal(SIGHUP, nop);*/
#ifdef NDDS
    init_NDDS();
endif /* ifdef NDDS */ if (Tcl_Init(theInterpreter) == TCL_ERROR) {
        printf("Tcl_Init ERROR: Aborting rams_gui\n");
        return TCL_ERROR;
    }

(void) Tk_CreateMainWindow(theInterpreter, 0, "Rams","Tk");

if (Tcl_Eval(theInterpreter,
                "source rams_command.tcl\n"
            ) != TCL_OK) {
        fprintf(stderr, "Internal error: configuration failed\n");
        exit(1);
    } for (i = 0; newCommands[i].name != NULL; i += 1)
        Tcl_CreateCommand(theInterpreter,
                    newCommands[i].name, newCommands[i].action,
                    0, NULL);
/*
Tcl_LinkVar(theInterpreter,"traverse",(char*)&traverse,TCL_LINK_INT);
*/
    Tk_MainLoop();

exit(0);
}
/*
            "rams_cmd .rams Rams Rams"
            "source rams_command.tcl\n"
            */
```

The NDDS Software Modules
/* RamsCommandMsg_producer.c \- A producer of data of type RamsCommandMsg This file is derived from code automatically generated by nddsgen.

modification history
--------------- ------
RTI,30may94,sas cleanup.
RTI,02apr94,gpc Auto-generated code template written.
*/ static char copyright_rti[] =
"(c) Copyright, Real-Time Innovations, Inc., 1994. All rights reserved.";

/*
DESCRIPTION:
Example producer of type RamsCommandMsg automatically generated by 'nddsgen'
To test them follow these steps:

(1) Compile this file and the example consumer.

(2) Start NDDS with nddsStartDaemon -d <domain> on the machines where
the test will be run. For more details see the man page on nddsStartDaemon.

(3) Make sure your environment variable NDDSHOME is set to at least
contain the machines where the test will be run.

(4) Start the producer on the same domain used for NDDS with the command
sun4/RamsCommandMsg_producer <domain>

(5) Start the consumer on the same domain used for NDDS with the command
sun4/RamsCommandMsg_producer <domain>

------------------------------------------------------------------------ */ include <stdio.h>
/*#include <stdlib.h> */
include "NDDS.h"
include "RamsCommandMsg.h"

void producerMain(int argc, char *argv[])
{
    register int i;

A46

```
int count, nddsDomain = 0;
unsigned int send_period_us = 4000000; /* 4 seconds */
NDDSProducer itemProducer;
RamsCommandMsg item1;
float persistence = 15.0f;
float strength = 1.0f;

if (argc >=2) {
    nddsDomain = atoi(argv[1]);
}

NddsInit(nddsDomain);
NddsVerbositySet(1);

RamsCommandMsgNddsRegister();

item1 = (RamsCommandMsg)calloc(1, sizeof(*item1));
printf("User Initialization of a RamsCommandMsg\n");
{
    /* Your initialization code goes here! */
    item1->current_mode = calloc(128,1);
    item1->dest_mode = calloc(128,1);
    item1->transitionCommand = 0;
    strcpy(item1->current_mode, "Test");
    strcpy(item1->dest_mode, "Test");
    for ( i=0; i<11; i++ ) {
        item1->trans_param.change_int[i] = i;
    }
    for ( i=0; i<6; i++ ) {
        item1->trans_param.change_flt[i] = 1.0 * i;
    }
} itemProducer = NddsProducerCreate("Producer", NDDS_ASYNCHRONOUS,
                    persistence, strength);

NddsProducerAddProduction(itemProducer, "RamsCommandMsg",
                "Example RamsCommandMsg", item1,
                0, NULL, NULL);

for (count=0;;count++) {
    printf("Sampling producer, count %d\n", count);
    NddsProducerSample(itemProducer);
    NddsUtilitySleep(send_period_us);
```

A47

```
        /* modify the data produced here */
        sprintf(item1->current_mode, "Test %d\n", count);
    }
} ifndef RTS_VXWORKS
void main(int argc, char *argv[])
{
    producerMain(argc, argv);
}
#endif
```

```
/* RamsCommandMsg_consumer.c \- A consumer of data of type RamsCommandMsg

This file is derived from code automatically generated by nddsgen.

modification history
------------ -------
RTI,30may94,sas cleanup.
RTI,02apr94,gpc Auto-generated code template written.
*/ static char copyright_rti[] =
"(c) Copyright, Real-Time Innovations, Inc., 1994. All rights reserved.";

/*
DESCRIPTION:
Example consumer of type RamsCommandMsg automatically generated by 'nddsgen'
To test them follow these steps:

(1) Compile this file and the example consumer.

(2) Start NDDS with nddsStartDaemon -d <domain> on the machines where
the test will be run. For more details see the man page on nddsStartDaemon.

(3) Make sure your environment variable NDDSHOME is set to at least
contain the machines where the test will be run.

(4) Start the producer on the same domain used for NDDS with the command
sun4/RamsCommandMsg_producer <domain>

(5) Start the consumer on the same domain used for NDDS with the command
sun4/RamsCommandMsg_producer <domain>

------------------------------------------------------------------- */ include <stdio.h>
/*#include <stdlib.h> */
include "NDDS.h"
include "RamsCommandMsg.h"

NDDSObjectInstance RamsCommandMsgCallback(NDDSUpdateInfo updateInfo)
{
    double now;
    RamsCommandMsg item = (RamsCommandMsg)updateInfo->instance;
```

```c
        printf("In callback function\n");
        now = NddsUtilityTimeGet();
        printf("*************************************************************\n"
            "[RamsCommandMsg callback:] update packet arrived! "
            "for \"%s\" of type \"%s\" STATUS: %s \n"
            "data produced at time %f, received at %f, now is %f difference "
            "is %f\n",
            updateInfo->name, updateInfo->type,
            nddsUpdateStatus[updateInfo->updateStatus],
            updateInfo->remoteTimeWhenProduced,
            updateInfo->localTimeWhenReceived, now,
            now - updateInfo->remoteTimeWhenProduced);

RamsCommandMsgPrint(item); /* This is does nothing by default. */ return updateInfo->instance;
} void consumerMain(int argc, char *argv[])
{
    int nddsDomain = 0;
    int us_per_second = 1000000;
    NDDSConsumer itemConsumer;
    float deadline = 10.0f;
    float min_separation = 0.0f;

if (argc >=2) {
        nddsDomain = atoi(argv[1]);
    }

NddsInit(nddsDomain);
    NddsVerbositySet(2);

RamsCommandMsgNddsRegister();

itemConsumer = NddsConsumerCreate("Consumer", NDDS_IMMEDIATE,
                        deadline, min_separation);

NddsConsumerAddSubscription(itemConsumer, "RamsCommandMsg",
                    "Example RamsCommandMsg", NULL,
                    RamsCommandMsgCallback, NULL);

while (1) {
```

```
        /* NddsConsumerPoll(itemConsumer);   Only needed if NDDS_POLLED */

/* We sleep only to kill time.  Nothing need be done here
           for an NDDS_IMMEDIATE consumer. */
        /* printf("Sleeping for %f sec...\n", deadline); */
        NddsUtilitySleep((unsigned int)us_per_second*deadline);
    }
} ifndef RTS_VXWORKS
void main(int argc, char *argv[])
{
    consumerMain(argc, argv);
}
#endif
```

A51

The TRANS Software Modules
```
/***************************************************************\
* Copyright (C) 1994, California Institute of Technology.
* U.S. Government Sponsorship under NASA Contract NAS7-918 is acknowledged.
*
* Author: Hari Das
*
* $Id: return_to_idle.cc,v 1.1 1995/08/08 15:30:57 hari Exp hari $

*$Source:/home/hari/ram/software/cntrlShell/rams/catexample/fsm/RCS/return_to_idle.cc,v
$
\***************************************************************/

/***
    NAME
       return_to_idle
    PURPOSE

NOTES

HISTORY
       Hari Das - Aug 8, 1995: Created.
***/

/************************************************************************
 * $Log: return_to_idle.cc,v $
// Revision 1.1  1995/08/08  15:30:57  hari
// Initial revision
//
 *
 */ ifdef rcsid
static char rcsid[] = "$Id: return_to_idle.cc,v 1.1 1995/08/08 15:30:57 hari Exp hari $";
#endif /* matches #ifdef rcsid */

/************************************************************************/
/* return_to_idle \- Transition module short description
     banner = -----------

Name: return_to_idle.cc
``` modification history
--------------------
rti,14May95,xxx Skeleton generated

DESCRIPTION:

Skeleton code segment for the return_to_idle transition module.
   Generated automatically by the ControlShell FSM Editor.

Do not modify by hand!
   This file should be copied to return_to_idle.cc,
   and the copy edited to suit your application.

FSM ENTRY FORMAT:

idle_config;          "<String>"
   source_state_config;  "<String>"
   dataIn_comp;          "<String>"

EXAMPLE:

<none>
================================================================================ */

```
#include <stdio.h>
include <stdlib.h>
#include <string.h>
include <math.h> include "rtilib/makeheader.h"
include "cs.h"

/* Additional Include Files, including your .fsm.h file for return codes */
#include "test_slave.fsm.h"
#include "rams.fsm.h"
#pragma begin_Package
#include "/home/hari/ram/software/cntrlShell/rams/components/dataio/dataIn.pkg.h"
pragma end_Package Public typedef class return_to_idleClass *return_to_idle;

Package
```

```
class return_to_idleClass : public TransRtnModuleClass { friend class return_to_idleParseClient;
 public:
   enum RETCODE {
       RET_OK,
       RET_FAIL,
   };

private:
   /* Additional private members and methods */
   dataInClass        *_dataIn;

protected:
   String         _idle_config;
   String         _source_state_config;
   String         _dataIn_comp;

/* Additional protected members and methods */ public:
   return_to_idleClass( CSFsm fsm, const char *modulename );
   ~return_to_idleClass();

virtual int execute();

virtual int getRetcode( char *retcodeName );
   virtual boolean print( int verbosity );
   virtual void *instance();

/* Additional public routines */ virtual const char *const className() { return ("return_to_idle"); }
};

return_to_idleClass::return_to_idleClass( CSFsm fsm, const char *modulename )
      : TransRtnModuleClass(fsm, modulename)
{
    /* Additional initialization code goes here. */
    _dataIn = NULL;
} return_to_idleClass::~return_to_idleClass()
```

A54

```
{
    /* Your destructor code goes here */
}
/*
 * This is the return_to_idle transition module's main routine.
 * It is called by the Finite State Machine.
 *
 * This should return the appropriate RETCODE return codes.
 */
int return_to_idleClass::execute()
{
    CSConfiguration config;

printf("Entering return_to_idle slave robot ...\n");
    printf("Source state is %s\n", _source_state_config);

if ( strncmp(_source_state_config, "real_slave_task_manual", 22) == 0) {
        CSFsmResetStimulus(_fsm, "manualSlaveTask = done", NULL);
    }
    else if ( strncmp(_source_state_config, "real_slave_joint_manual", 23) == 0) {
        CSFsmResetStimulus(_fsm, "manualSlaveJoint = done", NULL);
    }
    else if ( strncmp(_source_state_config, "real_slave_joint_auto", 21) == 0) {
        CSFsmResetStimulus(_fsm, "autoSlaveJoint = done", NULL);
    }
    else if ( strncmp(_source_state_config, "real_slave_task_auto", 20) == 0) {
        CSFsmResetStimulus(_fsm, "autoSlaveTask = done", NULL);
    }
    else if ( strncmp(_source_state_config, "real_master_joint_manual", 24) == 0) {
        CSFsmResetStimulus(_fsm, "manualMasterJoint = done", NULL);
    }
    else if ( strncmp(_source_state_config, "real_master_joint_auto", 22) == 0) {
        CSFsmResetStimulus(_fsm, "autoMasterJoint = done", NULL);
    }
    else if ( strncmp(_source_state_config, "real_master_sphere", 18) == 0) {
        CSFsmResetStimulus(_fsm, "sphereMasterSim = done", NULL);
    }
    else if ( strncmp(_source_state_config, "real_master_sprDamp", 19) == 0) {
        CSFsmResetStimulus(_fsm, "sprDampMasterSim = done", NULL);
    }
    else if ( strncmp(_source_state_config, "real_master_demo", 16) == 0) {
        CSFsmResetStimulus(_fsm, "demoMasterSim = done", NULL);
    }
```

A55

```c
    else if ( strncmp(_source_state_config, "real_master_slave_joint", 23) == 0) {
        CSFsmResetStimulus(_fsm, "masterSlaveJoint = done", NULL);
    }
    else if ( strncmp(_source_state_config, "real_master_slave_task", 22) == 0) {
        CSFsmResetStimulus(_fsm, "masterSlaveTask = done", NULL);
    } if ( _idle_config) {
        printf("Idle config is %s\n", _idle_config);
        config = (CSConfiguration)
            CSdBaseInquireRecord("CSConfiguration", _idle_config);
        if (!config) {
            fprintf(stderr, "%s: can't find configuration %s for %s\n",
                    className(), _idle_config, name());
            return(RET_FAIL);
        }
        printf("Activating idle config\n");
        _dataIn->controlPassive(1);
        config->activate();
    }
    CSFsmResetStimulus(_fsm, "returnToIdle = done", NULL);

printf("Leaving return_to_idle slave robot ...\n");
    return (RET_OK);
}

/*
 * return_to_idleClass::instance \- return_to_idle Instancing Routine
 *
 * This is called when a new instance of a return_to_idle
 * is to be created and installed into the system.
 *
 * If error, return NULL
 */
void *return_to_idleClass::instance()
{
    /* Your instancing code goes here */
    printf("Instancing return_to_idle\n");
    printf("    dataIn component is %s\n", _dataIn_comp);
    if ( !_dataIn_comp) {
        fprintf(stderr, "*** Error %s: _dataIn_comp name is NULL for %s",
                className(), name());
        return(NULL);
    }
```

A56

```
    _dataIn = (dataInClass *)
       CSdBaseInquireRecord("dataIn", _dataIn_comp);

if (_dataIn == NULL) {
       fprintf(stderr, "**** Error %s: Cannot find the %s "
              "dataIn for the %s "
              "transition module!\n",
              className(), _dataIn_comp, name());
       return(NULL);
    } return(this);
}
Package
void return_to_idleInitialize()
{
    /* Your initialization code for the entire class goes here. */
}

/* End of file */
```

```
/****************************************************************\
* Copyright (C) 1994, California Institute of Technology.
* U.S. Government Sponsorship under NASA Contract NAS7-918 is acknowledged.
*
* Author: Hari Das
*
* $Id: initialize_slave.cc,v 1.1 1995/08/08 15:28:19 hari Exp hari $

*$Source:/home/hari/ram/software/cntrlShell/rams/catexample/fsm/RCS/initialize_slave.cc,v
$
\****************************************************************/

/***
    NAME
      initialize_slave
    PURPOSE

NOTES

HISTORY
      Hari Das - Aug 8, 1995: Created.
***/

/****************************************************************
 * $Log: initialize_slave.cc,v $
// Revision 1.1  1995/08/08  15:28:19  hari
// Initial revision
//
 *
 */ ifdef rcsid
static char rcsid[] = "$Id: initialize_slave.cc,v 1.1 1995/08/08 15:28:19 hari Exp hari $";
#endif /* matches #ifdef rcsid */

/****************************************************************/
/* initialize_slave \- Transition module short description
    banner = -----------

Name: initialize_slave.cc modification history
```

```
--------------------
rti,20Jun95,xxx Skeleton generated
```

DESCRIPTION:

Skeleton code segment for the initialize_slave transition module.
Generated automatically by the ControlShell FSM Editor.

Do not modify by hand!
This file should be copied to initialize_slave.cc,
and the copy edited to suit your application.

FSM ENTRY FORMAT:

EXAMPLE:

<none>
```
===================================================
========================= */ include <stdio.h>
include <stdlib.h>
#include <string.h>
include <math.h> include "rtilib/makeheader.h"
include "cs.h"

#pragma begin_Public
extern "C" {
ifdef RTS_VXWORKS include <vxWorks.h>
include <taskLib.h>
#include <vxLib.h>
#include <errnoLib.h>
#include <sysLib.h>
#include <logLib.h>
#include <semLib.h>
#include <timers.h>
#include <ioLib.h>
#include <semSmLib.h>
```

A59

```
#include <smNameLib.h>
include <vme.h> ifdef ERIC_NEW
include "/home/paljug/vx/rams2/dt_interface.h"
#endif /* ERIC_NEW */
/* #include "/home/hari/ram/software/eric/dt_interface.h" */
#include "/home/paljug/vx/rams3/dt_interface.h"

#else
#include <string.h>
#endif /* RTS_VXWORKS */
#include "/home/hari/ram/software/cntrlShell/rams/components/slave/rams_slave.h"
}
pragma end_Public define WAIT_TIME    120

/* Additional Include Files, including your .fsm.h file for return codes */
#include "rams.fsm.h"

Public typedef class initialize_slaveClass *initialize_slave;

Package
class initialize_slaveClass : public TransRtnModuleClass { friend class initialize_slaveParseClient;
  public:
    enum RETCODE {
        RET_OK,
    };

private:
    /* Additional private members and methods */
    float gear_ratios[6];

protected:

/* Additional protected members and methods */ public:
    initialize_slaveClass( CSFsm fsm,  const char *modulename );
    ~initialize_slaveClass();
```

A60

```
    virtual int execute();

virtual int getRetcode( char *retcodeName );
    virtual boolean print( int verbosity );
    virtual void *instance();

/* Additional public routines */ virtual const char *const className() { return ("initialize_slave"); }
};

initialize_slaveClass::initialize_slaveClass( CSFsm fsm, const char *modulename )
    : TransRtnModuleClass(fsm, modulename)
{
    /* Additional initialization code goes here. */
} initialize_slaveClass::~initialize_slaveClass()
{
    /* Your destructor code goes here */
}

/*
 * This is the initialize_slave transition module's main routine.
 * It is called by the Finite State Machine.
 *
 * This should return the appropriate RETCODE return codes.
 */
int initialize_slaveClass::execute()
{
    printf("Entering initialize slave robot ...\n");

#ifdef RTS_VXWORKS
    register int i;
    /* float jointDisp[6]; */ i = 0;

printf("Waiting for initialization to complete ");
    while ((Is_PMAC_initialized() == ERROR)&&(i<WAIT_TIME)) {
        i++;
        taskDelay(60);
        printf(".");
```

A61

```
    }
    if ( i == WAIT_TIME) {
        printf("Initialization not completed\n");
        return(RET_OK);
    }
    else printf("Initialization completed\n");

printf("Power up slave amps NOW!\n");

taskDelay(1800);

amps_powered_up();

taskDelay(1800);

#endif /* ifdef RTS_VXWORKS */

CSFsmResetStimulus(_fsm, "initializeSlave = inactive", NULL);

printf("Leaving initialize slave robot ...\n");

return (RET_OK);
}

/*
 * initialize_slaveClass::instance \- initialize_slave Instancing Routine
 *
 * This is called when a new instance of a initialize_slave
 * is to be created and installed into the system.
 *
 * If error, return NULL
 */
void *initialize_slaveClass::instance()
{
    /* Your instancing code goes here */
    gear_ratios[0] = SLAVE_GEAR_RATIO1;
    gear_ratios[1] = SLAVE_GEAR_RATIO2;
    gear_ratios[2] = SLAVE_GEAR_RATIO3;
    gear_ratios[3] = SLAVE_GEAR_RATIO4;
    gear_ratios[4] = SLAVE_GEAR_RATIO5;
    gear_ratios[5] = SLAVE_GEAR_RATIO6;

return(this);
}
```

A62

```
Package
void initialize_slaveInitialize()
{
    /* Your initialization code for the entire class goes here. */
    initialize_servo();
}

/* End of file */
```

```
/*************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_cng_slave_task.cc,v 1.1 1995/08/08 15:26:38 hari Exp hari $
 *
 *                            $ S o u r c e :
 * /home/hari/ram/software/cntrlShell/rams/catexample/fsm/RCS/auto_cng_slave_task.cc,v $
 *
\*************************************************************/

/***
    NAME
      auto_cng_slave_task
    PURPOSE

NOTES

HISTORY
    Hari Das - Aug 8, 1995: Created.
***/

/*************************************************************
 * $Log: auto_cng_slave_task.cc,v $
// Revision 1.1  1995/08/08  15:26:38  hari
// Initial revision
//
 *
 */ ifdef rcsid
static char rcsid[] = "$Id: auto_cng_slave_task.cc,v 1.1 1995/08/08 15:26:38 hari Exp hari $";
#endif /* matches #ifdef rcsid */

/*************************************************************/
/* auto_cng_slave_task \- Transition module short description
   banner = -----------

Name: auto_cng_slave_task.cc
``` modification history
--------------------
rti,27Jun95,xxx Skeleton generated

DESCRIPTION:

Skeleton code segment for the auto_cng_slave_task transition module.
Generated automatically by the ControlShell FSM Editor.

Do not modify by hand!
This file should be copied to auto_cng_slave_task.cc,
and the copy edited to suit your application.

FSM ENTRY FORMAT:

```
autoTaskComp;       "<String>"
taskDiffComp;       "<String>"
```

EXAMPLE:

```
<none>
===================================================
============================== */ include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
extern "C" {
#include "/home/hari/ram/software/ndds/rams/RamsCommandMsg.h"
}
#include "/home/hari/ram/software/cntrlShell/rams/components/auto/auto_task.pkg.h"
#include "/home/hari/ram/software/cntrlShell/rams/components/sumblk/taskDiff.pkg.h"
pragma end_Package Public typedef class auto_cng_slave_taskClass *auto_cng_slave_task;
```

```
Package
class auto_cng_slave_taskClass : public TransRtnModuleClass { friend class auto_cng_slave_taskParseClient;
  public:
    enum RETCODE {
        RET_OK,
    };

private:
    /* Additional private members and methods */
    auto_taskClass    *_autoTaskIn;
    taskDiffClass     *_tdIn;

protected:
    String      _autoTaskComp;
    String      _taskDiffComp;

/* Additional protected members and methods */ public:
    auto_cng_slave_taskClass( CSFsm fsm, const char *modulename );
    ~auto_cng_slave_taskClass();

virtual int execute();

virtual int getRetcode( char *retcodeName );
    virtual boolean print( int verbosity );
    virtual void *instance();

/* Additional public routines */ virtual const char *const className() { return ("auto_cng_slave_task"); }
};

auto_cng_slave_taskClass::auto_cng_slave_taskClass( CSFsm fsm, const char *modulename
)
    : TransRtnModuleClass(fsm, modulename)
{
    /* Additional initialization code goes here. */
    _autoTaskIn = NULL;
    _tdIn = NULL;
}
```

A66

```
auto_cng_slave_taskClass::~auto_cng_slave_taskClass()
{
    /* Your destructor code goes here */
}

/*
 * This is the auto_cng_slave_task transition module's main routine.
 * It is called by the Finite State Machine.
 *
 * This should return the appropriate RETCODE return codes.
 */
int auto_cng_slave_taskClass::execute()
{
    RamsCommandMsg input;

printf("Entering auto_cng_task module ...\n");
    input = (RamsCommandMsg)NULL;

input = (RamsCommandMsg)CSFsmGetStimulusParameter(_fsm,
                            "autoTask");

if (input != NULL ) {
        printf("input != NULL, %d %d %d %d %d %d %d\n",
            input->trans_param.change_int[0],
            input->trans_param.change_int[1],
            input->trans_param.change_int[2],
            input->trans_param.change_int[3],
            input->trans_param.change_int[4],
            input->trans_param.change_int[5],
            input->trans_param.change_int[6]);
        _tdIn->taskDiffReset();
        _autoTaskIn->auto_task_change(
            input->trans_param.change_int[0],
            input->trans_param.change_int[1],
            input->trans_param.change_int[2],
            input->trans_param.change_int[3],
            input->trans_param.change_int[4],
            input->trans_param.change_int[5],
            input->trans_param.change_int[6]);
    }
    else {
        printf("input = NULL\n");
        _autoTaskIn->auto_task_change(0,0,0,0,0,0,0);
    }
```

```
    CSFsmResetStimulus(_fsm, "autoTask = idle", NULL);
    printf("Leaving auto_cng_task module ...\n");

return (RET_OK);
}

/*
 * auto_cng_slave_taskClass::instance \- auto_cng_slave_task Instancing Routine
 *
 * This is called when a new instance of a auto_cng_slave_task
 * is to be created and installed into the system.
 *
 * If error, return NULL
 */
void *auto_cng_slave_taskClass::instance()
{
    /* Your instancing code goes here */
    printf("Instancing setAutoSlaveTask\n");
    printf("   Auto task input component is %s\n", _autoTaskComp);
    if ( !_autoTaskComp) {
        fprintf(stderr, "*** Error %s: _autoTaskComp name is NULL for %s",
            className(), name());
        return(NULL);
    }

_autoTaskIn = (auto_taskClass *)
        CSdBaseInquireRecord("auto_task", _autoTaskComp);

if (_autoTaskIn == NULL) {
        fprintf(stderr, "*** Error %s: Cannot find the %s "
            "auto_task for the %s "
            "transition module!\n",
            className(), _autoTaskComp, name());
        return(NULL);
    }

/* Find taskDiff component */
    printf("   taskDiff component is %s\n", _taskDiffComp);
    if ( !_taskDiffComp) {
        fprintf(stderr, "*** Error %s: _taskDiff_comp name is NULL for %s",
            className(), name());
        return(NULL);
    }
```

A68

```
    _tdIn = (taskDiffClass *)
        CSdBaseInquireRecord("taskDiff", _taskDiffComp);

if (_tdIn == NULL) {
        fprintf(stderr, "*** Error %s: Cannot find the %s "
            "contMas master for the %s "
            "transition module!\n",
            className(), _taskDiffComp, name());
        return(NULL);
    } return(this);
}

Package
void auto_cng_slave_taskInitialize()
{
    /* Your initialization code for the entire class goes here. */
}

/* End of file */
```

```
/*************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_cng_slave_joint.cc,v 1.1 1995/08/08 15:25:57 hari Exp hari $
 *
 *                           $ S  o  u  r  c  e   :
 * /home/hari/ram/software/cntrlShell/rams/catexample/fsm/RCS/auto_cng_slave_joint.cc,v $
 *
\*************************************************************/

/***
   NAME
     auto_cng_slave_joint
   PURPOSE

NOTES

HISTORY
   Hari Das - Aug 8, 1995: Created.
***/

/*************************************************************
 * $Log: auto_cng_slave_joint.cc,v $
// Revision 1.1  1995/08/08  15:25:57  hari
// Initial revision
//
 *
 */ ifdef rcsid
static char rcsid[] = "$Id: auto_cng_slave_joint.cc,v 1.1 1995/08/08 15:25:57 hari Exp hari $";
#endif /* matches #ifdef rcsid */

/*************************************************************/
/* auto_cng_slave_joint \- Transition module short description
   banner = ----------

Name: auto_cng_slave_joint.cc
``` modification history
--------------------
rti,23Jun95,xxx Skeleton generated

DESCRIPTION:

Skeleton code segment for the auto_cng_slave_joint transition module.
Generated automatically by the ControlShell FSM Editor.

Do not modify by hand!
This file should be copied to auto_cng_slave_joint.cc,
and the copy edited to suit your application.

FSM ENTRY FORMAT:

autoJointComp;      "<String>"

EXAMPLE:

<none>
==================================================
========================== */

```
#include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
extern "C" {
#include "/home/hari/ram/software/ndds/rams/RamsCommandMsg.h"
}
#include "/home/hari/ram/software/cntrlShell/rams/components/auto/auto_joint.pkg.h"
pragma end_Package Public typedef class auto_cng_slave_jointClass *auto_cng_slave_joint;

Package
```

```
class auto_cng_slave_jointClass : public TransRtnModuleClass { friend class auto_cng_slave_jointParseClient;
  public:
    enum RETCODE {
        RET_OK,
    };

private:
    /* Additional private members and methods */
    auto_jointClass    *_autoJointIn;

protected:
    String          _autoJointComp;

/* Additional protected members and methods */ public:
    auto_cng_slave_jointClass( CSFsm fsm, const char *modulename );
    ~auto_cng_slave_jointClass();

virtual int execute();

virtual int getRetcode( char *retcodeName );
    virtual boolean print( int verbosity );
    virtual void *instance();

/* Additional public routines */ virtual const char *const className() { return ("auto_cng_slave_joint"); }
};

auto_cng_slave_jointClass::auto_cng_slave_jointClass(CSFsm fsm,const char *modulename
)
    : TransRtnModuleClass(fsm, modulename)
{
    /* Additional initialization code goes here. */
    _autoJointIn = NULL;
} auto_cng_slave_jointClass::~auto_cng_slave_jointClass()
{
    /* Your destructor code goes here */
```

A72

}
```
/*
 * This is the auto_cng_slave_joint transition module's main routine.
 * It is called by the Finite State Machine.
 *
 * This should return the appropriate RETCODE return codes.
 */
int auto_cng_slave_jointClass::execute()
{
    RamsCommandMsg input;

printf("Entering auto_cng_joint module ...\n");
    input = (RamsCommandMsg)NULL;

input = (RamsCommandMsg)CSFsmGetStimulusParameter(_fsm,
                            "autoJoint");

if (input != NULL ) {
        printf("input != NULL, %d %d %d %d %d %d %d\n",
            input->trans_param.change_int[0],
            input->trans_param.change_int[1],
            input->trans_param.change_int[2],
            input->trans_param.change_int[3],
            input->trans_param.change_int[4],
            input->trans_param.change_int[5],
            input->trans_param.change_int[6]);
        _autoJointIn->auto_joint_change(
            input->trans_param.change_int[0],
            input->trans_param.change_int[1],
            input->trans_param.change_int[2],
            input->trans_param.change_int[3],
            input->trans_param.change_int[4],
            input->trans_param.change_int[5],
            input->trans_param.change_int[6]);
    }
    else {
        printf("input = NULL\n");
        _autoJointIn->auto_joint_change(0,0,0,0,0,0,0);
    }

CSFsmResetStimulus(_fsm, "autoJoint = idle", NULL);
    printf("Leaving auto_cng_joint module ...\n");
```

```
    return (RET_OK);
}
/*
 * auto_cng_slave_jointClass::instance \- auto_cng_slave_joint Instancing Routine
 *
 * This is called when a new instance of a auto_cng_slave_joint
 * is to be created and installed into the system.
 *
 * If error, return NULL
 */
void *auto_cng_slave_jointClass::instance()
{
    /* Your instancing code goes here */
    printf("Auto joint input component is %s\n", _autoJointComp);
    if ( !_autoJointComp) {
        fprintf(stderr, "*** Error %s: _autoJointComp name is NULL for %s",
            className(), name());
        return(NULL);
    }

_autoJointIn = (auto_jointClass *)
        CSdBaseInquireRecord("auto_joint", _autoJointComp);

if (_autoJointIn == NULL) {
        fprintf(stderr, "*** Error %s: Cannot find the %s "
            "auto_joint for the %s "
            "transition module!\n",
            className(), _autoJointComp, name());
        return(NULL);
    }
    return(this);
}

Package
void auto_cng_slave_jointInitialize()
{
    /* Your initialization code for the entire class goes here. */
}

/* End of file */
```

```
/***********************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_slave_joint.cc,v 1.1 1995/08/08 15:26:49 hari Exp hari $
 *
 *                        $ S  o   u   r   c   e    :
 /home/hari/ram/software/cntrlShell/rams/catexample/fsm/RCS/auto_slave_joint.cc,v $
 *
\***********************************************************************/

/***
   NAME
     auto_slave_joint
   PURPOSE

NOTES

HISTORY
     Hari Das - Aug 8, 1995: Created.
***/

/************************************************************************
 * $Log: auto_slave_joint.cc,v $
// Revision 1.1  1995/08/08  15:26:49  hari
// Initial revision
//
 *
 */ ifdef rcsid
static char rcsid[] = "$Id: auto_slave_joint.cc,v 1.1 1995/08/08 15:26:49 hari Exp hari $";
#endif /* matches #ifdef rcsid */

/************************************************************************/
/* auto_slave_joint \- Transition module short description
     banner = -----------

Name: auto_slave_joint.cc
``` modification history
--------------------
rti,23Jun95,xxx Skeleton generated

DESCRIPTION:

Skeleton code segment for the auto_slave_joint transition module.
  Generated automatically by the ControlShell FSM Editor.

Do not modify by hand!
  This file should be copied to auto_slave_joint.cc,
  and the copy edited to suit your application.

FSM ENTRY FORMAT:

auto_joint_config;   "<String>"
  autoJointComp;       "<String>"

EXAMPLE:

<none>
================================================================
============================= */

```
#include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
#include "/home/hari/ram/software/cntrlShell/rams/components/auto/auto_joint.pkg.h"
pragma end_Package Public typedef class auto_slave_jointClass *auto_slave_joint;

Package
class auto_slave_jointClass : public TransRtnModuleClass {
```

```
friend class auto_slave_jointParseClient;
public:
   enum RETCODE {
      RET_OK,
      RET_FAIL,
   };

private:
   /* Additional private members and methods */
   auto_jointClass   *_autoJointIn;

protected:
   String      _auto_joint_config;
   String         _autoJointComp;

/* Additional protected members and methods */ public:
   auto_slave_jointClass( CSFsm fsm, const char *modulename );
   ~auto_slave_jointClass();

virtual int execute();

virtual int getRetcode( char *retcodeName );
   virtual boolean print( int verbosity );
   virtual void *instance();

/* Additional public routines */ virtual const char *const className() { return ("auto_slave_joint"); }
};

auto_slave_jointClass::auto_slave_jointClass( CSFsm fsm, const char *modulename )
   : TransRtnModuleClass(fsm, modulename)
{
   /* Additional initialization code goes here. */
   _autoJointIn = NULL;
} auto_slave_jointClass::~auto_slave_jointClass()
{
   /* Your destructor code goes here */
}
```

```
/*
 * This is the auto_slave_joint transition module's main routine.
 * It is called by the Finite State Machine.
 *
 * This should return the appropriate RETCODE return codes.
 */
int auto_slave_jointClass::execute()
{
    CSConfiguration config;

printf("Entering autoSlaveJoint slave robot ...\n");
    if ( _auto_joint_config) {
        config = (CSConfiguration)
            CSdBaseInquireRecord("CSConfiguration",_auto_joint_config);
        if (!config) {
            fprintf(stderr, "%s: can't find configuration %s for %s\n",
                    className(), _auto_joint_config, name());
            return(RET_FAIL);
        }
        _autoJointIn->auto_joint_reset();
        config->activate();
    }
    printf("Leaving autoSlaveJoint slave robot ...\n");
    return (RET_OK);
}

/*
 * auto_slave_jointClass::instance \- auto_slave_joint Instancing Routine
 *
 * This is called when a new instance of a auto_slave_joint
 * is to be created and installed into the system.
 *
 * If error, return NULL
 */
void *auto_slave_jointClass::instance()
{
    /* Your instancing code goes here */
    printf("Auto joint input component is %s\n", _autoJointComp);
    if ( !_autoJointComp) {
        fprintf(stderr, "*** Error %s: _autoJointComp name is NULL for %s",
                className(), name());
        return(NULL);
    }
```

A78

```
    _autoJointIn = (auto_jointClass *)
       CSdBaseInquireRecord("auto_joint", _autoJointComp);

if (_autoJointIn == NULL) {
       fprintf(stderr, "*** Error %s: Cannot find the %s "
           "test_task_input for the %s "
           "transition module!\n",
           className(), _autoJointComp, name());
       return(NULL);
    } return(this);
}

Package
void auto_slave_jointInitialize()
{
    /* Your initialization code for the entire class goes here. */
}

/* End of file */
```

```
/*********************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_slave_task.cc,v 1.1 1995/08/08 15:27:01 hari Exp hari $
 *
 *                          $    S    o    u    r    c    e    :
 * /home/hari/ram/software/cntrlShell/rams/catexample/fsm/RCS/auto_slave_task.cc,v $
 *
\*********************************************************************/

/***
    NAME
      auto_slave_task
    PURPOSE

NOTES

HISTORY
      Hari Das - Aug 8, 1995: Created.
***/

/*********************************************************************
 * $Log: auto_slave_task.cc,v $
// Revision 1.1  1995/08/08  15:27:01  hari
// Initial revision
//
 *
 */ ifdef rcsid
static char rcsid[] = "$Id: auto_slave_task.cc,v 1.1 1995/08/08 15:27:01 hari Exp hari $";
#endif /* matches #ifdef rcsid */

/*********************************************************************/
/* auto_slave_task \- Transition module short description
    banner = ----------

Name: auto_slave_task.cc
```

```
modification history
--------------------
rti,27Jun95,xxx Skeleton generated

DESCRIPTION:

Skeleton code segment for the auto_slave_task transition module.
    Generated automatically by the ControlShell FSM Editor.

Do not modify by hand!
    This file should be copied to auto_slave_task.cc,
    and the copy edited to suit your application.

FSM ENTRY FORMAT:

auto_task_config;    "<String>"
    autoTaskComp;        "<String>"
    taskDiffComp;        "<String>"

EXAMPLE:

<none>
==========================================================
============================== */ include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
#include "/home/hari/ram/software/cntrlShell/rams/components/auto/auto_task.pkg.h"
#include "/home/hari/ram/software/cntrlShell/rams/components/sumblk/taskDiff.pkg.h"
pragma end_Package Public typedef class auto_slave_taskClass *auto_slave_task;

Package
```

```
class auto_slave_taskClass : public TransRtnModuleClass { friend class auto_slave_taskParseClient;
  public:
    enum RETCODE {
        RET_OK,
        RET_FAIL,
    };

private:
    /* Additional private members and methods */
    auto_taskClass    *_autoTaskIn;
    taskDiffClass       *_tdIn;

protected:
    String      _auto_task_config;
    String        _autoTaskComp;
    String        _taskDiffComp;

/* Additional protected members and methods */ public:
    auto_slave_taskClass( CSFsm fsm, const char *modulename );
    ~auto_slave_taskClass();

virtual int execute();

virtual int getRetcode( char *retcodeName );
    virtual boolean print( int verbosity );
    virtual void *instance();

/* Additional public routines */ virtual const char *const className() { return ("auto_slave_task"); }
};

auto_slave_taskClass::auto_slave_taskClass( CSFsm fsm, const char *modulename )
    : TransRtnModuleClass(fsm, modulename)
{
    /* Additional initialization code goes here. */
} auto_slave_taskClass::~auto_slave_taskClass()
```

A82

```
{
    /* Your destructor code goes here */
    _autoTaskIn = NULL;
    _tdIn = NULL;
}

/*
 * This is the auto_slave_task transition module's main routine.
 * It is called by the Finite State Machine.
 *
 * This should return the appropriate RETCODE return codes.
 */
int auto_slave_taskClass::execute()
{
    CSConfiguration config;

printf("Entering autoSlaveTask slave robot ...\n");
    if ( _auto_task_config) {
        config = (CSConfiguration)
            CSdBaseInquireRecord("CSConfiguration", _auto_task_config);
        if (!config) {
            fprintf(stderr, "%s: can't find configuration %s for %s\n",
                    className(), _auto_task_config, name());
            return(RET_FAIL);
        }
        _autoTaskIn->auto_task_reset();
        _tdIn->taskDiffReset();
        config->activate();
    }
    printf("Leaving autoSlaveTask slave robot ...\n");
    return (RET_OK);
}

/*
 * auto_slave_taskClass::instance \- auto_slave_task Instancing Routine
 *
 * This is called when a new instance of a auto_slave_task
 * is to be created and installed into the system.
 *
 * If error, return NULL
 */
void *auto_slave_taskClass::instance()
{
    /* Your instancing code goes here */
```

```
    printf("Instancing autoSlaveTask\n");
    printf("   Auto task input component is %s\n", _autoTaskComp);
    if ( !_autoTaskComp) {
        fprintf(stderr, "*** Error %s: _autoTaskComp name is NULL for %s",
            className(), name());
        return(NULL);
    }

_autoTaskIn = (auto_taskClass *)
        CSdBaseInquireRecord("auto_task", _autoTaskComp);

if (_autoTaskIn == NULL) {
        fprintf(stderr, "*** Error %s: Cannot find the %s "
            "test_task_input for the %s "
            "transition module!\n",
            className(), _autoTaskComp, name());
        return(NULL);
    }

/* Find taskDiff component */
    printf("   taskDiff component is %s\n", _taskDiffComp);
    if ( !_taskDiffComp) {
        fprintf(stderr, "*** Error %s: _taskDiff_comp name is NULL for %s",
            className(), name());
        return(NULL);
    }

_tdIn = (taskDiffClass *)
        CSdBaseInquireRecord("taskDiff", _taskDiffComp);

if (_tdIn == NULL) {
        fprintf(stderr, "*** Error %s: Cannot find the %s "
            "contMas master for the %s "
            "transition module!\n",
            className(), _taskDiffComp, name());
        return(NULL);
    } return(this);
}

Package
void auto_slave_taskInitialize()
{
```

```
    /* Your initialization code for the entire class goes here. */
}

/* End of file */
```

```
/******************************************************************\
* Copyright (C) 1994, California Institute of Technology.
* U.S. Government Sponsorship under NASA Contract NAS7-918 is acknowledged.
*
* Author: Hari Das
*
* $Id: manual_slave_task.cc,v 1.1 1995/08/08 15:28:37 hari Exp hari $
*
*                         $ Source :
/home/hari/ram/software/cntrlShell/rams/catexample/fsm/RCS/manual_slave_task.cc,v $
*
\******************************************************************/

/***
   NAME
     manual_slave_task
   PURPOSE

NOTES

HISTORY
     Hari Das - Aug 8, 1995: Created.
***/

/**********************************************************************
 * $Log: manual_slave_task.cc,v $
// Revision 1.1  1995/08/08  15:28:37  hari
// Initial revision
//
 *
 */ ifdef rcsid
static char rcsid[] = "$Id: manual_slave_task.cc,v 1.1 1995/08/08 15:28:37 hari Exp hari $";
#endif /* matches #ifdef rcsid */

/**********************************************************************/
/* manual_slave_task \- Transition module short description
   banner = -----------

Name: manual_slave_task.cc
``` modification history
--------------------
rti,22Jun95,xxx Skeleton generated

DESCRIPTION:

Skeleton code segment for the manual_slave_task transition module.
Generated automatically by the ControlShell FSM Editor.

Do not modify by hand!
This file should be copied to manual_slave_task.cc,
and the copy edited to suit your application.

FSM ENTRY FORMAT:

```
task_config;        "<String>"
task_comp_in;       "<String>"
taskDiffComp;       "<String>"
```

EXAMPLE:

```
<none>
================================================================
=========================== */
```

```c
#include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
#include "/home/hari/ram/software/cntrlShell/rams/components/keybdin/test_task_input.pkg.h"
#include "/home/hari/ram/software/cntrlShell/rams/components/sumblk/taskDiff.pkg.h"
pragma end_Package Public typedef class manual_slave_taskClass *manual_slave_task;
```

A87

```
Package
class manual_slave_taskClass : public TransRtnModuleClass { friend class manual_slave_taskParseClient;
  public:
    enum RETCODE {
        RET_OK,
        RET_FAIL,
    };

private:
    /* Additional private members and methods */
    test_task_inputClass   *_taskIn;
    taskDiffClass          *_tdIn;

protected:
    String        _task_config;
    String        _task_comp_in;
    String        _taskDiffComp;

/* Additional protected members and methods */ public:
    manual_slave_taskClass( CSFsm fsm, const char *modulename );
    ~manual_slave_taskClass();

virtual int execute();

virtual int getRetcode( char *retcodeName );
    virtual boolean print( int verbosity );
    virtual void *instance();

/* Additional public routines */ virtual const char *const className() { return ("manual_slave_task"); }
};

manual_slave_taskClass::manual_slave_taskClass( CSFsm fsm, const char *modulename )
    : TransRtnModuleClass(fsm, modulename)
{
    /* Additional initialization code goes here. */
    _taskIn = NULL;
    _tdIn = NULL;
```

}

```
manual_slave_taskClass::~manual_slave_taskClass()
{
    /* Your destructor code goes here */
}

/*
 * This is the manual_slave_task transition module's main routine.
 * It is called by the Finite State Machine.
 *
 * This should return the appropriate RETCODE return codes.
 */
int manual_slave_taskClass::execute()
{
    CSConfiguration config;

printf("Entering manualSlaveTask slave robot ...\n");
    if ( _task_config) {
        config = (CSConfiguration)
            CSdBaseInquireRecord("CSConfiguration", _task_config);
        if (!config) {
            fprintf(stderr, "%s: can't find configuration %s for %s\n",
                    className(), _task_config, name());
            return(RET_FAIL);
        }
        _taskIn->taskReset();
        _tdIn->taskDiffReset();
        config->activate();
    }
    printf("Leaving manualSlaveTask slave robot ...\n");
    return (RET_OK);
}

/*
 * manual_slave_taskClass::instance \- manual_slave_task Instancing Routine
 *
 * This is called when a new instance of a manual_slave_task
 * is to be created and installed into the system.
 *
 * If error, return NULL
 */
void *manual_slave_taskClass::instance()
{
```

A89

```
/* Your instancing code goes here */
printf("Instancing manualSlaveTask\n");
printf("   Task input component is %s\n", _task_comp_in);
if ( !_task_comp_in) {
    fprintf(stderr, "*** Error %s: _task_comp_in name is NULL for %s",
        className(), name());
    return(NULL);
}

_taskIn = (test_task_inputClass *)
    CSdBaseInquireRecord("test_task_input", _task_comp_in);

if (_taskIn == NULL) {
    fprintf(stderr, "*** Error %s: Cannot find the %s "
        "test_task_input for the %s "
        "transition module!\n",
        className(), _task_comp_in, name());
    return(NULL);
}

/* Find taskDiff component */
printf("   taskDiff component is %s\n", _taskDiffComp);
if ( !_taskDiffComp) {
    fprintf(stderr, "*** Error %s: _taskDiff_comp name is NULL for %s",
        className(), name());
    return(NULL);
}

_tdIn = (taskDiffClass *)
    CSdBaseInquireRecord("taskDiff", _taskDiffComp);

if (_tdIn == NULL) {
    fprintf(stderr, "*** Error %s: Cannot find the %s "
        "contMas master for the %s "
        "transition module!\n",
        className(), _taskDiffComp, name());
    return(NULL);
}
    return(this);
}
Package
void manual_slave_taskInitialize()
{
    /* Your initialization code for the entire class goes here. */
```

A90

```
}
/* End of file */
```

```
/***********************************************************************\
 * Copyright (C) 1994, California Institute of Technology.
 * U.S. Government Sponsorship under NASA Contract NAS7-918 is acknowledged.
 *
 * Author: Hari Das
 *
 * $Id: manual_slave_joint.cc,v 1.1 1995/08/08 15:28:50 hari Exp hari $
 *
 *                          $ Source :
 * /home/hari/ram/software/cntrlShell/rams/catexample/fsm/RCS/manual_slave_joint.cc,v $
 *
\***********************************************************************/

/***
    NAME
      manual_slave_joint
    PURPOSE

NOTES

HISTORY
      Hari Das - Aug 8, 1995: Created.
***/

/************************************************************************
 * $Log: manual_slave_joint.cc,v $
// Revision 1.1  1995/08/08  15:28:50  hari
// Initial revision
//
 *
 */ ifdef rcsid
static char rcsid[] = "$Id: manual_slave_joint.cc,v 1.1 1995/08/08 15:28:50 hari Exp hari $";
#endif /* matches #ifdef rcsid */

/************************************************************************/
/* manual_slave_joint \- Transition module short description
   banner = ----------

Name: manual_slave_joint.cc
```

```
modification history
--------------------
rti,22Jun95,xxx Skeleton generated

DESCRIPTION:

Skeleton code segment for the manual_slave_joint transition module.
    Generated automatically by the ControlShell FSM Editor.

Do not modify by hand!
    This file should be copied to manual_slave_joint.cc,
    and the copy edited to suit your application.

FSM ENTRY FORMAT:

joint_config;      "<String>"

EXAMPLE:

<none>
==================================================
========================== */ include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"

Public typedef class manual_slave_jointClass *manual_slave_joint;

Package
class manual_slave_jointClass : public TransRtnModuleClass { friend class manual_slave_jointParseClient;
  public:
    enum RETCODE {
        RET_OK,
```

A93

RET_FAIL,
};

private:
    /* Additional private members and methods */ protected:
    String          _joint_config;

/* Additional protected members and methods */ public:
    manual_slave_jointClass( CSFsm fsm, const char *modulename );
    ~manual_slave_jointClass();

virtual int execute();

virtual int getRetcode( char *retcodeName );
    virtual boolean print( int verbosity );
    virtual void *instance();

/* Additional public routines */ virtual const char *const className() { return ("manual_slave_joint"); }
};

manual_slave_jointClass::manual_slave_jointClass( CSFsm fsm, const char *modulename )
    : TransRtnModuleClass(fsm, modulename)
{
    /* Additional initialization code goes here. */
} manual_slave_jointClass::~manual_slave_jointClass()
{
    /* Your destructor code goes here */
}

/*
 * This is the manual_slave_joint transition module's main routine.
 * It is called by the Finite State Machine.
 *
 * This should return the appropriate RETCODE return codes.
 */

A94

```
int manual_slave_jointClass::execute()
{
   CSConfiguration config;

printf("Entering manualSlaveJoint slave robot ...\n");
   if ( _joint_config) {
      config = (CSConfiguration)
         CSdBaseInquireRecord("CSConfiguration", _joint_config);
      if (!config) {
         fprintf(stderr, "%s: can't find configuration %s for %s\n",
            className(), _joint_config, name());
         return(RET_FAIL);
      }
      config->activate();
   }
   printf("Leaving manualSlaveJoint slave robot ...\n");
   return (RET_OK);
}

/*
 * manual_slave_jointClass::instance \- manual_slave_joint Instancing Routine
 *
 * This is called when a new instance of a manual_slave_joint
 * is to be created and installed into the system.
 *
 * If error, return NULL
 */
void *manual_slave_jointClass::instance()
{
   /* Your instancing code goes here */ return(this);
}

Package
void manual_slave_jointInitialize()
{
   /* Your initialization code for the entire class goes here. */
}

/* End of file */
```

```
/***********************************************************************\
 * Copyright (C) 1994, California Institute of Technology.
 * U.S. Government Sponsorship under NASA Contract NAS7-918 is acknowledged.
 *
 * Author: Hari Das
 *
 * $Id: control_slave_joint.cc,v 1.1 1995/08/08 15:27:15 hari Exp hari $
 *
 *                            $     S     o     u     r     c     e     :
 * /home/hari/ram/software/cntrlShell/rams/catexample/fsm/RCS/control_slave_joint.cc,v $
 *
\***********************************************************************/

/***
   NAME
     control_slave_joint
   PURPOSE

NOTES

HISTORY
   Hari Das - Aug 8, 1995: Created.
***/

/************************************************************************
 * $Log: control_slave_joint.cc,v $
// Revision 1.1  1995/08/08  15:27:15  hari
// Initial revision
//
 *
 */ ifdef rcsid
static char rcsid[] = "$Id: control_slave_joint.cc,v 1.1 1995/08/08 15:27:15 hari Exp hari $";
#endif /* matches #ifdef rcsid */

/************************************************************************/
/* control_slave_joint \- Transition module short description
   banner = ----------

Name: control_slave_joint.cc
```

```
modification history
--------------------
rti,20Jun95,xxx Skeleton generated
```

DESCRIPTION:

Skeleton code segment for the control_slave_joint transition module.
Generated automatically by the ControlShell FSM Editor.

Do not modify by hand!
This file should be copied to control_slave_joint.cc,
and the copy edited to suit your application.

FSM ENTRY FORMAT:

jointInputComp;    "<String>"

EXAMPLE:

<none>
```
===========================================
========================= */ include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
extern "C" {
#include "/home/hari/ram/software/cntrlShell/rams/catexample/consts.h"
#include "/home/hari/ram/software/ndds/rams/RamsCommandMsg.h"
}
#include "/home/hari/ram/software/cntrlShell/rams/components/keybdin/test_joints_input.pkg.h"
#pragma end_Package
```

Public typedef class control_slave_jointClass *control_slave_joint;

Package
class control_slave_jointClass : public TransRtnModuleClass {

```
friend class control_slave_jointParseClient;
  public:
    enum RETCODE {
        RET_OK,
    };

private:
    /* Additional private members and methods */
    test_joints_inputClass *_jointIn;

protected:
    String         _jointInputComp;

/* Additional protected members and methods */ public:
    control_slave_jointClass( CSFsm fsm, const char *modulename );
    ~control_slave_jointClass();

virtual int execute();

virtual int getRetcode( char *retcodeName );
    virtual boolean print( int verbosity );
    virtual void *instance();

/* Additional public routines */ virtual const char *const className() { return ("control_slave_joint"); }
};

control_slave_jointClass::control_slave_jointClass( CSFsm fsm, const char *modulename )
    : TransRtnModuleClass(fsm, modulename)
{
    /* Additional initialization code goes here. */
    _jointIn = NULL;

}
```

A98

```
control_slave_jointClass::~control_slave_jointClass()
{
    /* Your destructor code goes here */
}

/*
 * This is the control_slave_joint transition module's main routine.
 * It is called by the Finite State Machine.
 *
 * This should return the appropriate RETCODE return codes.
 */
int control_slave_jointClass::execute()
{
    RamsCommandMsg input;

printf("Entering control_joint module ...\n");
    input = (RamsCommandMsg)NULL;
    input = (RamsCommandMsg)CSFsmGetStimulusParameter(_fsm,
                            "jointSlaveControl");
    if (input != NULL ) {
        printf("input != NULL, joint=%d, increment=%d\n",
            input->trans_param.change_int[0],
            input->trans_param.change_int[1]);
        _jointIn->jointChange(
            input->trans_param.change_int[0] - 1,
            ((float)input->trans_param.change_int[1])/
            JOINT_MANUAL_SCALE_PARAM);
    }
    else {
        printf("input = NULL, joint=%d, increment=%d\n",
            input->trans_param.change_int[0],
            input->trans_param.change_int[1]);
        _jointIn->jointChange(1, 0.01);
    }

CSFsmResetStimulus(_fsm, "jointSlaveControl = idle", NULL);
    printf("Leaving control_joint module ...\n");

return (RET_OK);
}

/*
 * control_slave_jointClass::instance \- control_slave_joint Instancing Routine
 *
```

A99

```
 * This is called when a new instance of a control_slave_joint
 * is to be created and installed into the system.
 *
 * If error, return NULL
 */
void *control_slave_jointClass::instance()
{
    /* Your instancing code goes here */ printf("Joint input component is %s\n", _jointInputComp);
    if ( !_jointInputComp) {
        fprintf(stderr, "*** Error %s: _jointInputComp name is NULL for %s",
                className(), name());
        return(NULL);
    }

_jointIn = (test_joints_inputClass *)
        CSdBaseInquireRecord("test_joints_input", _jointInputComp);

if (_jointIn == NULL) {
        fprintf(stderr, "*** Error %s: Cannot find the %s "
                "test_joints_input for the %s "
                "transition module!\n",
                className(), _jointInputComp, name());
        return(NULL);
    }
    return(this);
}

Package
void control_slave_jointInitialize()
{
    /* Your initialization code for the entire class goes here. */
}

/* End of file */
```

A100

```
/*********************************************************************\
 * Copyright (C) 1994, California Institute of Technology.
 * U.S. Government Sponsorship under NASA Contract NAS7-918 is acknowledged.
 *
 * Author: Hari Das
 *
 * $Id: control_slave_task.cc,v 1.1 1995/08/08 15:27:26 hari Exp hari $
 *                              $ Source :
 * /home/hari/ram/software/cntrlShell/rams/catexample/fsm/RCS/control_slave_task.cc,v $
 *
\*********************************************************************/

/***
    NAME
      control_slave_task
    PURPOSE

NOTES

HISTORY
      Hari Das - Aug 8, 1995: Created.
***/

/*********************************************************************
 * $Log: control_slave_task.cc,v $
// Revision 1.1  1995/08/08  15:27:26  hari
// Initial revision
//
 *
 */ ifdef rcsid
static char rcsid[] = "$Id: control_slave_task.cc,v 1.1 1995/08/08 15:27:26 hari Exp hari $";
#endif /* matches #ifdef rcsid */

/*********************************************************************/
/* control_slave_task \- Transition module short description
   banner = ----------

Name: control_slave_task.cc
``` modification history
--------------------
rti,20Jun95,xxx Skeleton generated

DESCRIPTION:

Skeleton code segment for the control_slave_task transition module.
Generated automatically by the ControlShell FSM Editor.

Do not modify by hand!
This file should be copied to control_slave_task.cc,
and the copy edited to suit your application.

FSM ENTRY FORMAT:

taskInputComp;    "<String>"
    taskDiffComp;    "<String>"

EXAMPLE:

<none>
==========================================================
=========================== */

```
#include <stdio.h>
include <stdlib.h>
#include <string.h>
include <math.h> include "rtilib/makeheader.h"
include "cs.h"

/* Additional Include Files, including your .fsm.h file for return codes */
#include "rams.fsm.h"
#pragma begin_Package
extern "C" {
#include "/home/hari/ram/software/cntrlShell/rams/catexample/consts.h"
#include "/home/hari/ram/software/ndds/rams/RamsCommandMsg.h"
}
#include "/home/hari/ram/software/cntrlShell/rams/components/keybdin/test_task_input.pkg.h"
#include "/home/hari/ram/software/cntrlShell/rams/components/sumblk/taskDiff.pkg.h"
pragma end_Package
```

```
Public typedef class control_slave_taskClass *control_slave_task;

Package
class control_slave_taskClass : public TransRtnModuleClass { friend class control_slave_taskParseClient;
  public:
    enum RETCODE {
        RET_OK,
    };

private:
    /* Additional private members and methods */
    test_task_inputClass   *_taskIn;
    taskDiffClass          *_tdIn;

protected:
    String          _taskInputComp;
    String          _taskDiffComp;

/* Additional protected members and methods */ public:
    control_slave_taskClass( CSFsm fsm, const char *modulename );
    ~control_slave_taskClass();

virtual int execute();

virtual int getRetcode( char *retcodeName );
    virtual boolean print( int verbosity );
    virtual void *instance();

/* Additional public routines */ virtual const char *const className() { return ("control_slave_task"); }
};

control_slave_taskClass::control_slave_taskClass( CSFsm fsm, const char *modulename )
    : TransRtnModuleClass(fsm, modulename)
{
    /* Additional initialization code goes here. */
    _taskIn = NULL;
```

```
    _tdIn = NULL;
} control_slave_taskClass::~control_slave_taskClass()
{
    /* Your destructor code goes here */
}

/*
 * This is the control_slave_task transition module's main routine.
 * It is called by the Finite State Machine.
 *
 * This should return the appropriate RETCODE return codes.
 */
int control_slave_taskClass::execute()
{
    RamsCommandMsg input;

printf("Entering control_task module ...\n");
    input = (RamsCommandMsg)NULL;

input = (RamsCommandMsg)CSFsmGetStimulusParameter(_fsm,
                            "taskSlaveControl");

if (input != NULL ) {
        printf("input != NULL, joint=%d, increment=%d\n",
            input->trans_param.change_int[0],
            input->trans_param.change_int[1]);
        /* _tdIn->taskDiffReset(); */
        _taskIn->taskChange(
            input->trans_param.change_int[0] - 1,
            ((float)input->trans_param.change_int[1])/
            TASK_MANUAL_SCALE_PARAM);
    }
    else {
        printf("input = NULL, joint=%d, increment=%d\n",
            input->trans_param.change_int[0],
            input->trans_param.change_int[1]);
        _taskIn->taskChange(1, 0.01);
    }

CSFsmResetStimulus(_fsm, "taskSlaveControl = idle", NULL);
    printf("Leaving control_task module ...\n");
```

A104

```
   return (RET_OK);
}
/*
 * control_slave_taskClass::instance \- control_slave_task Instancing Routine
 *
 * This is called when a new instance of a control_slave_task
 * is to be created and installed into the system.
 *
 * If error, return NULL
 */
void *control_slave_taskClass::instance()
{
   /* Your instancing code goes here */ printf("Instancing controlSlaveTask\n");
   printf("   Task input component is %s\n", _taskInputComp);
   if ( !_taskInputComp) {
      fprintf(stderr, "*** Error %s: _taskInputComp name is NULL for %s",
            className(), name());
      return(NULL);
   }

_taskIn = (test_task_inputClass *)
      CSdBaseInquireRecord("test_task_input", _taskInputComp);

if (_taskIn == NULL) {
      fprintf(stderr, "*** Error %s: Cannot find the %s "
            "test_task_input for the %s "
            "transition module!\n",
            className(), _taskInputComp, name());
      return(NULL);
   }

/* Find taskDiff component */
   printf("   taskDiff component is %s\n", _taskDiffComp);
   if ( !_taskDiffComp) {
      fprintf(stderr, "*** Error %s: _taskDiff_comp name is NULL for %s",
            className(), name());
      return(NULL);
   }

_tdIn = (taskDiffClass *)
      CSdBaseInquireRecord("taskDiff", _taskDiffComp);
```

A105

```
    if (_tdIn == NULL) {
        fprintf(stderr, "*** Error %s: Cannot find the %s "
            "contMas master for the %s "
            "transition module!\n",
            className(), _taskDiffComp, name());
        return(NULL);
    } return(this);
}

Package
void control_slave_taskInitialize()
{
    /* Your initialization code for the entire class goes here. */
}

/* End of file */
```

```
                          The COMPMOD software Modules
/*************************************************************************\
* Copyright (C) 1994, California Institute of Technology.
* U.S. Government Sponsorship under NASA Contract NAS7-918 is acknowledged.
*
* Author: Hari Das
*
* $Id: test_joints_input.cc,v 1.2 1995/08/24 22:06:49 hari Exp hari $
*
*                          $ Source: /home/hari/ram/software/cntrlShell/rams/components/keybdin/RCS/test_joints_input.cc,v $
*
\*************************************************************************/

/***
   NAME
     test_joints_input
   PURPOSE

NOTES

HISTORY
     Hari Das - Aug 8, 1995: Created.
***/

/*************************************************************************
 * $Log: test_joints_input.cc,v $
// Revision 1.2  1995/08/24  22:06:49  hari
// Added comments and debugged.
//
// Revision 1.1  1995/08/08  16:17:30  hari
// Initial revision
//
 *
 */ ifdef rcsid
static char rcsid[] = "$Id: test_joints_input.cc,v 1.2 1995/08/24 22:06:49 hari Exp hari $";
#endif /* matches #ifdef rcsid */

/*************************************************************************/
/* test_joints_input \- Component short description
```

A107 banner = ----------

Name: test_joints_input.cc modification history
--------------------
rti,17May95,xxx Skeleton generated

DESCRIPTION:

Skeleton code segment for the test_joints_input component.
Generated automatically by the ControlShell Component Editor.

Do not modify by hand!
This file should be copied to test_joints_input.cc,
and the copy edited to suit your application.

DFE ENTRY FORMAT:

test_joints_input: <InstanceName> <HabitatName>
    deltaJoints         <CSMat_output>

EXAMPLE:

<none>
=================================================
========================== */

```
#include <stdio.h>
include <stdlib.h>
#include <string.h>
include <math.h> include "rtilib/makeheader.h"
include "cs.h"

Public typedef class test_joints_inputClass *test_joints_input;

Public
class test_joints_inputClass : public CSComponentModuleClass { friend class test_joints_inputParseClient;
private:
```

```
/* Additional private members and methods */
float updateBuffer[6];

protected:
    CSMat           _deltaJoints;  /* output */ virtual boolean userInstance();

/* Additional protected members and methods */ public:
    test_joints_inputClass( const char *modulename,
                            const boolean feedthrough,
                            const char *habitatName );
    ~test_joints_inputClass();

/* Component Methods */
    virtual int execute();
    virtual int stateUpdate();

virtual boolean print( int verbosity );
    virtual void *instance();

/* Additional public routines */
    void jointChange(int jointNumber, float increment);

virtual const char *const className() { return ("test_joints_input"); }
};

test_joints_inputClass::test_joints_inputClass(
    const char *modulename,
    const boolean feedthrough,
    const char *habitatName)
    : CSComponentModuleClass(modulename, feedthrough, habitatName)
{
    register int i;

CSdBaseEnterRecord(className(), name(), this);

/* Additional initialization code goes here. */
    /* Set the buffer to zero */
    for (i=0; i<6; i++ )
        updateBuffer[i] = 0.0;
```

A109

```
} test_joints_inputClass::~test_joints_inputClass()
{
    CSdBaseRemoveRecord(className(), name());

/* Your destructor code goes here */
}

/*
 * This is the test_joints_input component's user-instancing routine.
 * You can put custom instancing info here....info that does
 * not necessarily make sense in the Constructor.
 *
 * If error, return FALSE.
 *
 * If you remove this routine, you must also remove it from the class
 * definition above.
 */
boolean test_joints_inputClass::userInstance()
{
#ifdef JUNK
    CreateJointChangeMenus();
#endif /* ifdef JUNK */
    return (TRUE);
}

/*
 * This is the test_joints_input component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int test_joints_inputClass::execute()
{
    return (0);
}
/ ===============================================================
====================
```

A110

```
* Below are the method(s) that you have selected for this component
===========================================================
=====================  */ int test_joints_inputClass::stateUpdate()
{
    register int i;

/* Read the contents of the buffer and reset it to zero */
    for ( i=0; i<6; i++ ) {
        _deltaJoints->pr[i] = updateBuffer[i];
        updateBuffer[i] = 0.0;
    } return (0);

}

Package
void test_joints_inputInitialize()
{
    /* Your initialization code for the entire class goes here. */
}
/
===========================================================
=====================
*                   Menu routines
* Set up menu for keyboard input to control joints.

===========================================================
=====================
*/
/* This routine, called by the manual joint transition, puts the
   increment requested in the  buffer for the respective joint */
void test_joints_inputClass::jointChange(int jointNumber, float
                                increment)
{
    updateBuffer[jointNumber] = increment;
    printf("Incrementing joint %d by %f\n", jointNumber, increment);
}

/* End of file */
```

```
/**********************************************************************\
* Copyright (C) 1994, California Institute of Technology.
* U.S. Government Sponsorship under NASA Contract NAS7-918 is acknowledged.
*
* Author: Hari Das
*
* $Id: test_task_input.cc,v 1.2 1995/08/24 22:06:57 hari Exp hari $
*
*                          $ Source : /home/hari/ram/software/cntrlShell/rams/components/keybdin/RCS/test_task_input.cc,v $
*
\**********************************************************************/

/***
   NAME
     test_task_input
   PURPOSE

NOTES

HISTORY
   Hari Das - Aug 8, 1995: Created.
***/

/**********************************************************************
 * $Log: test_task_input.cc,v $
// Revision 1.2  1995/08/24  22:06:57  hari
// Added comments and debugged.
//
// Revision 1.1  1995/08/08  16:17:41  hari
// Initial revision
//
 *
 */ ifdef rcsid
static char rcsid[] = "$Id: test_task_input.cc,v 1.2 1995/08/24 22:06:57 hari Exp hari $";
#endif /* matches #ifdef rcsid */

/**********************************************************************/
/* test_task_input \- Component short description
     banner = ----------
```

Name: test_task_input.cc modification history
--------------------
rti,15Jun95,xxx Skeleton generated

DESCRIPTION:

Skeleton code segment for the test_task_input component.
Generated automatically by the ControlShell Component Editor.

Do not modify by hand!
This file should be copied to test_task_input.cc,
and the copy edited to suit your application.

DFE ENTRY FORMAT:

```
test_task_input: <InstanceName> <HabitatName>
    tipPos          <CSMat_input>
    tipOri          <CSMat_input>
    desPos          <CSMat_output>
    desOri          <CSMat_output>
```

EXAMPLE:

```
<none>
================================================================
============================ */
```

```cpp
#include <stdio.h>
include <stdlib.h>
#include <string.h>
include <math.h> include "rtilib/makeheader.h"
include "cs.h"

Public typedef class test_task_inputClass *test_task_input;

Public
class test_task_inputClass : public CSComponentModuleClass {
```

```
    friend class test_task_inputParseClient;
private:
    /* Additional private members and methods */
    int taskCoord;
    float increment;
    CSMat deltaOri;         /* A buffer for storing the orientation */
                            /* matrix */
    float deltaPos[3];      /* A buffer for storing the position */
                            /* vector */
    CSMat tempOri;

protected:
    CSMat           _tipPos;    /* input */
    CSMat           _tipOri;    /* input */
    CSMat           _desPos;    /* output */
    CSMat           _desOri;    /* output */ virtual boolean userInstance();

/* Additional protected members and methods */ public:
    test_task_inputClass( const char *modulename,
                          const boolean feedthrough,
                          const char *habitatName );
    ~test_task_inputClass();

/* Component Methods */
    virtual int execute();
    virtual int stateUpdate();

virtual boolean print( int verbosity );
    virtual void *instance();

/* Additional public routines */
    void taskChange(int jointNumber, float increment);
    void taskReset();

virtual const char *const className() { return ("test_task_input"); }
};

test_task_inputClass::test_task_inputClass(
```

```
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} test_task_inputClass::~test_task_inputClass()
{
    CSdBaseRemoveRecord(className(), name());

/* Your destructor code goes here */
    CSMatFree(deltaOri);
    CSMatFree(tempOri);
}

/*
 * This is the test_task_input component's user-instancing routine.
 * You can put custom instancing info here....info that does
 * not necessarily make sense in the Constructor.
 *
 * If error, return FALSE.
 *
 * If you remove this routine, you must also remove it from the class
 *  definition above.
 */
boolean test_task_inputClass::userInstance()
{
    register int i, j;

/* Allocate matrices and initialize */
    deltaOri = CSMatAlloc("deltaOri", 3, 3);
    tempOri  = CSMatAlloc("tempOri", 3, 3);

taskCoord = 0;
    increment = 0.0;
    for (i=0; i<3; i++ ) {
        for ( j=0; j<3; j++ ) {
            deltaOri->rowCache[i][j] = 0.0;
            tempOri->rowCache[i][j] = 0.0;
        }
```

A115

```
        deltaOri->rowCache[i][i] = 1.0;
        tempOri->rowCache[i][i] = 1.0;
        deltaPos[i] = 0.0;
    } return (TRUE);
}

/*
 * This is the test_task_input component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int test_task_inputClass::execute()
{ return (0);
}

/*===================================================================
 =========================
 * Below are the method(s) that you have selected for this component
 ====================================================================
 ==================== */ int test_task_inputClass::stateUpdate()
{ register int i, j;

ifdef VERBOSE
    printf("TESTTASKINPUT\n");
    printf("deltaPos: ");
    for ( i=0; i<3; i++ )
        printf(" %f", deltaPos[i]);
    printf("\n");
#endif /* VERBOSE */

/* read the change in the buffer and reset the buffer */
```

```
    for ( i=0; i<3; i++ ) {
        _desPos->pr[i] += deltaPos[i];
        deltaPos[i] = 0.0;
    }

CSMatMult(tempOri, deltaOri, _desOri);
    CSMatCopy(_desOri, tempOri);
    /* Note: _desOri needss to be an orthonormal matrix - it is
    currently not */
#ifdef VERBOSE
    CSMatPrint(_desOri);
    CSMatPrint(deltaOri);
    CSMatPrint(_desPos);
    CSMatPrint(_tipOri);
endif /* VERBOSE */ for ( i=0; i<3; i++ ) {
        for ( j=0; j<3; j++ )
            deltaOri->rowCache[i][j] = 0.0;
        deltaOri->rowCache[i][i] = 1.0;
    }

}

Package
void test_task_inputInitialize()
{
    /* Your initialization code for the entire class goes here. */
}
/*
==========================================================================
========================
*                       Menu routines
* Set up menu for keyboard input to control task space motion.
*
==========================================================================
==================== */
void test_task_inputClass::taskChange(int taskCoord, float
                                        increment)
{
    register int i;
    register float srx, crx, sry, cry, srz, crz;
    register float rot_coord[3];
```

```
/* Set the commanded input change to the specified coordinate. For
   orientation, it is a little more involved because the orientation
   matrix of the change needs to be computed before the new output can
   be performed */
    printf("Changing task coordinate %d by %f\n",taskCoord, increment);

if ( taskCoord < 3 ) deltaPos[taskCoord] = increment;
    else {
        for ( i=0; i<3; i++ )
            rot_coord[i] = 0.0;
        rot_coord[taskCoord-3] = increment;

srx = sin(rot_coord[0]);
        crx = cos(rot_coord[0]);
        sry = sin(rot_coord[1]);
        cry = cos(rot_coord[1]);
        srz = sin(rot_coord[2]);
        crz = cos(rot_coord[2]);

/* Read the orientation change input, determine the change */
        /* matrix, multiply the change matrix to the current desired */
        /* orientation to get the new desired orientation. */
        deltaOri->rowCache[0][0] = crz*cry;
        deltaOri->rowCache[0][1] = crz*sry*srx - srz*crx;
        deltaOri->rowCache[0][2] = crz*sry*crx + srz*srx;
        deltaOri->rowCache[1][0] = srz*cry;
        deltaOri->rowCache[1][1] = srz*sry*srx + crz*crx;
        deltaOri->rowCache[1][2] = srz*sry*crx - crz*srx;
        deltaOri->rowCache[2][0] = - sry;
        deltaOri->rowCache[2][1] = cry*srx;
    }
} void test_task_inputClass::taskReset()
{
    CSMatCopy(_desPos, _tipPos);
    CSMatCopy(_desOri, _tipOri);
}

/* End of file */
```

```
/******************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_joint.cc,v 1.2 1995/08/24 22:01:49 hari Exp hari $
 *
 * $Source: /home/hari/ram/software/cntrlShell/rams/components/auto/RCS/auto_joint.cc,v
 $
\******************************************************************/

/***
    NAME
      auto_joint
    PURPOSE

NOTES

HISTORY
    Hari Das - Aug 8, 1995: Created.
***/

/******************************************************************
 * $Log: auto_joint.cc,v $
// Revision 1.2  1995/08/24  22:01:49  hari
// Added comments and debugged.
//
// Revision 1.1  1995/08/08  16:03:22  hari
// Initial revision
//
 *
 */ ifdef rcsid
static char rcsid[] = "$Id: auto_joint.cc,v 1.2 1995/08/24 22:01:49 hari Exp hari $";
#endif /* matches #ifdef rcsid */

/******************************************************************/
/* auto_joint \- Component short description
   banner = ----------
```

Name: auto_joint.cc modification history
--------------------
rti,26Jun95,xxx Skeleton generated

DESCRIPTION:

Skeleton code segment for the auto_joint component.
Generated automatically by the ControlShell Component Editor.

Do not modify by hand!
This file should be copied to auto_joint.cc,
and the copy edited to suit your application.

DFE ENTRY FORMAT:

auto_joint: <InstanceName> <HabitatName>
    joints          <CSMat_reference>
    deltaJoints     <CSMat_output>

EXAMPLE:

<none>
==========================================================
============================ */

```
#include <stdio.h>
include <stdlib.h>
#include <string.h>
include <math.h> include "rtilib/makeheader.h"
include "cs.h"
#pragma begin_Public
extern "C" {
#include "../slave/rams_slave.h"
}
pragma end_Public Public typedef class auto_jointClass *auto_joint;

Public
```

```
class auto_jointClass : public CSComponentModuleClass { friend class auto_jointParseClient;
private:
    /* Additional private members and methods */
    CSMat     startPos;       /* The set of joints that are */
                              /* the starting position */
    CSMat     oscOmega;       /* The angular velocity for */
                              /* respective joint oscillation */
    CSMat     jointDes;       /* Joint position */
    CSMat     jointActv;      /* Vector indicating activation */
                              /* of each joint */
    int goFlag;               /* Flag to indicate oscillation */
                              /* on or off */
    float jOsc[6];            /* Limits on joint range of */
                              /* motion */
    float step_deg;           /* Increment on setp size for oscillation */
    int initFlag;

protected:
    CSMat              _joints;  /* reference */
    CSMat              _deltaJoints;  /* output */ virtual boolean userInstance();

/* Additional protected members and methods */ public:
    auto_jointClass( const char *modulename,
                const const boolean feedthrough,
                const char *habitatName );
    ~auto_jointClass();

/* Component Methods */
    virtual int execute();
    virtual int stateUpdate();

virtual boolean print( int verbosity );
    virtual void *instance();

/* Additional public routines */ void auto_joint_change(int coord1, int coord2, int coord3,
                int coord4, int coord5, int coord6,
```

```
                        int onoff);
    void auto_joint_reset();
    virtual const char *const className() { return ("auto_joint"); }
};

auto_jointClass::auto_jointClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} auto_jointClass::~auto_jointClass()
{
    CSdBaseRemoveRecord(className(), name());

/* Your destructor code goes here */
    /* Dealloate memory for matrices */
    CSMatFree(startPos);
    CSMatFree(oscOmega);
    CSMatFree(jointDes);
    CSMatFree(jointActv);

}

/*
 * This is the auto_joint component's user-instancing routine.
 * You can put custom instancing info here....info that does
 * not necessarily make sense in the Constructor.
 *
 * If error, return FALSE.
 *
 * If you remove this routine, you must also remove it from the class
 *  definition above.
 */
boolean auto_jointClass::userInstance()
{

/* Allocate memory for matrices */
```

```
    startPos = CSMatAlloc("startPos", 6, 1);
    oscOmega = CSMatAlloc("oscOmega", 6, 1);
    jointDes = CSMatAlloc("jointDes", 6, 1);
    jointActv = CSMatAlloc("jointACtv", 6, 1);
    goFlag = 0;

/* set limits on travel */
    jOsc[0] = DEG_TO_RAD(10.0);
    jOsc[1] = DEG_TO_RAD(40.0);
    jOsc[2] = DEG_TO_RAD(40.0);
    jOsc[3] = DEG_TO_RAD(40.0);
    jOsc[4] = 0.20;
    jOsc[5] = 0.20;

step_deg = 0.5; /* Was 18.0 for slave, then 3.0 */
    initFlag = 0;

return (TRUE);
}

/*
 * This is the auto_joint component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int auto_jointClass::execute()
{
    return (0);
}

/* ================================================================
   =========================
 * Below are the method(s) that you have selected for this component    *
   ================================================================
   ===================== */ int auto_jointClass::stateUpdate()
{
    register int j;
```

```
/* If first time, set start position to current position */
if ( initFlag == 1 ) {
    CSMatCopy(startPos, _joints);
    initFlag = 0;
}
/* for each joint, compute increment in step size, then new change in joint angle */
for ( j=0; j<6; j++ ) {
    if ( goFlag == 1 ) {
        if ( jointActv->pr[j] != 0 ) {
            /* Increment by (j+1)/step deg */
            oscOmega->pr[j] += DEG_TO_RAD((((double)j)+1.0)/step_deg);
            while (oscOmega->pr[j] >   PI) oscOmega->pr[j] -= 2.0*PI;
            while (oscOmega->pr[j] < - PI) oscOmega->pr[j] += 2.0*PI;

/* Compute a motion that is a sinusiod centered */
            /* between the joint limits */
            jointDes->pr[j] = 0.5 * jOsc[j] * ((float)sin(oscOmega->pr[j]))
                + startPos->pr[j];
        }
    }
    _deltaJoints->pr[j] = jointDes->pr[j] - _joints->pr[j];
}
}

Package
void auto_jointInitialize()
{
    /* Your initialization code for the entire class goes here. */
}

/* Input from the GUI/NDDS system is received and processed in this
   routine. This routine is called from the transition routine that sets
   the command input to the auto_joint mode. */
void auto_jointClass::auto_joint_change(int coord1, int coord2, int coord3,
                int coord4, int coord5, int coord6,
                int onoff)
{
    printf("Changing auto_joint settings %d %d %d %d %d %d %d\n",
            coord1, coord2, coord3, coord4, coord5, coord6, onoff);
    jointActv->pr[0] = (float)coord1; jointActv->pr[1] = (float)coord2;
    jointActv->pr[2] = (float)coord3; jointActv->pr[3] = (float)coord4;
    jointActv->pr[4] = (float)coord5; jointActv->pr[5] = (float)coord6;
```

A124

```
    goFlag = onoff;
}

/* This routine is called from the transition routine that moves the
   state to the auto_joint mode */
void auto_jointClass::auto_joint_reset()
{
   /* Reset initFlag */
   initFlag = 1;
   /* Reset to not move joints */
   goFlag = 0;
   CSMatCopy(startPos, _joints);
#ifdef OLD
   register int j;

for ( j=0; j<6; j++ ) {
      oscOmega->pr[j] = asin((double)
             2.0*(startPos->pr[j]- 0.5 * (jMaxOsc[j] + jMinOsc[j]))
                      /(jMaxOsc[j] - jMinOsc[j]));
   }
#endif /* ifdef OLD */
}

/* End of file */
```

```
/**************************************************************\
 * Copyright (C) 1994, California Institute of Technology.
 * U.S. Government Sponsorship under NASA Contract NAS7-918 is acknowledged.
 *
 * Author: Hari Das
 *
 * $Id: auto_task.cc,v 1.2 1995/08/24 22:02:13 hari Exp hari $
 *
 * $Source: /home/hari/ram/software/cntrlShell/rams/components/auto/RCS/auto_task.cc,v
 $
\**************************************************************/

/***
   NAME
     auto_task
   PURPOSE

NOTES

HISTORY
   Hari Das - Aug 8, 1995: Created.
***/

/**************************************************************
 * $Log: auto_task.cc,v $
// Revision 1.2  1995/08/24  22:02:13  hari
// Added comments and debugged.
//
// Revision 1.1  1995/08/08  16:03:38  hari
// Initial revision
//
 *
 */ ifdef rcsid
static char rcsid[] = "$Id: auto_task.cc,v 1.2 1995/08/24 22:02:13 hari Exp hari $";
#endif /* matches #ifdef rcsid */

/**************************************************************/
/* auto_task \- Component short description
   banner = ----------
```

Name: auto_task.cc modification history
--------------------
rti,27Jun95,xxx Skeleton generated

DESCRIPTION:

Skeleton code segment for the auto_task component.
Generated automatically by the ControlShell Component Editor.

Do not modify by hand!
This file should be copied to auto_task.cc,
and the copy edited to suit your application.

DFE ENTRY FORMAT:

```
auto_task: <InstanceName> <HabitatName>
    tipPos          <CSMat_reference>
    tipOri          <CSMat_reference>
    desPos          <CSMat_output>
    desOri          <CSMat_output>
```

EXAMPLE:

```
<none>
================================================
========================= */ include <stdio.h>
include <stdlib.h>
#include <string.h>
include <math.h> include "rtilib/makeheader.h"
include "cs.h"
#pragma begin_Public
extern "C" {
#include "../slave/rams_slave.h"
}
pragma end_Public
```

A127

Public typedef class auto_taskClass *auto_task;

Public
class auto_taskClass : public CSComponentModuleClass { friend class auto_taskParseClient;
  private:
    /* Additional private members and methods */
    CSMat    startPos;       /* The set of joints that are */
                                 /* the starting position */
    CSMat    startOri;
    CSMat    tempPos;        /* The set of pos that are */
                                   /* a temp position */
    CSMat    changeOri;
    CSMat    oscOmega;        /* The angular velocity for */
                                   /* respective joint oscillation */
    CSMat    taskActv;        /* Vector indicating activation */
                                   /* of each joint */
    int goFlag;              /* Flag to indicate oscillation */
                                   /* on or off */
    int altFlag[6];          /* Flag to indicate oscillation */
                                   /* order (sine or cosine) */
    float tMaxOsc[6];       /* Limits on range of */
                                   /* motion */
    float tMinOsc[6];

protected:
    CSMat           _tipPos;  /* reference */
    CSMat           _tipOri;  /* reference */
    CSMat           _desPos;  /* output */
    CSMat           _desOri;  /* output */ virtual boolean userInstance();

/* Additional protected members and methods */ public:
    auto_taskClass( const char *modulename,
                  const boolean feedthrough,
                  const char *habitatName );
    ~auto_taskClass();

/* Component Methods */
    virtual int execute();

A128

```
    virtual int stateUpdate();

virtual boolean print( int verbosity );
    virtual void *instance();

/* Additional public routines */ void auto_task_change(int coord1, int coord2, int coord3,
                    int coord4, int coord5, int coord6,
                    int onoff);
    void auto_task_reset();
    virtual const char *const className() { return ("auto_task"); }
};

auto_taskClass::auto_taskClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} auto_taskClass::~auto_taskClass()
{
    CSdBaseRemoveRecord(className(), name());

/* Your destructor code goes here */
    /* Deallocate memory for matrices */
    CSMatFree(startPos);
    CSMatFree(startOri);
    CSMatFree(tempPos);
    CSMatFree(changeOri);
    CSMatFree(oscOmega);
    CSMatFree(taskActv);
}

/*
 * This is the auto_task component's user-instancing routine.
 * You can put custom instancing info here....info that does
 * not necessarily make sense in the Constructor.
```

A129

```
 *
 * If error, return FALSE.
 *
 * If you remove this routine, you must also remove it from the class
 * definition above.
 */
boolean auto_taskClass::userInstance()
{
    /* Allocate memory for matrices */
    startPos  = CSMatAlloc("startPos", 3, 1);
    tempPos   = CSMatAlloc("tempPos", 6, 1);
    oscOmega  = CSMatAlloc("oscOmega", 6, 1);
    taskActv  = CSMatAlloc("taskActv", 6, 1);
    startOri  = CSMatAlloc("startOri", 3, 3);
    changeOri = CSMatAlloc("changeOri", 3, 3);

/* Set initial states for motion control parameters */
    goFlag = 0;
    altFlag[0] = 0;
    altFlag[1] = 0;
    altFlag[2] = 0;
    altFlag[3] = 0;
    altFlag[4] = 0;
    altFlag[5] = 0;

tMaxOsc[0] = 0.02;
    tMaxOsc[1] = 0.02;
    tMaxOsc[2] = 0.02;
    tMaxOsc[3] = DEG_TO_RAD(10.0);
    tMaxOsc[4] = DEG_TO_RAD(10.0);
    tMaxOsc[5] = DEG_TO_RAD(10.0);

tMinOsc[0] = -0.03;
    tMinOsc[1] = -0.02;
    tMinOsc[2] = -0.01;
    tMinOsc[3] = DEG_TO_RAD(-10.0);
    tMinOsc[4] = DEG_TO_RAD(-10.0);
    tMinOsc[5] = DEG_TO_RAD(-10.0);

return (TRUE);
}

/*
```

```
* This is the auto_task component's main routine.
* It is called each "loop". More precisely, it is normally installed
* into an execution list (e.g. the "Sample" list), and executed each
* time the list runs (e.g. at each sample clock).
*
* If there is an error, the function should return -1
*/
int auto_taskClass::execute()
{ return (0);
}

/*
============================================================
=======================
* Below are the method(s) that you have selected for this component ============================================================
==================== */ int auto_taskClass::stateUpdate()
{
    register int j;
    float cr, sr, cy, sy, cp, sp;

#ifdef VERBOSE
    printf("go: %d actv: %f %f %f %f %f %f\n",
           goFlag, taskActv->pr[0], taskActv->pr[1], taskActv->pr[2],
           taskActv->pr[3], taskActv->pr[4], taskActv->pr[5]);
#endif /* ifdef VERBOSE */
    /* For each task space coord. if motion flags indicate motion,
    compute new setp size, then compute new coordinate position. Note
    that successive coordinates oscillate at phase shifts to allow
    circular tip paths. */
    for ( j=0; j<6; j++ ) {
        if (( goFlag == 1 )&&( taskActv->pr[j] != 0.0 )) {
            /* Increment the angular position for the respective */
            /* coordinates */
            oscOmega->pr[j] += DEG_TO_RAD(1.0);
            if (oscOmega->pr[j] >  PI) oscOmega->pr[j] -= 2.0*PI;
#ifdef VERBOSE
            printf("Omega: %f %f %f %f %f %f\n",
                   oscOmega->pr[0], oscOmega->pr[1], oscOmega->pr[2],
```

A131

```
                oscOmega->pr[3], oscOmega->pr[4], oscOmega->pr[5]);
#endif /* ifdef VERBOSE */
        /* Compute a motion that is a sinusiod centered */
        /* between the task limits */
        /* Note that the reason for using cos then sine is
           so that when 2 successive joints are selected for
           the sinusoidal motion, the resulting motion will be
           "circular". */
        if (altFlag[j]==0) {
            tempPos->pr[j] = 0.5 * (tMaxOsc[j] - tMinOsc[j])
                *((float)sin(oscOmega->pr[j]));
        }
        else {
            tempPos->pr[j] = 0.5 * (tMaxOsc[j] - tMinOsc[j])
                *((float)cos(oscOmega->pr[j]));
        }
    }
}

/* Save the new position and change in orientation */ for ( j=0; j<3; j++ ) {
    _desPos->pr[j] = tempPos->pr[j] + startPos->pr[j];
}
#ifdef VERBOSE
    printf("tempPos: %f %f %f\n", tempPos->pr[0], tempPos->pr[1], tempPos->pr[2]);
    printf("_desPos: %f %f %f\n", _desPos->pr[0], _desPos->pr[1], _desPos->pr[2]);
    printf("startPos: %f %f %f\n", startPos->pr[0], startPos->pr[1], startPos->pr[2]);
#endif /* ifdef VERBOSE */
    cr = ((float)cos(tempPos->pr[5])); sr = ((float)sin(tempPos->pr[5]));
    cy = ((float)cos(tempPos->pr[4])); sy = ((float)sin(tempPos->pr[4]));
    cp = ((float)cos(tempPos->pr[3])); sp = ((float)sin(tempPos->pr[3]));

changeOri->rowCache[0][0] = cr*cy;
    changeOri->rowCache[0][1] = cr*sy*sp - sr*cp;
    changeOri->rowCache[0][2] = cr*sy*cp + sr*sp;
    changeOri->rowCache[1][0] = sr*cy;
    changeOri->rowCache[1][1] = sr*sy*sp + cr*cp;
    changeOri->rowCache[1][2] = sr*sy*cp - cr*sp;
    changeOri->rowCache[2][0] = -sy;
    changeOri->rowCache[2][1] = cy*sp;
    changeOri->rowCache[2][2] = cy*cp;

/* Update the new desired orientation */
```

A132

```
        CSMatMult(_desOri, changeOri, startOri);
}

Package
void auto_taskInitialize()
{
    /* Your initialization code for the entire class goes here. */
}

/* This routine is called from the transition routine that sets the new
    command to the real-time system specifying the change in oscillation
    parameters */
void auto_taskClass::auto_task_change(int coord1, int coord2, int coord3,
                    int coord4, int coord5, int coord6,
                    int onoff)
{
   register int i, j;

printf("Changing auto_task settings %d %d %d %d %d %d %d\n",
         coord1, coord2, coord3, coord4, coord5, coord6, onoff);
   taskActv->pr[0] = (float)coord1; taskActv->pr[1] = (float)coord2;
   taskActv->pr[2] = (float)coord3; taskActv->pr[3] = (float)coord4;
   taskActv->pr[4] = (float)coord5; taskActv->pr[5] = (float)coord6;

CSMatCopy(startPos, _tipPos);
   CSMatCopy(startOri, _tipOri);
   CSMatCopy(_desPos, _tipPos);
   CSMatCopy(_desOri, _tipOri);
   CSMatZero(tempPos);

for ( i=0, j=0; i<6; i++ ) {
      if (taskActv->pr[i] != 0.0 ) {
         j++;
         altFlag[i] = ((int)fmod((double)j, 1.0));
      }
   } goFlag = onoff;
}

/* This routine is called from the transition routine that switches from
    the idle state to the auto_task state. It resets the motion
    parameters */
```

A133

```
void auto_taskClass::auto_task_reset()
{
   register int j;

CSMatCopy(startPos, _tipPos);
   CSMatCopy(startOri, _tipOri);
   CSMatCopy(_desPos, _tipPos);
   CSMatCopy(_desOri, _tipOri);
   CSMatZero(tempPos);

for ( j=0; j<6; j++ ) {
      oscOmega->pr[j] = 0.0;
      altFlag[j] = 0;
      taskActv->pr[j] = 0.0;
   }
   goFlag = 0;
}
```

/* End of file */

```
/*******************************************************************
 *      Copyright (c) 1993 Jet Propulsion Laboratory
 *      U.S. Government Sponsorship under NASA Contract NAS7-1270 is acknowledge
 *
 *      Author: Hari Das
 *
 *      $Id: rams_slave_fk.cc,v 1.2 1995/08/24 22:09:26 hari Exp hari $
 *      $Source : /home/hari/ram/software/cntrlShell/rams/components/slave/RCS/rams_slave_fk.cc,v $
 *      $Revision: 1.2 $
 *      $Date: 1995/08/24 22:09:26 $
 *      $Author: hari $
 *******************************************************************
 * $Log: rams_slave_fk.cc,v $
// Revision 1.2  1995/08/24  22:09:26  hari
// Added comments and debugged.
//
// Revision 1.1  1995/04/25  14:52:00  hari
// Initial revision
//
 *
 */ static char rcsid[] = "$Id: rams_slave_fk.cc,v 1.2 1995/08/24 22:09:26 hari Exp hari $";

/***
   NAME
      rams_slave_fk.cc
   PURPOSE
      RAMS Slave forward kinematics.
   NOTES HISTORY
      Hari Das - Apr 24, 1995: Created.
***/
/* rams_slave_fk \- Component short description
   banner = ----------

Name: rams_slave_fk.cc modification history
--------------------
rti,17May95,xxx Skeleton generated
```

DESCRIPTION:

Skeleton code segment for the rams_slave_fk component.
Generated automatically by the ControlShell Component Editor.

Do not modify by hand!
This file should be copied to rams_slave_fk.cc,
and the copy edited to suit your application.

DFE ENTRY FORMAT:

```
rams_slave_fk:  <InstanceName> <HabitatName>
    joints              <CSMat_reference>
    linkLengths         <CSMat_reference>
    jointSines          <CSMat_output>
    jointCosines        <CSMat_output>
    tipOri              <CSMat_output>
    tipPos              <CSMat_output>
    wrist2UnivJnt       <CSMat_output>
    gearBailAngles      <CSMat_output>
```

EXAMPLE:

<none>
================================================================
=========================== */

```cpp
#include <stdio.h>
include <stdlib.h>
#include <string.h>
include <math.h>
#include "CSMat.h"
#include "rtilib/makeheader.h"
include "cs.h"
#include "rams_slave.h"

Public typedef class rams_slave_fkClass *rams_slave_fk;

Public
class rams_slave_fkClass : public CSComponentModuleClass { friend class rams_slave_fkParseClient;
  private:
```

```
/* Additional private members and methods */
CSMat unit3matrix;        /* The identity 3x3 matrix */
CSMat zero13matrix;       /* A zero 1x3 matrix */
CSMat temp331matrix;      /* A temp storage 3x3 matrix */
CSMat temp332matrix;      /* A temp storage 3x3 matrix */
CSMat temp13matrix;       /* A temp storage 1x3 matrix */
CSMat joints_exp;         /* Joints in kinematic model of slave */
                          /* robot */
CSMat S;                  /* Accumulation of the attitude matrix */
CSMat S1;                 /* Accumulation of the attitude matrix */
CSMat r;                  /* Accumulation of the position vector */
CSMat A[10];              /* Transformation matrices for each joint */
CSMat linkVectors[10];    /* Link vectors */ virtual int update_slave_FK_matrices();
virtual int set_slave_joint_angles();
virtual float slave_slider_to_gear_bail_angle(float extn);

protected:
    CSMat        _joints;        /* reference */
    CSMat        _linkLengths;   /* reference */
    CSMat        _jointSines;    /* output */
    CSMat        _jointCosines;  /* output */
    CSMat        _tipOri;        /* output */
    CSMat        _tipPos;        /* output */
    CSMat        _wrist2UnivJnt; /* output */
    CSMat        _gearBailAngles; /* output */ virtual boolean userInstance();

/* Additional protected members and methods */ public:
    rams_slave_fkClass( const char *modulename,
                        const boolean feedthrough,
                        const char *habitatName );
    ~rams_slave_fkClass();

/* Component Methods */
virtual int execute();

virtual boolean print( int verbosity );
virtual void *instance();
```

```
    /* Additional public routines */ virtual const char *const className() { return ("rams_slave_fk"); }
};

rams_slave_fkClass::rams_slave_fkClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} rams_slave_fkClass::~rams_slave_fkClass()
{
    register int i;

CSdBaseRemoveRecord(className(), name());

/* Your destructor code goes here */
    /* Deallocate the memory allocated and initialize the variables */
    CSMatFree(unit3matrix);
    CSMatFree(zero13matrix);
    CSMatFree(temp331matrix);
    CSMatFree(temp332matrix);
    CSMatFree(temp13matrix);
    CSMatFree(joints_exp);
    CSMatFree(S);
    CSMatFree(S1);
    CSMatFree(r);
    for ( i=0; i<10; i++ ) {
        CSMatFree(linkVectors[i]);
    }
    for ( i=0; i<10; i++ ) {
        CSMatFree(A[i]);
    }
}

/*
 * This is the rams_slave_fk component's user-instancing routine.
```

A138

```
 * You can put custom instancing info here....info that does
 * not necessarily make sense in the Constructor.
 *
 * If error, return FALSE.
 *
 * If you remove this routine, you must also remove it from the class
 * definition above.
 */
boolean rams_slave_fkClass::userInstance()
{
    register char Aname[5], lname[5];
    register int i, j, k;

/* Allocate and initialize the matrices */
    unit3matrix = CSMatAlloc("unit3matrix", 3, 3);
    zero13matrix = CSMatAlloc("zero13matrix", 3, 1);
    temp331matrix = CSMatAlloc("temp331matrix", 3, 3);
    temp332matrix = CSMatAlloc("temp332matrix", 3, 3);
    temp13matrix = CSMatAlloc("temp13matrix", 3, 1);
    joints_exp = CSMatAlloc("joints_exp", 10, 1);
    S = CSMatAlloc("S", 3, 3);
    S1 = CSMatAlloc("S1", 3, 3);
    r = CSMatAlloc("r", 3, 1);
/*  A = new CSMat[10]; */
    linkVectors = new CSMat[10]; */
    for ( i=0; i<3; i++ ) {
        for (j=0; j<3; j++ )
            unit3matrix->rowCache[i][j] = 0.0;
        unit3matrix->rowCache[i][i] = 1.0;
        zero13matrix->pr[i] = 0.0;
    } for ( i=0; i<10; i++ ) {
        sprintf(lname, "l[%d]", i);
        linkVectors[i] = CSMatAlloc(lname, 3, 1);
        for ( j=0; j<2; j++ ) {
            linkVectors[i]->pr[j] = 0.0;
        }
        linkVectors[i]->pr[2] = _linkLengths->pr[i];
        sprintf(Aname, "A[%d]", i);
        A[i] = CSMatAlloc(Aname, 3, 3);
        for ( j=0; j<3; j++ ) {
            for ( k=0; k<3; k++ ) {
                A[i]->rowCache[j][k] = 0.0;
```

A139

```
            }
        A[i]->rowCache[j][j] = 1.0;
        }
    } return (TRUE);
}
/*
 * This is the rams_slave_fk component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int rams_slave_fkClass::execute()
{
    register int i;

/* copy yhe slave joint angles into the kinematics model parameters */
    set_slave_joint_angles();

/* Update the forward transformation matrices */
    update_slave_FK_matrices();

/* Recursive computation of jacobian, and forward kinematics */
    CSMatCopy(S, unit3matrix);
    CSMatCopy(r, zero13matrix);
    for ( i=0; i<10; i++) {
        CSMatMult(S1, A[i], S);
        CSMatCopy(S, S1);
        CSMatAdd(temp13matrix, r, linkVectors[i]);
        CSMatMult(r, A[i], temp13matrix);
    }
    CSMatCopy(_tipOri, S);
    CSMatCopy(_tipPos, r);

/* Compute the wrist base to universal joint 1 output attitude */
    /* matrix. Note that this is used in compute_slave_joint_vel() */

CSMatMult(temp331matrix, A[3], A[4]);
    CSMatMult(temp332matrix, A[2], temp331matrix);
```

A140

```
    CSMatTranspose(_wrist2UnivJnt, temp332matrix);

#ifdef VERBOSE
    printf("FwdKin output\n");
    CSMatPrint(_tipPos);
    CSMatPrint(_tipOri);
endif /* ifdef VERBOSE */ return (0);
}

/*================================================================
========================
 * Below are the method(s) that you have selected for this component
================================================================
==================== */

Package
void rams_slave_fkInitialize()
{
    /* Your initialization code for the entire class goes here. */
}

/***
    NAME
      updateSlaveFKMatrices
    PURPOSE
      Update the forward kinematics transformation matrices of the RAMS slave robot.
      Joint values in the joints[] array should have been updated.
    NOTES

*/
int rams_slave_fkClass::update_slave_FK_matrices()
{
    register int i;

for ( i=0; i<10; i++ ) {
      _jointSines->pr[i]   = sin(joints_exp->pr[i]);
      _jointCosines->pr[i] = cos(joints_exp->pr[i]);
    }
```

A141

```
/* Set transpose of A instead of A */
A[0]->rowCache[1][1] =   _jointCosines->pr[0]; /* wrist pitch */
A[0]->rowCache[2][1] =   _jointSines->pr[0]; /* tip -2nd universal joint */
A[0]->rowCache[1][2] = - _jointSines->pr[0];
A[0]->rowCache[2][2] =   _jointCosines->pr[0];

A[1]->rowCache[0][0] =   _jointCosines->pr[1]; /* wrist yaw */
A[1]->rowCache[2][0] = - _jointSines->pr[1]; /* tip - 2nd universal joint */
A[1]->rowCache[0][2] =   _jointSines->pr[1];
A[1]->rowCache[2][2] =   _jointCosines->pr[1];

A[2]->rowCache[0][0] =   _jointCosines->pr[2]; /* wrist yaw - internmediate - 1st */
A[2]->rowCache[2][0] = - _jointSines->pr[2]; /* universal joint */
A[2]->rowCache[0][2] =   _jointSines->pr[2];
A[2]->rowCache[2][2] =   _jointCosines->pr[2];

A[3]->rowCache[1][1] =   _jointCosines->pr[3]; /* wrist pitch - intermediate - */
A[3]->rowCache[2][1] =   _jointSines->pr[3]; /*    1st universal joint */
A[3]->rowCache[1][2] = - _jointSines->pr[3];
A[3]->rowCache[2][2] =   _jointCosines->pr[3];

A[4]->rowCache[0][0] =   _jointCosines->pr[4]; /* wrist roll */
                         /* - tip - start of wrist */
A[4]->rowCache[1][0] =   _jointSines->pr[4];
A[4]->rowCache[0][1] = - _jointSines->pr[4];
A[4]->rowCache[1][1] =   _jointCosines->pr[4];

A[5]->rowCache[1][1] =   _jointCosines->pr[5]; /* pitch  - elbow 2 */
A[5]->rowCache[2][1] =   _jointSines->pr[5];
A[5]->rowCache[1][2] = - _jointSines->pr[5];
A[5]->rowCache[2][2] =   _jointCosines->pr[5];

A[6]->rowCache[1][1] =   _jointCosines->pr[6]; /* pitch  - elbow 1 */
A[6]->rowCache[2][1] =   _jointSines->pr[6];
A[6]->rowCache[1][2] = - _jointSines->pr[6];
A[6]->rowCache[2][2] =   _jointCosines->pr[6];

A[7]->rowCache[1][1] =   _jointCosines->pr[7]; /* pitch  - shoulder 2 */
A[7]->rowCache[2][1] =   _jointSines->pr[7];
A[7]->rowCache[1][2] = - _jointSines->pr[7];
A[7]->rowCache[2][2] =   _jointCosines->pr[7];

A[8]->rowCache[1][1] =   _jointCosines->pr[8]; /* pitch - shoulder 1 */
A[8]->rowCache[2][1] =   _jointSines->pr[8];
```

A142

```
A[8]->rowCache[1][2] = - _jointSines->pr[8];
A[8]->rowCache[2][2] =   _jointCosines->pr[8];

A[9]->rowCache[0][0] =   _jointCosines->pr[9]; /* roll - torso*/
A[9]->rowCache[1][0] =   _jointSines->pr[9];
A[9]->rowCache[0][1] = - _jointSines->pr[9];
A[9]->rowCache[1][1] =   _jointCosines->pr[9];

return(0);
}

/***
    NAME
    setJointAngles
    PURPOSE
    Given the cable pulley angles, compute the robot joint angles
    NOTES

*/
int rams_slave_fkClass::set_slave_joint_angles()
{
    float M, a, b, c, cg3, sg3, cg4, sg4, cg5,
        sg5, c4, s4;

/* Set the joint values for the upper arm and wrist roll */
    joints_exp->pr[9] = _joints->pr[0];      /* torso */
    joints_exp->pr[8] = _joints->pr[1]/2.0;  /* shoulder 1 */
    joints_exp->pr[7] = _joints->pr[1]/2.0;  /* shoulder 2 */
    joints_exp->pr[6] = _joints->pr[2]/2.0;  /* elbow 1 */
    joints_exp->pr[5] = _joints->pr[2]/2.0;  /* elbow 2 */
    joints_exp->pr[4] = _joints->pr[3];      /* wrist roll */

/* For the gear bails, there is a slider to rotary motion conversion */
    /* that precedes the gear bail to universal joint computation */
    _gearBailAngles->pr[0] = slave_slider_to_gear_bail_angle(_joints->pr[4]);
    _gearBailAngles->pr[1] = slave_slider_to_gear_bail_angle(_joints->pr[5]);

/* Compute sines and cosines of gear bail angles */
    sg3 = sin(_joints->pr[3]);
    cg3 = cos(_joints->pr[3]);
    sg4 = sin(_gearBailAngles->pr[0]);
    cg4 = cos(_gearBailAngles->pr[0]);
    sg5 = sin(_gearBailAngles->pr[1]);
    cg5 = cos(_gearBailAngles->pr[1]);
```

```
/* Do gear bail angle to universal joint kinematics first */
/* these were derived from eqns 28a,b,c,d in Williams' paper */
M = sqrt(cg4*cg4 + sg4*sg4*cg5*cg5);
a = cg4*sg5/M;
b = -sg4*cg5/M;
c = cg4*cg5/M;

/* This is the wrist pitch joint */
joints_exp->pr[3] = joints_exp->pr[0] = atan2(a*sg3-b*cg3, c*(sg3*sg3+cg3*cg3));
s4 = sin(joints_exp->pr[0]);
c4 = cos(joints_exp->pr[0]);

/* This is the wrist yaw joint */
joints_exp->pr[2] = joints_exp->pr[1] = atan2(a/cg3-sg3*s4*c/(cg3*c4), c/cg4);

/* below for testing */

}

/***
  NAME
    slaveSliderToGearBailAngle
  PURPOSE
    Compute the gear bail angle given the slider position.
  NOTES

*/
float rams_slave_fkClass::slave_slider_to_gear_bail_angle(float extn)
{
    float Ls2, Rg2, Ds2, Fs, Gs, As, as, bs, cs;
    float b24ac, x, y2, bailAngle;

Ls2 = SLAVELs*SLAVELs;
    Rg2 = SLAVERg*SLAVERg;
    Ds2 = SLAVEDs*SLAVEDs;
    Fs = sqrt(Ls2 - (SLAVERg-SLAVEDs)*(SLAVERg-SLAVEDs));
    Gs = extn - Fs;
    As = Gs*Gs + Rg2 + SLAVEDs*SLAVEDs - Ls2;
    as = 1.0 + (Gs*Gs/Ds2);
    bs = As*Gs/Ds2;
    cs = As*As/(4.0*Ds2) - Rg2;

b24ac = bs*bs - 4.0*as*cs;
```

```
    if ( b24ac < 0.0 ) {
        printf("Slider to gear bail: no solution\n");
        return(0.0);
    }
    x = (bs + sqrt(b24ac))/(2.0*as);
    y2 = Rg2 - x*x;
    if ( y2 < 0.0 ) {
        printf("Slider to gear bail: no solution\n");
        return(0.0);
    }
    bailAngle = atan2(x, sqrt(y2));
    return(bailAngle);
}
/* End of file */
```

```
/**********************************************************************
 *    Copyright (c) 1993 Jet Propulsion Laboratory
 *    U.S. Government Sponsorship under NASA Contract NAS7-1270 is acknowledge
 *
 *    Author: Hari Das
 *
 *    $Id: rams_slave_ik.cc,v 1.2 1995/08/24 22:09:34 hari Exp hari $
 *    $Source: /home/hari/ram/software/cntrlShell/rams/components/slave/RCS/rams_slave_ik.cc,v $
 *    $Revision: 1.2 $
 *    $Date: 1995/08/24 22:09:34 $
 *    $Author: hari $
 **********************************************************************
 * $Log: rams_slave_ik.cc,v $
// Revision 1.2  1995/08/24  22:09:34  hari
// Added comments and debugged.
//
// Revision 1.1  1995/04/25  19:54:42  hari
// Initial revision
//
 *
 */ static char rcsid[] = "$Id: rams_slave_ik.cc,v 1.2 1995/08/24 22:09:34 hari Exp hari $";

/***
   NAME
     rams_slave_ik
   PURPOSE
     RAMS slave robot inverse kinematics.
   NOTES HISTORY
     Hari Das - Apr 25, 1995: Created.
***/
/* rams_slave_ik \- Component short description
   banner = ----------

Name: rams_slave_ik.cc modification history
--------------------
rti,25Apr95,xxx Skeleton generated
```

DESCRIPTION:

Skeleton code segment for the rams_slave_ik component.
Generated automatically by the ControlShell Component Editor.

Do not modify by hand!
This file should be copied to rams_slave_ik.cc,
and the copy edited to suit your application.

DFE ENTRY FORMAT:

```
rams_slave_ik: <InstanceName> <HabitatName>
    jointSines       <CSMat_input>
    jointCosines     <CSMat_input>
    deltaPos         <CSMat_input>
    deltaOri         <CSMat_input>
    linkLengths      <CSMat_reference>
    deltaJoints      <CSMat_output>
    tipOri           <CSMat_input>
    wrist2UnivJnt    <CSMat_input>
    gearBailAngles   <CSMat_input>
```

EXAMPLE:

<none>
=========================================================================== */

```
#include <stdio.h>
include <stdlib.h>
#include <string.h>
include <math.h>
#include "CSMat.h"
#include "rtilib/makeheader.h"
include "cs.h"
#include "rams_slave.h"

Public typedef class rams_slave_ikClass *rams_slave_ik;

Public
class rams_slave_ikClass : public CSComponentModuleClass { friend class rams_slave_ikParseClient;
```

A147

```
private:
    /* Additional private members and methods */
    CSMat phiOT[10];        /* The PHI matrices - See
                               Kinematics notes */
    CSMat temp661matrix;    /* A temp 6x6 matrix */
    CSMat temp662matrix;    /* A temp 6x6 matrix */
    CSMat temp663matrix;    /* A temp 6x6 matrix */
    CSMat temp161matrix;    /* A temp 6x1 vector */
    CSMat zero16matrix;     /* A zero element 6x1 matrix */
    CSMat tipErrVec;        /* A vector of tip errors */
    CSMat zVec;             /* A temp 6x1 matrix */
    CSMat VVec;             /* A temp 6x1 matrix */
    CSMat HO[10];           /* Vectors that indicate the joint
                               rotation axes */ virtual int matrix_to_roll_pitch_yaw(CSMat dirMat, CSMat oriVec);
    virtual int update_slave_IK_matrices();
    virtual void mult_SA_661_matrix( CSMat a, CSMat b, CSMat c );
    virtual void create_TR_matrix(CSMat rot, float l, CSMat tr);
    virtual float slave_gear_bail_angle_velocity_to_slider_velocity(
        float gVel, float gearAngle);

protected:
    CSMat           _jointSines;    /* input */
    CSMat           _jointCosines;  /* input */
    CSMat           _deltaPos;      /* input */
    CSMat           _deltaOri;      /* input */
    CSMat           _linkLengths;   /* reference */
    CSMat           _deltaJoints;   /* output */
    CSMat           _tipOri;        /* input */
    CSMat           _wrist2UnivJnt; /* input */
    CSMat           _gearBailAngles; /* input */ virtual boolean userInstance();

/* Additional protected members and methods */ public:
    rams_slave_ikClass( const char *modulename,
                        const boolean feedthrough,
                        const char *habitatName );
    ~rams_slave_ikClass();

/* Component Methods */
```

```
    virtual int execute();

virtual boolean print( int verbosity );
    virtual void *instance();

/* Additional public routines */ virtual const char *const className() { return ("rams_slave_ik"); }
};

rams_slave_ikClass::rams_slave_ikClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} rams_slave_ikClass::~rams_slave_ikClass()
{
    register int i;

CSdBaseRemoveRecord(className(), name());

/* Your destructor code goes here */
    /* Deallocate the matrices */
    CSMatFree(temp661matrix);
    CSMatFree(temp662matrix);
    CSMatFree(temp663matrix);
    CSMatFree(temp161matrix);
    CSMatFree(zero16matrix);
    CSMatFree(tipErrVec);
    CSMatFree(zVec);
    CSMatFree(VVec);
    for ( i=0; i<10; i++ ) {
        CSMatFree(HO[i]);
    }
    for ( i=0; i<10; i++ ) {
        CSMatFree(phiOT[i]);
    }
```

A149

```
    /*
    delete []HO;
    delete []phiOT;
    */
}

/*
 * This is the rams_slave_ik component's user-instancing routine.
 * You can put custom instancing info here....info that does
 * not necessarily make sense in the Constructor.
 *
 * If error, return FALSE.
 *
 * If you remove this routine, you must also remove it from the class
 * definition above.
 */
boolean rams_slave_ikClass::userInstance()
{ register char phiTname[10], Hname[6];
    register int i, j, k;

/* Allocate the matrices and initialize them */
    temp661matrix = CSMatAlloc("temp661matrix", 6, 6);
    for ( i=0; i<6; i++ )
        for ( j=0; j<6; j++ )
            temp661matrix->rowCache[i][j] = 0.0;
    temp662matrix = CSMatAlloc("temp662matrix", 6, 6);
    temp663matrix = CSMatAlloc("temp663matrix", 6, 6);
    temp161matrix = CSMatAlloc("temp161matrix", 6, 1);
    zero16matrix = CSMatAlloc("zero16matrix", 6, 1);
    for ( i=0; i<6; i++ )
        zero16matrix->pr[i] = 0.0;
    tipErrVec = CSMatAlloc("tipErrVec", 6, 1);
    zVec = CSMatAlloc("zVec", 6, 1);
    VVec = CSMatAlloc("VVec", 6, 1);
    for ( i=0; i<10; i++ ) {
        sprintf(Hname, "HO[%d]", i);
        HO[i] = CSMatAlloc(Hname, 6, 1);
        for ( j=0; j<6; j++ ) {
            HO[i]->pr[j] = 0.0;
        }
        sprintf(phiTname, "A[%d]", i);
        phiOT[i] = CSMatAlloc(phiTname, 6, 6);
```

A150

```
        for ( j=0; j<6; j++ ) {
            for ( k=0; k<6; k++ ) {
                phiOT[i]->rowCache[j][k] = 0.0;
            }
        }
    }

HO[0]->pr[0] = 1.0;
HO[1]->pr[1] = 1.0;
HO[2]->pr[1] = 1.0;
HO[3]->pr[0] = 1.0;
HO[4]->pr[2] = 1.0;
HO[5]->pr[0] = 1.0;
HO[6]->pr[0] = 1.0;
HO[7]->pr[0] = 1.0;
HO[8]->pr[0] = 1.0;
HO[9]->pr[2] = 1.0;

/* Set up phi matrices */
    /* phi(1, 0) - Transformation from 2nd universal joint to tip */
phiOT[0]->rowCache[0][0] = 1.0;
phiOT[0]->rowCache[1][1] = 1.0;
phiOT[0]->rowCache[2][2] = 1.0;
phiOT[0]->rowCache[3][3] = 1.0;
phiOT[0]->rowCache[4][4] = 1.0;
phiOT[0]->rowCache[5][5] = 1.0;
phiOT[0]->rowCache[4][0] = -_linkLengths->pr[0];
phiOT[0]->rowCache[3][1] = _linkLengths->pr[0];

/* phi(2, 1) - pitch 2nd universal joint */
phiOT[1]->rowCache[0][0] =   1.0;
phiOT[1]->rowCache[3][3] =   1.0;

/* phi(3, 2) - yaw 2nd universal joint */
phiOT[2]->rowCache[1][1] =   1.0;
phiOT[2]->rowCache[4][4] =   1.0;

/* phi(4, 3) yaw - 1st universal joint */
phiOT[3]->rowCache[1][1] =   1.0;
phiOT[3]->rowCache[4][4] =   1.0;

/* phi(5, 4) pitch  1st universal joint */
phiOT[4]->rowCache[0][0] =   1.0;
phiOT[4]->rowCache[3][3] =   1.0;
```

```
    /* phi(6, 5) wrist roll */
    phiOT[5]->rowCache[2][2] =   1.0;
    phiOT[5]->rowCache[5][5] =   1.0;

/* phi(7,6) 2nd elbow joint */
    phiOT[6]->rowCache[0][0] =   1.0;
    phiOT[6]->rowCache[3][3] =   1.0;

/* phi(8,7) 1st elbow joint */
    phiOT[7]->rowCache[0][0] =   1.0;
    phiOT[7]->rowCache[3][3] =   1.0;

/* phi(9,8) 2nd shoulder joint */
    phiOT[8]->rowCache[0][0] =   1.0;
    phiOT[8]->rowCache[3][3] =   1.0;

/* phi(10,9) 1st shoulder joint */
    phiOT[9]->rowCache[0][0] =   1.0;
    phiOT[9]->rowCache[3][3] =   1.0;

/* phi(11, 10) torso roll */
    phiOT[10]->rowCache[2][2] =   1.0;
    phiOT[10]->rowCache[5][5] =   1.0;

return (TRUE);
}

/*
 * This is the rams_slave_ik component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int rams_slave_ikClass::execute()
{
    register int i, j;
    register float w1, w2, gb4v, gb5v;
    int indx[6], flg1, flg2;
```

```c
    float d;

#ifdef VERBOSE
    printf("In Inverse Kinematics\n");
    CSMatPrint(_deltaPos);
    CSMatPrint(_deltaOri);
#endif /* VERBOSE */

/* Compute the new values in the Phi matrices - change as joint
       angles change */
    update_slave_IK_matrices();

/* Put tip errors into a new matrix for pos and orientation */
    for ( i=0; i<3; i++ )
        tipErrVec->pr[i+3] = _deltaPos->pr[i];

matrix_to_roll_pitch_yaw(_deltaOri, tipErrVec);

/* Convert errTip to tip frame then put into tipErrVec vector */
    create_TR_matrix(_tipOri, 0.0, temp661matrix);
    CSMatMult(zVec, temp661matrix, tipErrVec);
    CSMatCopy(tipErrVec, zVec);

/* Compute the Jacobian matrix recursively */
    for ( i=5; i>-1; i-- ) {
        CSMatCopy(VVec, zero16matrix);
        for ( j=9; j>-1; j-- ) {
            mult_SA_661_matrix(phiOT[j+1], VVec, temp161matrix);
            if (((i==5)&&(j==9))
                ||(((j== 8)||(j== 7))&&(i==4))
                ||(((j== 6)||(j== 5))&&(i==3))
                ||((i==2)&&(j==4))
                ||(((j== 3)||(j== 0))&&(i==0))
                ||(((j==2)||(j== 1))&&(i==1))) {
                CSMatAdd(VVec, temp161matrix, HO[j]);
            }
            else CSMatCopy(VVec, temp161matrix);
        }
        for ( j=0; j<6; j++ )
            temp662matrix->rowCache[j][5-i] = VVec->pr[j];
    }

/* Do the LU decomp and back subst to get the kinematic model joint
       angle changes */
```

A153

```
CSMatLUdcmp(temp661matrix, temp662matrix, indx, &flg1, &flg2, &d);
CSMatLU_Solve(temp161matrix, temp661matrix, tipErrVec, indx);
/* Now need to convert to change in cable pulley angles */
/* Assume that the tip attitude matrix is current - the forward */
/* kinematics should have been computed in this cycle */
/* There is no transformation needed for the wrist roll joint and the torso, */
/* shoulder and elbow joints */
_deltaJoints->pr[0] = temp161matrix->pr[0];
_deltaJoints->pr[1] = temp161matrix->pr[1];
_deltaJoints->pr[2] = temp161matrix->pr[2];
_deltaJoints->pr[3] = temp161matrix->pr[3];

/* Do the conversion from universal joint angle velocities to the */
/* gear bail angle velocities */
w1 = _jointCosines->pr[1] * temp161matrix->pr[5] -
    _jointCosines->pr[0] * _jointSines->pr[1] * temp161matrix->pr[3];
w2 = temp161matrix->pr[4] + _jointSines->pr[0] *
    temp161matrix->pr[3];

/* joint 4 is the inner gear bail angle - see Guillermo's notes pg 7 */
gb4v = ((_wrist2UnivJnt->rowCache[2][2]*_wrist2UnivJnt->rowCache[1][1]
    - _wrist2UnivJnt->rowCache[2][1]*_wrist2UnivJnt->rowCache[1][2])*w1 +
    (_wrist2UnivJnt->rowCache[2][1]*_wrist2UnivJnt->rowCache[0][2]
    - _wrist2UnivJnt->rowCache[2][2]*_wrist2UnivJnt->rowCache[0][1])*w2)
    /( _wrist2UnivJnt->rowCache[2][2]*_wrist2UnivJnt->rowCache[2][2] +
    _wrist2UnivJnt->rowCache[2][1]*_wrist2UnivJnt->rowCache[2][1]);

/* joint 5 is the outer gear bail angle */
gb5v = ((_wrist2UnivJnt->rowCache[1][2]*_wrist2UnivJnt->rowCache[2][0]
    - _wrist2UnivJnt->rowCache[1][0]*_wrist2UnivJnt->rowCache[2][2])*w1 +
    (_wrist2UnivJnt->rowCache[0][0]*_wrist2UnivJnt->rowCache[2][2]
    - _wrist2UnivJnt->rowCache[0][2]*_wrist2UnivJnt->rowCache[2][0])*w2)
    /( _wrist2UnivJnt->rowCache[2][2]*_wrist2UnivJnt->rowCache[2][2] +
    _wrist2UnivJnt->rowCache[2][0]*_wrist2UnivJnt->rowCache[2][0]);

/* Now convert to the slider positions */
_deltaJoints->pr[4] = slave_gear_bail_angle_velocity_to_slider_velocity(
    gb4v, _gearBailAngles->pr[0]);
_deltaJoints->pr[5] = slave_gear_bail_angle_velocity_to_slider_velocity(
    gb5v, _gearBailAngles->pr[1]);

#ifdef VERBOSE
    CSMatPrint(_deltaJoints);
```

A154

```
#endif /* VERBOSE */
    return (0);
}

/*  *
==================================================================
========================
* Below are the method(s) that you have selected for this component
                                                                    *
==================================================================
==================== */

Package
void rams_slave_ikInitialize()
{
    /* Your initialization code for the entire class goes here. */
}
/***
  NAME
  update_slave_IK_matrices
  PURPOSE
  Update the inverse kinematics transformation matrices of the Rams slave robot.
  Joint values in the joints[] array should have been updated. These are
  the phi matrices of the RAMS robot from Guillermo Rodriguez's
  derivation of the kinemtic equations..
  NOTES

*/
int rams_slave_ikClass::update_slave_IK_matrices()
{

/* phi(1, 0) - Transformation from 2nd universal joint to tip */
    /*
    phiOT[0]->rowCache[0][0] = 1.0;
    phiOT[0]->rowCache[1][1] = 1.0;
    phiOT[0]->rowCache[2][2] = 1.0;
    phiOT[0]->rowCache[3][3] = 1.0;
    phiOT[0]->rowCache[4][4] = 1.0;
    phiOT[0]->rowCache[5][5] = 1.0;
    phiOT[0]->rowCache[4][0] = -_linkLengths->pr[0];
    phiOT[0]->rowCache[3][1] = _linkLengths->pr[0];
    */
```

```
/* phi(2, 1) - pitch 2nd universal joint */
/* phiOT[1]->rowCache[0][0] =    1.0; */
phiOT[1]->rowCache[1][1] =     _jointCosines->pr[0];
phiOT[1]->rowCache[2][1] = -   _jointSines->pr[0];
phiOT[1]->rowCache[2][2] =     _jointCosines->pr[0];
phiOT[1]->rowCache[1][2] =     _jointSines->pr[0];
/* phiOT[1]->rowCache[3][3] =    1.0; */
phiOT[1]->rowCache[4][4] =     _jointCosines->pr[0];
phiOT[1]->rowCache[5][4] = -   _jointSines->pr[0];
phiOT[1]->rowCache[4][5] =     _jointSines->pr[0];
phiOT[1]->rowCache[5][5] =     _jointCosines->pr[0];

/* phi(3, 2) - yaw 2nd universal joint */
phiOT[2]->rowCache[0][0] =     _jointCosines->pr[1];
phiOT[2]->rowCache[0][2] = -   _jointSines->pr[1];
/* phiOT[2]->rowCache[1][1] =    1.0; */
phiOT[2]->rowCache[2][0] =     _jointSines->pr[1];
phiOT[2]->rowCache[2][2] =     _jointCosines->pr[1];
phiOT[2]->rowCache[3][3] =     _jointCosines->pr[1];
phiOT[2]->rowCache[3][5] = -   _jointSines->pr[1];
/* phiOT[2]->rowCache[4][4] =    1.0; */
phiOT[2]->rowCache[5][3] =     _jointSines->pr[1];
phiOT[2]->rowCache[5][5] =     _jointCosines->pr[1];
phiOT[2]->rowCache[4][0] = -   _linkLengths->pr[2];
phiOT[2]->rowCache[3][1] =     _linkLengths->pr[2] * _jointCosines->pr[1];
phiOT[2]->rowCache[5][1] =     _linkLengths->pr[2] * _jointSines->pr[1];

/* phi(4, 3) yaw - 1st universal joint */
phiOT[3]->rowCache[0][0] =     _jointCosines->pr[2];
phiOT[3]->rowCache[0][2] = -   _jointSines->pr[2];
/* phiOT[3]->rowCache[1][1] =    1.0; */
phiOT[3]->rowCache[2][0] =     _jointSines->pr[2];
phiOT[3]->rowCache[2][2] =     _jointCosines->pr[2];
phiOT[3]->rowCache[3][3] =     _jointCosines->pr[2];
phiOT[3]->rowCache[3][5] = -   _jointSines->pr[2];
/* phiOT[3]->rowCache[4][4] =    1.0; */
phiOT[3]->rowCache[5][3] =     _jointSines->pr[2];
phiOT[3]->rowCache[5][5] =     _jointCosines->pr[2];

/* phi(5, 4) pitch 1st universal joint */
/* phiOT[4]->rowCache[0][0] =    1.0; */
phiOT[4]->rowCache[1][1] =     _jointCosines->pr[3];
phiOT[4]->rowCache[2][1] = -   _jointSines->pr[3];
phiOT[4]->rowCache[2][2] =     _jointCosines->pr[3];
```

A156

```
phiOT[4]->rowCache[1][2] =    _jointSines->pr[3];
/* phiOT[4]->rowCache[3][3] =   1.0; */
phiOT[4]->rowCache[4][4] =    _jointCosines->pr[3];
phiOT[4]->rowCache[5][4] = -  _jointSines->pr[3];
phiOT[4]->rowCache[4][5] =    _jointSines->pr[3];
phiOT[4]->rowCache[5][5] =    _jointCosines->pr[3];

/* phi(6, 5) wrist roll */
phiOT[5]->rowCache[0][0] =    _jointCosines->pr[4];
phiOT[5]->rowCache[0][1] =    _jointSines->pr[4];
phiOT[5]->rowCache[1][0] = -  _jointSines->pr[4];
phiOT[5]->rowCache[1][1] =    _jointCosines->pr[4];
/* phiOT[5]->rowCache[2][2] =   1.0; */
phiOT[5]->rowCache[3][3] =    _jointCosines->pr[4];
phiOT[5]->rowCache[3][4] =    _jointSines->pr[4];
phiOT[5]->rowCache[4][3] = -  _jointSines->pr[4];
phiOT[5]->rowCache[4][4] =    _jointCosines->pr[4];
/* phiOT[5]->rowCache[5][5] =   1.0; */
phiOT[5]->rowCache[3][0] = -  _linkLengths->pr[5] * _jointSines->pr[4];
phiOT[5]->rowCache[3][1] =    _linkLengths->pr[5] * _jointCosines->pr[4];
phiOT[5]->rowCache[4][0] = -  _linkLengths->pr[5] * _jointCosines->pr[4];
phiOT[5]->rowCache[4][1] = -  _linkLengths->pr[5] * _jointSines->pr[4];

/* phi(7,6) 2nd elbow joint */
/* phiOT[6]->rowCache[0][0] =   1.0; */
phiOT[6]->rowCache[1][1] =    _jointCosines->pr[5];
phiOT[6]->rowCache[2][1] = -  _jointSines->pr[5];
phiOT[6]->rowCache[2][2] =    _jointCosines->pr[5];
phiOT[6]->rowCache[1][2] =    _jointSines->pr[5];
/* phiOT[6]->rowCache[3][3] =   1.0; */
phiOT[6]->rowCache[4][4] =    _jointCosines->pr[5];
phiOT[6]->rowCache[5][4] = -  _jointSines->pr[5];
phiOT[6]->rowCache[4][5] =    _jointSines->pr[5];
phiOT[6]->rowCache[5][5] =    _jointCosines->pr[5];
phiOT[6]->rowCache[3][1] =    _linkLengths->pr[6];
phiOT[6]->rowCache[4][0] = -  _linkLengths->pr[6] * _jointCosines->pr[5];
phiOT[6]->rowCache[5][0] =    _linkLengths->pr[6] * _jointSines->pr[5];

/* phi(8,7) 1st elbow joint */
/* phiOT[7]->rowCache[0][0] =   1.0; */
phiOT[7]->rowCache[1][1] =    _jointCosines->pr[6];
phiOT[7]->rowCache[2][1] = -  _jointSines->pr[6];
phiOT[7]->rowCache[2][2] =    _jointCosines->pr[6];
```

A157

```
phiOT[7]->rowCache[1][2] =    _jointSines->pr[6];
/* phiOT[7]->rowCache[3][3] =   1.0; */
phiOT[7]->rowCache[4][4] =    _jointCosines->pr[6];
phiOT[7]->rowCache[5][4] = -  _jointSines->pr[6];
phiOT[7]->rowCache[4][5] =    _jointSines->pr[6];
phiOT[7]->rowCache[5][5] =    _jointCosines->pr[6];
phiOT[7]->rowCache[3][1] =    _linkLengths->pr[7];
phiOT[7]->rowCache[4][0] = -  _linkLengths->pr[7] * _jointCosines->pr[6];
phiOT[7]->rowCache[5][0] =    _linkLengths->pr[7] * _jointSines->pr[6];

/* phi(9,8) 2nd shoulder joint */
/* phiOT[8]->rowCache[0][0] =   1.0; */
phiOT[8]->rowCache[1][1] =    _jointCosines->pr[7];
phiOT[8]->rowCache[2][1] = -  _jointSines->pr[7];
phiOT[8]->rowCache[2][2] =    _jointCosines->pr[7];
phiOT[8]->rowCache[1][2] =    _jointSines->pr[7];
/* phiOT[8]->rowCache[3][3] =   1.0; */
phiOT[8]->rowCache[4][4] =    _jointCosines->pr[7];
phiOT[8]->rowCache[5][4] = -  _jointSines->pr[7];
phiOT[8]->rowCache[4][5] =    _jointSines->pr[7];
phiOT[8]->rowCache[5][5] =    _jointCosines->pr[7];
phiOT[8]->rowCache[3][1] =    _linkLengths->pr[8];
phiOT[8]->rowCache[4][0] = -  _linkLengths->pr[8] * _jointCosines->pr[7];
phiOT[8]->rowCache[5][0] =    _linkLengths->pr[8] * _jointSines->pr[7];

/* phi(10,9) 1st shoulder joint */
/* phiOT[9]->rowCache[0][0] =   1.0; */
phiOT[9]->rowCache[1][1] =    _jointCosines->pr[8];
phiOT[9]->rowCache[2][1] = -  _jointSines->pr[8];
phiOT[9]->rowCache[2][2] =    _jointCosines->pr[8];
phiOT[9]->rowCache[1][2] =    _jointSines->pr[8];
/* phiOT[9]->rowCache[3][3] =   1.0; */
phiOT[9]->rowCache[4][4] =    _jointCosines->pr[8];
phiOT[9]->rowCache[5][4] = -  _jointSines->pr[8];
phiOT[9]->rowCache[4][5] =    _jointSines->pr[8];
phiOT[9]->rowCache[5][5] =    _jointCosines->pr[8];
phiOT[9]->rowCache[3][1] =    _linkLengths->pr[9];
phiOT[9]->rowCache[4][0] = -  _linkLengths->pr[9] * _jointCosines->pr[8];
phiOT[9]->rowCache[5][0] =    _linkLengths->pr[9] * _jointSines->pr[8];

/* phi(11, 10) torso roll */
```

```
    phiOT[10]->rowCache[0][0] =    _jointCosines->pr[9];
    phiOT[10]->rowCache[0][1] =    _jointSines->pr[9];
    phiOT[10]->rowCache[1][0] = -  _jointSines->pr[9];
    phiOT[10]->rowCache[1][1] =    _jointCosines->pr[9];
 /* phiOT[10]->rowCache[2][2] =    1.0; */
    phiOT[10]->rowCache[3][3] =    _jointCosines->pr[9];
    phiOT[10]->rowCache[3][4] =    _jointSines->pr[9];
    phiOT[10]->rowCache[4][3] = -  _jointSines->pr[9];
    phiOT[10]->rowCache[4][4] =    _jointCosines->pr[9];
 /* phiOT[10]->rowCache[5][5] =    1.0; */ return (0);
}
```

```
/***
 NAME
 matrix_to_roll_pitch_yaw
 PURPOSE
 Compute the roll, pitch and yaw angles from the direction matrix.
 NOTES

*/ int rams_slave_ikClass::matrix_to_roll_pitch_yaw(CSMat dirMat, CSMat oriVec)
{
    oriVec->pr[0] = atan2(dirMat->rowCache[2][1], dirMat->rowCache[2][2]);

oriVec->pr[1] = atan2(-dirMat->rowCache[2][0],
                sqrt((dirMat->rowCache[0][0]*dirMat->rowCache[0][0])
             + (dirMat->rowCache[1][0]*dirMat->rowCache[1][0])));

oriVec->pr[2] = atan2(dirMat->rowCache[1][0], dirMat->rowCache[0][0]);
    return (0);
}
```

```
/***
 NAME
 mult_SA_661_matrix
 PURPOSE
 Perform multiplication between a spatial operator matrix and a vector.
 NOTES

*/
```

```
void rams_slave_ikClass::mult_SA_661_matrix( CSMat a, CSMat b, CSMat c )
{ c->rowCache[0][0] = a->rowCache[0][0] * b->rowCache[0][0] +
        a->rowCache[0][1] * b->rowCache[1][0] +
        a->rowCache[0][2] * b->rowCache[2][0];
    c->rowCache[1][0] = a->rowCache[1][0] * b->rowCache[0][0] +
        a->rowCache[1][1] * b->rowCache[1][0] +
        a->rowCache[1][2] * b->rowCache[2][0];
    c->rowCache[2][0] = a->rowCache[2][0] * b->rowCache[0][0] +
        a->rowCache[2][1] * b->rowCache[1][0] +
        a->rowCache[2][2] * b->rowCache[2][0];
    c->rowCache[3][0] = a->rowCache[3][0] * b->rowCache[0][0] +
        a->rowCache[3][1] * b->rowCache[1][0] +
        a->rowCache[3][2] * b->rowCache[2][0] +
        a->rowCache[3][3] * b->rowCache[3][0] +
        a->rowCache[3][4] * b->rowCache[4][0] +
        a->rowCache[3][5] * b->rowCache[5][0];
    c->rowCache[4][0] = a->rowCache[4][0] * b->rowCache[0][0] +
        a->rowCache[4][1] * b->rowCache[1][0] +
        a->rowCache[4][2] * b->rowCache[2][0] +
        a->rowCache[4][3] * b->rowCache[3][0] +
        a->rowCache[4][4] * b->rowCache[4][0] +
        a->rowCache[4][5] * b->rowCache[5][0];
    c->rowCache[5][0] = a->rowCache[5][0] * b->rowCache[0][0] +
        a->rowCache[5][1] * b->rowCache[1][0] +
        a->rowCache[5][2] * b->rowCache[2][0] +
        a->rowCache[5][3] * b->rowCache[3][0] +
        a->rowCache[5][4] * b->rowCache[4][0] +
        a->rowCache[5][5] * b->rowCache[5][0];

}

/***
    NAME
        createTRMatrix
    PURPOSE
        Create a 6x6 transformation matrix from a 3x3 transformation matrix
        and the z-axis translation vector of length l.

NOTES

*/
void rams_slave_ikClass::create_TR_matrix(CSMat rot, float l, CSMat tr)
```

```
{
    int i, j;

/* Do not need to do this everytime
    for  i=0; i<6; i++ )
        for (j=0; j<6; j++ )
            tr->rowCache[i][j] = 0.0;
        */ for ( i=0; i<3; i++ )
        for ( j=0; j<3; j++ )
            tr->rowCache[j+3][i+3] = tr->rowCache[j][i] = rot->rowCache[i][j];

/* DO not need to do this every time
    tr->rowCache[1][3] = -1;
    tr->rowCache[0][4] = 1;
    */
}
/***
    NAME
    slaveGearBailAngleVelocityToSliderVelocity
    PURPOSE
    Compute the slider velocity given the gear bail angle velocity.
    NOTES

*/
float
rams_slave_ikClass::slave_gear_bail_angle_velocity_to_slider_velocity(
    float gVel, float gearAngle)
{
    float c, s, slider;

s = sin(gearAngle);
    c = cos(gearAngle);

slider = SLAVERg*c - 2.0*( SLAVERg*SLAVERg*c*s - SLAVERg*SLAVEDs*s)/
        sqrt(SLAVELs*SLAVELs - SLAVERg*SLAVERg*c*c +
        2.0*SLAVERg*SLAVEDs*c - SLAVEDs*SLAVEDs);
    return(slider*gVel);
}

/* End of file */
```

A161

```
/******************************************************************
 *      Copyright (c) 1993 Jet Propulsion Laboratory
 *      U.S. Government Sponsorship under NASA Contract NAS7-1270 is acknowledge
 *
 *      Author: Hari Das
 *
 *      $Id: controlSlave.cc,v 1.3 1995/08/24 22:02:55 hari Exp hari $
 *      $Source: /home/hari/ram/software/cntrlShell/rams/components/control/RCS/controlSlave.cc,v $
 *      $Revision: 1.3 $
 *      $Date: 1995/08/24 22:02:55 $
 *      $Author: hari $
 ******************************************************************
 * $Log: controlSlave.cc,v $
// Revision 1.3  1995/08/24  22:02:55  hari
// Added comments and debugged.
//
// Revision 1.2  1995/05/04  21:38:22  hari
// *** empty log message ***
//
// Revision 1.1  1995/04/25  23:46:29  hari
// Initial revision
//
 *
 */ static char rcsid[] = "$Id: controlSlave.cc,v 1.3 1995/08/24 22:02:55 hari Exp hari $";

/***
    NAME
      controlSlave
    PURPOSE
      Control slave robot to desired joint positions.
    NOTES HISTORY
    Hari Das - Apr 25, 1995: Created.
***/

/* controlSlave \- Component short description
   banner = -----------

Name: controlSlave.cc
``` modification history
--------------------
rti,25Apr95,xxx Skeleton generated

DESCRIPTION:

Skeleton code segment for the controlSlave component.
Generated automatically by the ControlShell Component Editor.

Do not modify by hand!
This file should be copied to controlSlave.cc,
and the copy edited to suit your application.

DFE ENTRY FORMAT:

controlSlave: <InstanceName> <HabitatName>
    desJoints        <CSMat_input>
    joints           <CSMat_output>

EXAMPLE:

<none>
================================================================
============================ */

```
#include <stdio.h>
include <stdlib.h>
#include <math.h>
#include "CSMat.h"
#include "rtilib/makeheader.h"
include "cs.h"
#ifdef RTS_VXWORKS
include <vxWorks.h>
include <taskLib.h>
#include <vxLib.h>
#include <errnoLib.h>
#include <sysLib.h>
#include <logLib.h>
#include <semLib.h>
#include <timers.h>
#include <ioLib.h>
#include <semSmLib.h>
#include <smNameLib.h>
```

```
#include <vme.h>
#else
#include <string.h>
#endif /* RTS_VXWORKS */
#include "../slave/rams_slave.h"
```

Public typedef class controlSlaveClass *controlSlave;

Public
class controlSlaveClass : public CSComponentModuleClass { friend class controlSlaveParseClient;
private:
    /* Additional private members and methods */
    float jMax[6];
    float jMin[6];

protected:
    CSMat        _desJoints; /* input */
    CSMat        _joints; /* output */ virtual boolean userInstance();

/* Additional protected members and methods */ public:
    controlSlaveClass( const char *modulename,
                const boolean feedthrough,
                const char *habitatName );
    ~controlSlaveClass();

/* Component Methods */
    virtual int execute();

virtual boolean print( int verbosity );
    virtual void *instance();

/* Additional public routines */ virtual const char *const className() { return ("controlSlave"); }
};

```
controlSlaveClass::controlSlaveClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
} controlSlaveClass::~controlSlaveClass()
{
    CSdBaseRemoveRecord(className(), name());

/* Your destructor code goes here */
}

/*
 * This is the controlSlave component's user-instancing routine.
 * You can put custom instancing info here....info that does
 * not necessarily make sense in the Constructor.
 *
 * If error, return FALSE.
 *
 * If you remove this routine, you must also remove it from the class
 * definition above.
 */
boolean controlSlaveClass::userInstance()
{
    /* Set up the limits on the motion of the slave arm */
    jMax[0] = DEG_TO_RAD(45.0);
    jMax[1] = DEG_TO_RAD(90.0);
    jMax[2] = DEG_TO_RAD(90.0);
    jMax[3] = DEG_TO_RAD(90.0);
    jMax[4] = 0.25;
    jMax[5] = 0.25;

jMin[0] = DEG_TO_RAD(-45.0);
    jMin[1] = DEG_TO_RAD(-90.0);
    jMin[2] = DEG_TO_RAD(-90.0);
    jMin[3] = DEG_TO_RAD(-90.0);
    jMin[4] = - 0.25;
    jMin[5] = - 0.25;
```

```
        return (TRUE);
}
/*
 * This is the controlSlave component's main routine.
 * It is called each "loop". More precisely, it is normally installed
 * into an execution list (e.g. the "Sample" list), and executed each
 * time the list runs (e.g. at each sample clock).
 *
 * If there is an error, the function should return -1
 */
int controlSlaveClass::execute()
{
    register int i;

#ifdef VERBOSE
    printf("Desired joints are");
#endif /* ifdef VERBOSE */
    for ( i=0; i<6; i++ ) {
        if ( _desJoints->pr[i] > jMax[i] ) _desJoints->pr[i] = jMax[i];
        if ( _desJoints->pr[i] < jMin[i] ) _desJoints->pr[i] = jMin[i];
        _joints->pr[i] = _desJoints->pr[i];
#ifdef VERBOSE
        printf(" %f", _joints->pr[i]);
#endif /* ifdef VERBOSE */
    }
#ifdef VERBOSE
    printf("\n");
#endif /* ifdef VERBOSE */
    return (0);
}

/*                                                                            *
================================================================================
=========================
 * Below are the method(s) that you have selected for this component
                                                                              *
================================================================================
======================= */

Package
void controlSlaveInitialize()
{
```

```
    /* Your initialization code for the entire class goes here. */
}

/* End of file */
```

```
/*************************************************************\
 * Copyright (C) 1994, California Institute of Technology.
 * U.S. Government Sponsorship under NASA Contract NAS7-918 is acknowledged.
 *
 * Author: Hari Das
 *
 * $Id: slaveJointActuator.cc,v 1.2 1995/08/24 22:05:15 hari Exp hari $
 *
 *                    $   S   o   u   r   c   e   :
 * /home/hari/ram/software/cntrlShell/rams/components/dataio/RCS/slaveJointActuator.cc,v $
 *
\*************************************************************/

/***
   NAME
     slaveJointActuator
   PURPOSE

NOTES

HISTORY
     Hari Das - Aug 8, 1995: Created.
***/

/*************************************************************
 * $Log: slaveJointActuator.cc,v $
// Revision 1.2  1995/08/24  22:05:15  hari
// Added comments and debugged.
//
// Revision 1.1  1995/08/08  16:16:20  hari
// Initial revision
//
 *
 */ ifdef rcsid
static char rcsid[] = "$Id: slaveJointActuator.cc,v 1.2 1995/08/24 22:05:15 hari Exp hari $";
#endif /* matches #ifdef rcsid */

/*************************************************************/
/* slaveJointActuator \- Component short description
   banner = -----------
```

Name: slaveJointActuator.cc modification history
--------------------
rti,10Aug95,xxx Skeleton generated

DESCRIPTION:

Skeleton code segment for the slaveJointActuator component.
Generated automatically by the ControlShell Component Editor.

Do not modify by hand!
This file should be copied to slaveJointActuator.cc,
and the copy edited to suit your application.

DFE ENTRY FORMAT:

```
slaveJointActuator: <InstanceName> <HabitatName>
    controlJoints      <CSMat_input>
    slaveJointInput    <CSMat_output>
```

EXAMPLE:

<none>
============================================================
========================== */

```
#include <stdio.h>
include <stdlib.h>
#include <string.h>
include <math.h> include "rtilib/makeheader.h"
include "cs.h"
#pragma begin_Public
extern "C" {
#include "../slave/rams_slave.h"
}
pragma end_Public Public typedef class slaveJointActuatorClass *slaveJointActuator;
```

```
Public
class slaveJointActuatorClass : public CSComponentModuleClass { friend class slaveJointActuatorParseClient;
  private:
    /* Additional private members and methods */
    float          gear_ratios[6];  /* Vector of slave joint ratios */ protected:
    CSMat          _controlJoints;  /* input */
    CSMat          _slaveJointInput; /* output */ virtual boolean userInstance();

/* Additional protected members and methods */ public:
    slaveJointActuatorClass( const char *modulename,
                const boolean feedthrough,
                const char *habitatName );
    ~slaveJointActuatorClass();

/* Component Methods */
    virtual int execute();

virtual boolean print( int verbosity );
    virtual void *instance();

/* Additional public routines */ virtual const char *const className() { return ("slaveJointActuator"); }
};

slaveJointActuatorClass::slaveJointActuatorClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
}
```

```
slaveJointActuatorClass::~slaveJointActuatorClass()
{
    CSdBaseRemoveRecord(className(), name());

/* Your destructor code goes here */
}

/*
 * This is the slaveJointActuator component's user-instancing routine.
 * You can put custom instancing info here....info that does
 * not necessarily make sense in the Constructor.
 *
 * If error, return FALSE.
 *
 * If you remove this routine, you must also remove it from the class
 * definition above.
 */
boolean slaveJointActuatorClass::userInstance()
{
    /* Set up slave ojint ratios */
    gear_ratios[0] = SLAVE_GEAR_RATIO1;
    gear_ratios[1] = SLAVE_GEAR_RATIO2;
    gear_ratios[2] = SLAVE_GEAR_RATIO3;
    gear_ratios[3] = SLAVE_GEAR_RATIO4;
    gear_ratios[4] = SLAVE_GEAR_RATIO5;
    gear_ratios[5] = SLAVE_GEAR_RATIO6;

return (TRUE);
}

/*
 * This is the slaveJointActuator component's main routine.
 * It is called each "loop".  More precisely, it is normally installed
 * into an execution list (e.g. the "Sample" list), and executed each
 * time the list runs (e.g. at each sample clock).
 *
 * If there is an error, the function should return -1
 */
int slaveJointActuatorClass::execute()
{
ifdef RTS_VXWORKS /* Convert the slave joint setpoints in radians to encoder units */
    _slaveJointInput->pr[2] = - SLAVE_JNT_TO_ENC(_controlJoints->pr[0],
```

```
                                    gear_ratios[0]);
    _slaveJointInput->pr[0] = - SLAVE_JNT_TO_ENC(_controlJoints->pr[1],
                                    gear_ratios[1]);
    _slaveJointInput->pr[1] =   SLAVE_JNT_TO_ENC(_controlJoints->pr[2],
                                    gear_ratios[2]);
    _slaveJointInput->pr[5] =   SLAVE_JNT_TO_ENC(_controlJoints->pr[3],
                                    gear_ratios[3]);
    _slaveJointInput->pr[3] =   SLAVE_JNT_TO_ENC56(_controlJoints->pr[4],
                                    gear_ratios[4]);
    _slaveJointInput->pr[4] =   SLAVE_JNT_TO_ENC56(_controlJoints->pr[5],
                                    gear_ratios[5]);
endif /* ifdef RTS_VXWORKS */ return (0);
}

/* ===========================================================================
   ============================
 * Below are the method(s) that you have selected for this component          *
   ===========================================================================
   ==================== */

Package
void slaveJointActuatorInitialize()
{
    /* Your initialization code for the entire class goes here. */
}

/* End of file */
```

```
/****************************************************************\
 * Copyright (C) 1994, California Institute of Technology.
 * U.S. Government Sponsorship under NASA Contract NAS7-918 is acknowledged.
 *
 * Author: Hari Das
 *
 * $Id: slaveJointSensor.cc,v 1.2 1995/08/24 22:05:24 hari Exp hari $
 *
 *                          $ Source : /home/hari/ram/software/cntrlShell/rams/components/dataio/RCS/slaveJointSensor.cc,v $
 *
\****************************************************************/

/***
  NAME
    slaveJointSensor
  PURPOSE

NOTES

HISTORY
    Hari Das - Aug 8, 1995: Created.
***/

/****************************************************************
 * $Log: slaveJointSensor.cc,v $
// Revision 1.2  1995/08/24  22:05:24  hari
// Added comments and debugged.
//
// Revision 1.1  1995/08/08  16:16:31  hari
// Initial revision
//
 *
 */ ifdef rcsid
static char rcsid[] = "$Id: slaveJointSensor.cc,v 1.2 1995/08/24 22:05:24 hari Exp hari $";
#endif /* matches #ifdef rcsid */

/****************************************************************/
/* slaveJointSensor \- Component short description
   banner = ----------
```

Name: slaveJointSensor.cc modification history
--------------------
rti,10Aug95,xxx Skeleton generated

DESCRIPTION:

Skeleton code segment for the slaveJointSensor component.
Generated automatically by the ControlShell Component Editor.

Do not modify by hand!
This file should be copied to slaveJointSensor.cc,
and the copy edited to suit your application.

DFE ENTRY FORMAT:

slaveJointSensor: <InstanceName> <HabitatName>
    actualJoints       <CSMat_output>
    slaveJointOutput   <CSMat_input>

EXAMPLE:

<none>
===============================================================
========================= */

```
#include <stdio.h>
include <stdlib.h>
#include <string.h>
include <math.h> include "rtilib/makeheader.h"
include "cs.h"
#pragma begin_Public
extern "C" {
#include "../slave/rams_slave.h"
}
pragma end_Public Public typedef class slaveJointSensorClass *slaveJointSensor;
```

```
Public
class slaveJointSensorClass : public CSComponentModuleClass { friend class slaveJointSensorParseClient;
  private:
    /* Additional private members and methods */
    float           gear_ratios[6]; /* Vector of slave joint gear ratios */ protected:
    CSMat           _actualJoints;   /* output */
    CSMat           _slaveJointOutput; /* input */ virtual boolean userInstance();

/* Additional protected members and methods */ public:
    slaveJointSensorClass( const char *modulename,
                const boolean feedthrough,
                const char *habitatName );
    ~slaveJointSensorClass();

/* Component Methods */
    virtual int execute();

virtual boolean print( int verbosity );
    virtual void *instance();

/* Additional public routines */ virtual const char *const className() { return ("slaveJointSensor"); }
};

slaveJointSensorClass::slaveJointSensorClass(
    const char *modulename,
    const boolean feedthrough,
    const char *habitatName)
    : CSComponentModuleClass(modulename, feedthrough, habitatName)
{
    CSdBaseEnterRecord(className(), name(), this);

/* Additional initialization code goes here. */
}
```

A175

```
slaveJointSensorClass::~slaveJointSensorClass()
{
    CSdBaseRemoveRecord(className(), name());

/* Your destructor code goes here */
}

/*
 * This is the slaveJointSensor component's user-instancing routine.
 * You can put custom instancing info here....info that does
 * not necessarily make sense in the Constructor.
 *
 * If error, return FALSE.
 *
 * If you remove this routine, you must also remove it from the class
 * definition above.
 */
boolean slaveJointSensorClass::userInstance()
{
    /* Set up the gear ratios */
    gear_ratios[0] = SLAVE_GEAR_RATIO1;
    gear_ratios[1] = SLAVE_GEAR_RATIO2;
    gear_ratios[2] = SLAVE_GEAR_RATIO3;
    gear_ratios[3] = SLAVE_GEAR_RATIO4;
    gear_ratios[4] = SLAVE_GEAR_RATIO5;
    gear_ratios[5] = SLAVE_GEAR_RATIO6;

return (TRUE);
}

/*
 * This is the slaveJointSensor component's main routine.
 * It is called each "loop".  More precisely, it is normally installed
 * into an execution list (e.g. the "Sample" list), and executed each
 * time the list runs (e.g. at each sample clock).
 *
 * If there is an error, the function should return -1
 */
int slaveJointSensorClass::execute()
{
ifdef RTS_VXWORKS /* Convert the slave joint encoder readings to joint angles in
    radians */
```

```
_actualJoints->pr[0] =
    - SLAVE_ENC_TO_JNT(((float)_slaveJointOutput->pr[2]), gear_ratios[0]);
_actualJoints->pr[1] =
    - SLAVE_ENC_TO_JNT(((float)_slaveJointOutput->pr[0]), gear_ratios[1]);
_actualJoints->pr[2] =
    SLAVE_ENC_TO_JNT(((float)_slaveJointOutput->pr[1]), gear_ratios[2]);
_actualJoints->pr[3] =
    SLAVE_ENC_TO_JNT(((float)_slaveJointOutput->pr[5]), gear_ratios[3]);
_actualJoints->pr[4] =
    SLAVE_ENC_TO_JNT56(((float)_slaveJointOutput->pr[3]), gear_ratios[4]);
_actualJoints->pr[5] =
    SLAVE_ENC_TO_JNT56(((float)_slaveJointOutput->pr[4]), gear_ratios[5]);

endif /* RTS_VXWORKS */ return (0);
}

/ *
======================================================================
=========================
* Below are the method(s) that you have selected for this component   *
======================================================================
==================== */

Package
void slaveJointSensorInitialize()
{
    /* Your initialization code for the entire class goes here. */
}

/* End of file */
```

A177

What is claimed is:

1. A robot manipulator, comprising:
   an actuator base with plural actuators;
   an end effector;
   plural arms extending seriatim between said end effector and said actuator base; and
   plural joints connected between pairs of adjacent arms;
   wherein each one of said plural joints comprises means for mechanically coupling respective ones of said actuators to respective ones of said joints through intermediate ones of said joints, and wherein said means for mechanically coupling is decoupled from said intermediate joints.

2. The invention as set forth in claim 1, wherein said means for mechanically coupling comprises:
   a first keying drive component coupled to a second keying drive component;
   a first passing drive component coupled to respective ones of said actuators for receiving rotational motion; and
   a second passing drive component coupled to said first passing drive component for receiving said rotational motion from said first passing drive component and for transmitting said received rotational motion to one of said plural joints;
   wherein said first and second keying drive components are constrained to rotate about one another to define an instantaneous center of rotation;
   wherein said first passing drive component rotates with respect to said second passing drive component about said instantaneous center of rotation.

3. The invention as set forth in claim 2, wherein said first keying drive component is a first keying pulley and said second keying drive component is a second keying pulley.

4. The invention as set forth in claim 3, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

5. The invention as set forth in claim 2, wherein said first and second keying drive components are keying spur gears.

6. The invention as set forth in claim 2, wherein said first and second passing drive components are passing spur gears.

7. The invention as set forth in claim 2, wherein said first passing drive component is a first passing pulley and said second passing drive component is a second passing pulley.

8. The invention as set forth in claim 7, further comprising plural passing cables for rotatably coupling said first passing pulley to said second passing pulley and for rotationally constraining said first passing pulley to said second passing pulley so that said first and second passing pulleys rotate with respect to one another about said instantaneous center of rotation.

9. The invention as set forth in claim 1, wherein all actuators drives of said manipulator are located within said actuator base.

10. The invention as set forth in claim 1, wherein each of said joints comprises dual independent antibacklash drive transmission preloaded with respect to one another.

11. The invention as set forth in claim 1, wherein said plural joints further comprises an antibacklash mechanism for transmitting motion without backlash from respective ones of said plural actuator drives to respective ones of said joints, said antibacklash mechanism comprising:
   at least a first transmission stage comprising first dual drive components, wherein both of said first dual drive components are rotatably coupled to said respective ones of said plural actuator drives and are independently rotatable with respect to one another; and
   at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said plural actuator drives is transmitted through said first and second stages, to said respective ones of said joints without backlash.

12. A robot manipulator having an actuator and a plurality of decoupled joints, wherein each one of said decoupled joints comprises:
   an input link having at least an input keying drive component rotatable on an input axis;
   an output link coupled to said input link and having at least an output keying drive component rotatable on an output axis;
   wherein said input and output keying drive components are constrained to rotate about one another to define an instantaneous center of rotation;
   at least an input passing drive component rotatable on said input link and coupled to said actuator for receiving rotational motion; and
   at least an output passing drive component rotatable on said output link and coupled to said input passing drive component for receiving said rotational motion decoupled from said one joint.

13. The invention as set forth in claim 12, wherein said input passing drive component rotates with respect to said output passing drive component about said instantaneous center of rotation.

14. The invention as set forth in claim 12, wherein said input keying drive component is an input keying pulley and said output keying drive component is an output keying pulley.

15. The invention as set forth in claim 14, further comprising plural keying cables for rotatably coupling said input keying pulley to said output keying pulley and for rotationally constraining said input keying pulley to said output keying pulley so that said input and output keying pulleys rotate with respect to one another about said instantaneous center of rotation.

16. The invention as set forth in claim 12, wherein said input and output keying drive components are keying spur gears.

17. The invention as set forth in claim 12, wherein said input and output passing drive components are passing spur gears.

18. The invention as set forth in claim 12, wherein said input passing drive component is an input passing pulley and said output passing drive component is an output passing pulley.

19. The invention as set forth in claim 18, further comprising plural passing cables for rotatably coupling said input passing pulley to said output passing pulley and for rotationally constraining said input passing pulley to said output passing pulley so that said input and output passing pulleys rotate with respect to one another about said instantaneous center of rotation.

20. The invention as set forth in claim 12, wherein said input and output links are coupled to each other by hinged side struts.

21. The invention as set forth in claim 12, wherein said input link further comprises plural input idler pulleys and said output link further comprises corresponding plural output idler pulleys, wherein each corresponding pair of said input and output idler pulleys drives one of said joints.

22. A robot manipulator having an actuator and a plurality of decoupled joints, wherein each one of said decoupled joints comprises:
   an input link having an input keying pulley;
   an output link coupled to said input link and having an output keying pulley;
   a keying cable for rotatably coupling said input keying pulley to said output keying pulley, wherein said input and output keying pulleys are constrained to rotate about one another thereby defining an instantaneous center of rotation;
   at least one input idler pulley rotatable on said input link and coupled to said actuator for receiving rotational motion;
   at least one output idler pulley rotatable on said output link; and
   at least one passing cable coupled to each input and output idler pulley for transmitting rotational motion of said input idler pulley and said output idler pulley decoupled from said one joint.

23. The invention as set forth in claim 22, wherein said input idler puller rotates with respect to said output idler pulley about said instantaneous center of rotation.

24. The invention as set forth in claim 22, wherein said input and output links are coupled to each other by hinged side struts.

25. The invention as set forth in claim 22, wherein said input and output links are displaced by at least a diameter of each of said input and output links to facilitate 180 degree rotation.

26. The invention as set forth in claim 22, wherein each of said joint's rotation is dependant upon a ratio between said input and output keying pulleys' diameters.

27. The invention as set forth in claim 22, wherein all of said keying pulleys have the same diameter.

28. The invention as set forth in claim 22, wherein said input link further comprises plural input keying pulleys and said output link further comprises plural output keying pulleys.

29. An antibacklash mechanism for transmitting motion without backlash from an input rotating device to an output rotating device, said antibacklash mechanism comprising:
   at least a first transmission stage comprising first dual drive components, wherein both of said first dual drive components are rotatably coupled to said input rotating device and are independently rotatable with respect to one another; and
   at least a second transmission stage comprising second dual drive reduction means, wherein each one of said second dual drive reduction means is rigidly attached to one of said first dual drive components and is rotatably coupled to said output device, whereby rotational motion of said input rotating device is transmitted from said input device, through said first and second stages, to said output device without backlash.

30. The invention set forth in claim 29, wherein each of said first dual drive components is a spur gear.

31. The invention set forth in claim 29, wherein each of said second dual drive reduction means is a pinion gear.

32. The invention set forth in claim 29, wherein each of said second dual drive reduction means is rotatably coupled to said output device with a dual drive pulley.

33. The invention set forth in claim 29, further comprising means for preloading said first transmission stage relative to said second transmission stage in order to eliminate backlash.

34. The invention set forth in claim 33, further comprising means for locking said first and second transmission stages after said first and second transmission stages are preloaded.

35. A multiple degree of freedom robot having a plurality of arm joints, a wrist joint coupled to one of said arm joints and having a tip, and a computer control system, said computer control system comprising:
   a user interface for receiving user commands;
   a servo controller coupled to said arm and wrist joints for reading actual positions of said arm and wrist joints; and
   a real-time kinematic processor coupled to said user interface and said servo controller for receiving said user commands and said actual positions of said arm and wrist joints for computing forward and inverse kinematic relationships for controlling said arm and wrist joints in accordance with said user commands and said computed relationships;
   wherein said real-time kinematic processor comprising:
      (a) means for setting a vector of tip displacements at said robot to zero,
      (b) means for computing at each joint a displacement vector corresponding to a unit motion at a current joint,
      (c) means for multiplying a displacement vector at said current joint by a transition matrix of a succeeding joint to produce a result,
      (d) means for multiplying said result by a joint axis vector of said current joint,
      (e) means for multiplying said result by said transition matrix to define a transition from a last joint to said tip,
      (f) means for setting said vector as a respective column of a jacobian matrix, and
      (g) means for multiplying a user defined vector of tip displacements by said jacobian matrix to compute corresponding joint angle displacements;
   wherein said servo controller implements said joint angle displacements.

36. The invention as set forth in claim 35, wherein said means for setting said vector as a respective column of a jacobian matrix corresponds to an independent degree of freedom of each of said joints for each independent degree of freedom of said robot.

37. The invention as set forth in claim 35, wherein said robot further comprises means coupled between said servo controller and each of said joints for moving said joints robot in accordance with said joint angle displacements.

38. The invention as set forth in claim 35, wherein said real-time kinematic processor further comprises means for determining a set of joint coordinate displacements corresponding to a desired set of tip coordinate displacements, means for computing a jacobian matrix, and means for adding said jacobian matrix to said tip coordinate displacements to produce a corresponding joint coordinate displacement.

39. The invention as set forth in claim 35, wherein said real-time kinematic processor further comprises means for setting up and computing a transition matrix defining a position and rotation transition between successive joints of said robot, means for setting up vectors defining axes of rotation of each of said joint, and means for transforming each of said joint to a desired position and an orientation change of said tip from a world reference frame to a tip reference frame.

40. The invention as set forth in claim 39, wherein said means for multiplying a user defined vector of tip displacements by said jacobian matrix is constrained by said tip reference frame.

41. A robot manipulator, comprising:
an actuator base with plural actuator drives;
a wrist with a tip;
plural arms extending seriatim between said wrist and said actuator base;
plural joints connected between pairs of adjacent arms;
wherein each of said plural joints comprises means for mechanically coupling respective ones of said actuators to respective ones of said joints through intermediate ones of said joints, and wherein said means for mechanically coupling is decoupled from said intermediate joints;
a user interface for receiving user commands;
a servo controller coupled to said arm and wrist joints for reading actual positions of said arm and wrist joints; and
a real-time kinematic processor coupled to said user interface and said servo controller for receiving said user commands and said actual positions of said arm and wrist joints for computing forward and inverse kinematic relationships for controlling said arm and wrist joints in accordance with said user commands and said computed relationships;
wherein said real-time kinematic processor comprising:
(a) means for setting a vector of tip displacements at said wrist to zero,
(b) means for computing at each joint a displacement vector corresponding to a unit motion at a current joint,
(c) means for multiplying a displacement vector at said current joint by a transition matrix of a succeeding joint to produce a result,
(d) means for multiplying said result by a joint axis vector of said current joint,
(e) means for multiplying said result by said transition matrix to define a transition from a last joint to said tip,
(f) means for setting said vector as a respective column of a jacobian matrix, and
(g) means for multiplying a user defined vector of tip displacements by said jacobian matrix to compute corresponding joint angle displacements;
wherein said servo controller implements said joint angle displacements.

42. The invention as set forth in claim 41, wherein said robot further comprises an antibacklash mechanism for transmitting motion without backlash from respective ones of said plural actuator drives to respective ones of said joints, said antibacklash mechanism comprising:
at least a first transmission stage comprising first dual drive components, wherein both of said first dual drive components are rotatably coupled to said respective ones of said plural actuator drives and are independently rotatable with respect to one another; and
at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said plural actuator drives is transmitted through said first and second stages, to said respective ones of said joints without backlash.

43. A method for manipulating a multiple degree of freedom robot having a plurality of arm joints, a wrist joint coupled to one of said arm joints and having a tip, a user interface for receiving user commands, a servo controller coupled to said arm and wrist joints for reading actual positions of said arm and wrist joints, said method comprising:
(a) determining a set of joint coordinate displacements corresponding to a desired set of tip coordinate displacements, computing a jacobian matrix, and adding said jacobian matrix to said tip coordinate displacements to produce a corresponding joint coordinate displacement by:
(1) setting up and computing a transition matrix defining a position and rotation transition between successive joints of said robot,
(2) setting up vectors defining axes of rotation of each of said joint,
(3) transforming to a desired position and an orientation change of said tip from a world reference frame to a tip reference frame;
(4) setting a vector of tip displacements at said robot to zero, computing at each joint a displacement vector corresponding to a unit motion at a current joint by multiplying a displacement vector at said current joint by a transition matrix of a succeeding joint to produce a result, multiplying said result by a joint axis vector of said current joint, multiplying said result by said transition matrix defining a transition from a last joint to said tip, and setting said vector as a respective column of a jacobian matrix, and
(5) multiplying a user defined vector of tip displacements by said jacobian matrix to compute corresponding joint angle displacements; and
(b) implementing said joint angle displacements by said servo controller in response to step (a).

44. The invention as set forth in claim 40, wherein the setting said vector as a respective column of a jacobian matrix step corresponds to an independent degree of freedom of each of said joints for each independent degree of freedom of said robot.

45. The invention as set forth in claim 43, wherein the multiplying a user defined vector of tip displacements by said jacobian matrix step is constrained by said tip reference frame.

46. A multiple degree of freedom microsurgical robot manipulator, comprising:
a plurality of miniaturized decoupled robot joints comprising a plurality of arm joints each having a first keying pulley constrained to rotate about a second keying pulley, thereby defining an instantaneous center of rotation to effectuate one degree of freedom movement, and a miniaturized wrist joint coupled to one of said arm joints and having a tip and three degrees of freedom;
a plurality of miniaturized driving cables, each coupled an actuator drive at a proximal end and coupled to one of said joints at a distal end; and
a computer control system coupled to each of said robot actuator drives comprising:
(a) a servo-control sub-system for reading actual joint positions of said robot joints;

(b) a high level sub-system for receiving user commands from a user interface and for receiving actual joint positions from said servo sub-system, wherein said high level sub-system sends said user commands and said actual joint positions to a real-time kinematic processor having a forward kinematic processor and an inverse kinematic recursive processor for computing forward and inverse kinematic relationships of said joints;

(c) wherein said sub-system comprises means for determining a set of joint coordinate displacements corresponding to a desired set of tip coordinate displacements, means for computing a jacobian matrix, and means for adding said jacobian matrix to said tip coordinate displacements to produce a corresponding joint coordinate displacement;

(d) wherein said servo sub-system implements said joint coordinate displacements.

47. The invention as set forth in claim 46, wherein each of said actuator drives comprises a plurality of motors with rotational motion and having optical encoders for effecting micro-rotation of said motors and for transmitting said rotational motion of said motors to said driving cables.

48. The invention as set forth in claim 46, wherein said robot further comprises an antibacklash mechanism for transmitting motion without backlash from respective ones of said actuator drives to respective ones of said joints, said antibacklash mechanism comprising:

at least a first transmission stage comprising first dual drive components, wherein both of said first dual drive components are rotatably coupled to said respective ones of said actuator drives and are independently rotatable with respect to one another; and at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said actuator drives is transmitted through said first and second stages, to said respective ones of said joints without backlash.

49. The invention as set forth in claim 46, wherein said real-time kinematic processor comprises:

a) means for setting a vector of tip displacements at said wrist to zero;

(b) means for computing at each joint a displacement vector corresponding to a unit motion at a current joint;

(c) means for multiplying a displacement vector at said current joint by a transition matrix of a succeeding joint to produce a result;

(d) means for multiplying said result by a joint axis vector of said current joint;

(e) means for multiplying said result by said transition matrix to define a transition from a last joint to said tip;

(f) means for setting said vector as a respective column of a jacobian matrix; and (g) means for multiplying a user defined vector of tip displacements by said jacobian matrix to compute corresponding joint angle displacements.

50. The invention as set forth in claim 46, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

51. The invention as set forth in claim 46, wherein said first and second keying pulleys are keying spur gears.

52. The invention as set forth in claim 46, wherein said first and second passing drive components are passing spur gears.

53. The invention as set forth in claim 46, further comprising:

a first passing drive component coupled to said driving cables of respective ones of said actuators for receiving rotational motion; and a second passing drive component coupled to said first passing drive component for receiving said rotational motion from said first passing drive component and for transmitting said received rotational motion to one of said joints;

wherein said first passing drive component rotates with respect to said second passing drive component about said instantaneous center of rotation.

54. The invention as set forth in claim 53, wherein said first passing drive component is a first passing pulley and said second passing drive component is a second passing pulley.

55. The invention as set forth in claim 54, further comprising plural passing cables for rotatably coupling said first passing pulley to said second passing pulley and for rotationally constraining said first passing pulley to said second passing pulley so that said first and second passing pulleys rotate with respect to one another about said instantaneous center of rotation.

56. The invention as set forth in claim 46, further comprising an input link coupled between each of said first keying pulley and each of said robot arm joints, and an output link coupled between each of said second keying pulley and each of said robot arm joint.

57. The invention as set forth in claim 56, wherein said input link further comprises plural input keying pulleys and said output link further comprises plural output keying pulleys.

58. The invention as set forth in claim 57, wherein said input link further comprises plural input passing pulleys and said output link further comprises corresponding plural output passing pulleys, wherein each corresponding pair of said input and output passing pulleys drives one of said joints.

59. The invention as set forth in claim 57, wherein said input and output links are coupled to each other by hinged side struts.

60. The invention as set forth in claim 46, wherein said computer control system further comprises:

a manual joint module, an auto joint module, a forward kinematic module, an inverse kinematic module, a sum joints module, a control joints module, and a servo-controller module;

means for receiving user commands by said manual joint module for changing joint angles and positions of each of said robot joints for a particular computation cycle; and means for receiving user commands by said auto joint module for starting, stopping, and selecting combinations of movement of said joints for changing joint angles and said position of each of said robot joints for a particular computation cycle.

61. The invention as set forth in claim 60, further comprising:

means for receiving said joint angles and positions from said auto joints module by said control joints module for limiting said joint angles sent to said servo-controller; and means for receiving said joint angles and positions from said sum joints module by said servo-controller module, for reading actual angles and positions of said robot joints, and for sending said actual angles and positions to said servo controller for controlling said robot joints.

62. The invention as set forth in claim 61, further comprising:

means for receiving said robot joint angles from said control joints module and said servo controller module by said forward kinematic module for computing a forward kinematic relationship of said robot joints;

means for receiving a portion of said forward kinematic relationship from said forward kinematic module by said inverse kinematic module for computing an inverse kinematic relationship of said robot joints in order to determine changes in said robot joint angles.

63. The invention as set forth in claim 62, further comprising:

means for receiving said changes in joint angles and positions from said inverse kinematic module and said actual joint angle positions from said servo controller module by said sum joints module for computing a sum of said desired change in said joint angle positions and current joint angle positions.

64. The invention as set forth in claim 63, further comprising:

means for receiving user commands and a portion of said forward kinematic relationship by said manual cartesian module for computing a cartesian position change of said robot tip and for changing a position of each of said cartesian position and orientation of said robot tip for a particular computation cycle;

means for receiving user commands and a portion of said forward kinematic relationship by said auto cartesian module for starting, stopping and selecting combinations of tip coordinates and for computing a change in said robot tip position and orientation in order to continuously move said selected tip coordinates and for changing a position of each of said robot tip coordinates for each cycle; and means for receiving data from said manual and auto cartesian modules for computing and sending a difference between said desired tip position and said actual tip position and a difference between said desired tip orientation and said actual tip orientation to said inverse kinematic module.

* * * * *